US012692499B2

(12) United States Patent
Morris et al.

(10) Patent No.: US 12,692,499 B2
(45) Date of Patent: Jul. 28, 2026

(54) LIPID NANOPARTICLES AND METHODS OF USE

(71) Applicant: City of Hope, Duarte, CA (US)

(72) Inventors: Kevin Morris, Duarte, CA (US); Alicia Davis, Duarte, CA (US); Tristan Scott, Pasadena, CA (US); Roslyn Ray, Monrovia, CA (US); Denis O'Meally, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 295 days.

(21) Appl. No.: 18/285,964

(22) PCT Filed: Apr. 6, 2022

(86) PCT No.: PCT/US2022/023615
§ 371 (c)(1),
(2) Date: Oct. 6, 2023

(87) PCT Pub. No.: WO2022/216787
PCT Pub. Date: Oct. 13, 2022

(65) Prior Publication Data
US 2024/0229034 A1 Jul. 11, 2024

Related U.S. Application Data

(60) Provisional application No. 63/172,209, filed on Apr. 8, 2021.

(51) Int. Cl.
*C12N 15/113* (2010.01)
*A61K 31/7105* (2006.01)
*A61K 47/69* (2017.01)

(52) U.S. Cl.
CPC ...... *C12N 15/1131* (2013.01); *A61K 31/7105* (2013.01); *A61K 47/6925* (2017.08); *C12N 2310/14* (2013.01)

(58) Field of Classification Search
CPC ............ C12N 15/1131; C12N 2310/14; A61K 47/6929; A61K 31/7105
See application file for complete search history.

(56) References Cited

U.S. PATENT DOCUMENTS

| | | | |
|---|---|---|---|
| 2006/0257852 A1* | 11/2006 | Rappuoli ............. | A61K 39/215 435/69.3 |
| 2017/0151333 A1 | 6/2017 | Heyes et al. | |
| 2019/0030187 A1* | 1/2019 | Lu ........................ | A61K 47/543 |
| 2019/0216843 A1 | 7/2019 | DeRosa et al. | |
| 2021/0085619 A1 | 3/2021 | Baldwin | |

FOREIGN PATENT DOCUMENTS

| | | | |
|---|---|---|---|
| CN | 111139241 B | | 9/2020 |
| CN | 111139242 B | | 9/2020 |
| WO | WO 2020/206231 | * | 10/2020 |
| WO | WO-2020/206231 A1 | | 10/2020 |

OTHER PUBLICATIONS

Alameh, M.-G. et al. (2021). "Lipid nanoparticles enhance the efficacy of mRNA and protein subunit vaccines by inducing robust T follicular helper cell and humoral responses," *Immunity* 54(12):2877-2892.e7.

Channappanavar, R. et al. (Jul. 2017, e-published May 2, 2017). "Pathogenic human coronavirus infections: causes and consequences of cytokine storm and immunopathology," *Semin Immunopathol* 39(5):529-539.

Hu, B. et al. (Mar. 2021). "Characteristics of SARS-CoV-2 and COVID-19," *Nat Rev Microbiol* 19(3)141-154.

Kedmi, R. et al. (Sep. 2010, e-published Jun. 11, 2010). "The systemic toxicity of positively charged lipid nanoparticles and the role of Toll-like receptor 4 in immune activation," *Biomaterials* 31(26):6867-6875.

Kumar, V. et al. (Nov. 18, 2014). "Shielding of Lipid Nanoparticles for siRNA Delivery: Impact on Physicochemical Properties, Cytokine Induction, and Efficacy," *Mol Ther Nucleic Acids* 3(11):e210.

Maugeri, M. et al. (Sep. 24, 2019). "Linkage between endosomal escape of LNP-mRNA and loading into EVs for transport to other cells," *Nat Commun* 10(1):4333.

Mccaskill, J. et al. (Jun. 4, 2013). "Efficient Biodistribution and Gene Silencing in the Lung epithelium via Intravenous Liposomal Delivery of siRNA," *Mol Ther Nucleic Acids* 2(6):e96.

Mccray, P.B. Jr. et al. (Jan. 2007, e-published Nov. 1, 2006). "Lethal infection of K18-hACE2 mice infected with severe acute respiratory syndrome coronavirus," *J Virol* 81(2):813-821.

Riley, R.S. et al. (Jan. 13, 2021). "Ionizable lipid nanoparticles for in utero mRNA delivery," *Sci Adv* 7:eaba1028.

Wu, S.Y. et al. (Mar. 2009, e-published Nov. 21, 2008). "Development of a novel method for formulating stable siRNA-loaded lipid particles for in vivo use," *Pharm Res* 26(3):512-522.

Xue, H.Y. et al. (Feb. 2014). "Nanotoxicity: a key obstacle to clinical translation of siRNA-based nanomedicine," *Nanomedicine (Lond)* 9(2):295-312.

Yilla, M. et al. (Jan. 2005). "SARS-coronavirus replication in human peripheral monocytes/macrophages," *Virus Res* 107(1):93-101.

Zolnik, B.S. et al. (Feb. 2010, e-published Dec. 16, 2009). "Nanoparticles and the immune system," *Endocrinology* 151(2):458-465.

Cheng, Q. et al. (Apr. 2020, e-published). "Selective organ targeting (SORT) nanoparticles for tissue-specific mRNA delivery and CRISPR-Cas gene editing," *Nat Nanotechnol* 15(4):313-320.

(Continued)

*Primary Examiner* — Shirley V Gembeh

(74) *Attorney, Agent, or Firm* — Mintz, Levin, Cohn, Ferris, Glovsky and Popeo, P.C.

(57) ABSTRACT

Provided herein are, inter alia, lipid nanoparticles, lipid nanoparticles comprising nucleic acids encapsulated therein, pharmaceutical compositions comprising lipid nanoparticles which comprise nucleic acids encapsulated therein, and methods of treating diseases, such as coronavirus infections (e.g., SARS-CoV-2, SARS-CoV-2, MERS-CoV), COVID, and MERS.

20 Claims, 17 Drawing Sheets

Specification includes a Sequence Listing.

(56) References Cited

OTHER PUBLICATIONS

GenBank:MN988668.1, (Feb. 11, 2020). Severe acute respiratory syndrome coronavirus 2 isolate 2019-nCoV WHU01, complete genome, 10 pages.

International Search Report mailed on Oct. 5, 2022, for PCT Application No. PCT/US2022/023615, filed Apr. 6, 2022, 6 pages.

Written Opinion mailed on Oct. 5, 2022, for PCT Application No. PCT/US2022/023615, filed Apr. 6, 2022, 8 pages.

\* cited by examiner

LIPID NANOPARTICLES AND METHODS OF USE

RELATED APPLICATIONS

This application is a Section 371 US national phase of International Application No. PCT/US2022/023615 filed Apr. 6, 2022, which claims priority to U.S. Application No. 63/172,209 filed Apr. 8, 2021, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under grant no. MH113407 awarded by National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-801001WO_SL_ST25.txt, created Mar. 18, 2022, 16,927 bytes, machine format IBM-PC, MS Windows operating system, is hereby incorporated by reference.

BACKGROUND

Lipid nanoparticles (LNPs) are effective drug delivery systems for biologically active compounds, such as therapeutic nucleic acids, proteins, and peptides, which are otherwise cell impermeable. Drugs based on nucleic acids, which include large nucleic acid molecules such as, in vitro transcribed messenger RNA as well as smaller polynucleotides that interact with a messenger RNA or a gene, have to be delivered to the proper cellular compartment in order to be effective. For example, double-stranded nucleic acids such as double-stranded RNA molecules (dsRNA), including siRNAs suffer from their physico-chemical properties that render them impermeable to cells. Upon delivery into the proper compartment, siRNAs block gene expression through a highly conserved regulatory mechanism known as RNA interference (RNAi). Typically, siRNAs are highly anionic due to their phosphate backbone with up to 50 negative charges. In addition, the two complementary RNA strands result in a rigid helix. These features contribute to the siRNA's poor "drug-like" properties. When administered intravenously, the siRNA is rapidly excreted from the body with a typical half-life in the range of only 10 minutes. Additionally, siRNAs are rapidly degraded by nucleases present in blood and other fluids or in tissues and have been shown to stimulate strong immune responses in vitro and in vivo. mRNA molecules suffer from similar issues of impermeability, fragility, and immunogenicity.

Lipid nanoparticle formulations have improved nucleic acid delivery in vivo. For example, such formulations have significantly reduced siRNA doses necessary to achieve target knockdown in vivo. Typically, such lipid nanoparticle drug delivery systems are multi-component formulations comprising cationic lipids, helper lipids, and lipids containing polyethylene glycol. The positively charged cationic lipids bind to the anionic nucleic acid, while the other components support a stable self-assembly of the lipid nanoparticles.

There is a need in the art for improved lipid nanoparticles and for improved delivery of lipid nanoparticles, particularly to the lungs. The disclosure is directed to this, as well as other, important ends.

BRIEF SUMMARY

Provided herein are lipid nanoparticles comprising a cationic lipid, a dilinoleic cationic lipid, a phospholipid, a sterol, and a polyethylene glycol-lipid conjugate. In embodiments, the lipid nanoparticles comprise DOTAP, MC3, DSPC, cholesterol, and C16 PEG2000 ceramide. In embodiments, the lipid nanoparticles encapsulate a nucleic acid, such as RNA, siRNA, or mRNA. In embodiments, the nucleic acid are capable of hybridizing to a SARS coronavirus (e.g., SARS-CoV-2) target sequence.

Provided herein are lipid nanoparticles comprising about 30 mole % to about 45 mole % of a cationic lipid: about 10 mole % to about 30 mole % of a dilinoleic cationic lipid; about 5 mole % to about 15 mole % of a phospholipid; about 17 mole % to 30 mole % of a sterol; and about 1 mole % to about 4 mole % of a polyethylene glycol-lipid conjugate. In embodiments, the cationic lipid is DOTAP; the dilinoleic cationic lipid is MC3; the phospholipid is DSPC; the sterol is cholesterol; and the polyethylene glycol-conjugated lipid is C16 PEG2000 ceramide. In embodiments, the lipid nanoparticles encapsulate a nucleic acid, such as RNA, siRNA, or mRNA. In embodiments, the nucleic acid are capable of hybridizing to a SARS coronavirus (e.g., SARS-CoV-2) target sequence.

Provided herein are methods for treating a SARS coronavirus infection in a patient by administering an effective amount of the lipid nanoparticles having nucleic acids encapsuled therein described herein. In embodiments, the SARS coronavirus infection is SARS-CoV-2, SARS-CoV-1, or MERS-CoV.

Provided herein are methods for treating COVID-19 in a patient by administering an effective amount of the lipid nanoparticles described herein.

These and other embodiments of the disclosure are described herein.

BRIEF DESCRIPTION OF THE DRAWINGS

FIG. 1A: dmLNP-siRNA nanoparticle characteristics including size, polydispersity (PDI), surface charge (zeta potential), and siRNA encapsulation efficiency. FIG. 1B: dmLNP-siRNA biodistribution was determined in C57/BL6 mice that received DiD-labeled dmLNP-siRNA nanoparticles at 1 mg/kg siRNA dose or PBS vehicle control via retro-orbital (RO) route. 24 hours after injection, mice were euthanized and the lung, liver, and spleen were removed. Organs were imaged for DiD fluorescence using a LagoX small animal imaging machine at excitation and emission wavelength of 640 and 690 nm, respectively. FIG. 1C: quantitative analysis of DiD fluorescence in each organ.

FIG. 2A: average size and polydispersity index of each DOTAP formulation was determined by dynamic light scattering (DLS). Error bars represent the S.E.M. of 5 runs. FIG. 2B: average zeta potential reported in millivolts (mV) for each DOTAP formulation. Error bars represent the S.E.M. of 10 runs. FIG. 2C: siRNA encapsulation efficiency of each formulation was determined using the Quant-IT Ribogreen assay. FIG. 2D: representative transmission electron microscope (TEM) image of DOTAP 40 nanoparticle formulation.

FIG. 3A: size and polydispersity measurements were carried out using dynamic light scattering (DLS) on DOTAP40 and DOTAP40C LNP formulations after synthesis and after 9 months of storage at 4° C. Error bars represent the S.E.M. of 5 runs. FIG. 3B: retention of siRNAs in LNPs after 9 months of storage. Ribogreen quantification of encapsulated siRNA in LNPs was evaluated at day 0 and again 9 months post synthesis. % siRNA retention=(final encapsulated siRNA concentration)/(starting encapsulated siRNA concentration)*100. FIG. 3C: DOTAP40C LNPs carrying Lamin A/C siRNA stored at either 4° C. or room temperature for 6 days were dropped on NIH-3T3 cells at approximately 40 nM and incubated for 48 hours. RNA was then extracted and 10 ng of RNA was used in a Luna Universal One-Step RT-qPCR (New England BioLabs) to evaluate Lamin A/C expression. Error bars represent the S.E.M of triplicate wells. FIG. 3D: serum stability evaluation of dmLNP-siRNAs. 2.5 ug of dmLNP-siN367 or N367 siRNA alone were incubated in 50 ul of FBS (not heat inactivated) at 37° C. for 0, 10, 30, 60, 90, and 120 minutes as done in (PMID: 19023647). RNase free water was added up to 200 μL and RNA was subsequently extracted using phenol/chloroform (1:1 v/v) and centrifuged for at 14,000 rpm for 10 minutes at 4° C. The aqueous fraction was removed (approximately 25 μL), diluted 1/10, and electrophoresed on a non-denaturing 6% TBE polyacrylamide gel (Novex, Invitrogen) for 30 min at 200V. The gel was then stained with 2 μg/mL EtBr and images were acquired under 254 nm using an EZ Imager (Bio-Rad). Note: dmLNP is the updated name of the DOTAP40C formulation.

DETAILED DESCRIPTION

Definitions

Figure 1A:
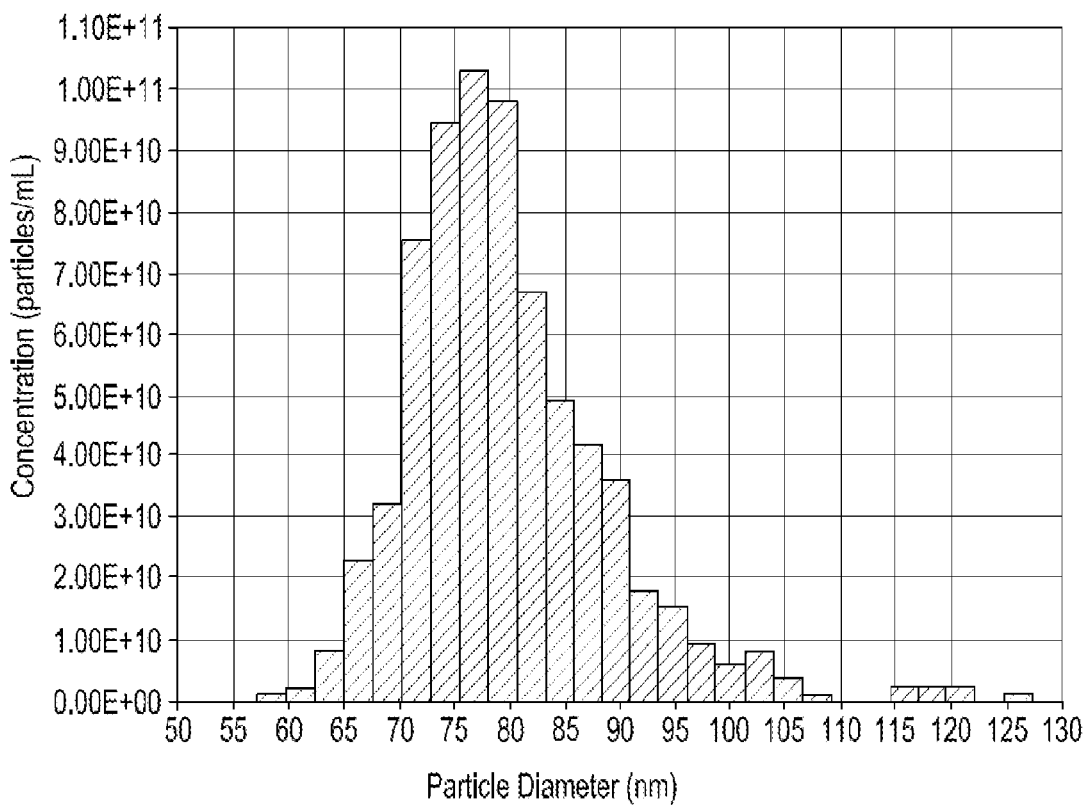
FIGS. 1A-1C show the nanoparticle size distribution of dmLNP-siRNA lipid nanoparticles determined using the qNano Gold tunable resistive pulse sensing device.

The abbreviations used herein have their conventional meaning within the chemical and biological arts. The chemical structures and formulae set forth herein are constructed according to the standard rules of chemical valency known in the chemical arts.

The term "lipid" refers to a group of organic compounds that include, but are not limited to, esters of fatty acids and are characterized by being insoluble in water, but soluble in many organic solvents.

The terms "lipid nanoparticle" and "stealth lipid nanoparticle" refer to a lipid formulation that can be used to deliver an active agent or therapeutic agent, such as a nucleic acid (e.g., RNA, sense RNA, antisense RNA, siRNA, mRNA), to a target site of interest (e.g., cell, tissue, organ, and the like). In embodiments, the lipid nanoparticle is typically formed from a cationic lipid, a non-cationic lipid, and a conjugated lipid that prevents aggregation of the particle. In other embodiments, the active agent or therapeutic agent, such as a nucleic acid (e.g., RNA, sense RNA, antisense RNA, siRNA, mRNA), may be encapsulated in the lipid portion of the particle, thereby protecting it from enzymatic degradation.

The term "SNALP" refers to a stable lipid nanoparticle comprising a nucleic acid. A SNALP represents a nanoparticle made from lipids (e.g., a cationic lipid, a non-cationic lipid, and a conjugated lipid), wherein the nucleic acid (e.g., RNA, sense RNA, antisense RNA, siRNA, mRNA) is fully encapsulated within the lipid. In embodiments, SNALP are useful for systemic applications, as they can exhibit extended circulation lifetimes following intravenous injection, they can accumulate at distal sites (e.g., sites physically separated from the administration site, such as the lungs), and they can mediate silencing of target gene expression at these distal sites. The nucleic acid (e.g., RNA, sense RNA, antisense RNA, siRNA, mRNA) may be complexed with a condensing agent and encapsulated within a SNALP as set forth, e.g., in WO 2000/03683.

"Lipid encapsulated" refers to a lipid particle that provides an active agent or therapeutic agent, such as a nucleic acid (e.g., RNA, sense RNA, antisense RNA, siRNA, mRNA), with full encapsulation, partial encapsulation, or both. In embodiments, the nucleic acid (e.g., RNA, sense RNA, antisense RNA, siRNA, mRNA) is fully encapsulated in the lipid particle (e.g., to form a SNALP or other nucleic acid-lipid particle). In embodiments, "lipid encapsulated" refers to a lipid particle that contains two to six different active agents or therapeutic agents, such as a nucleic acid (e.g., RNA, sense RNA, antisense RNA, siRNA, mRNA), with full encapsulation, partial encapsulation, or both. In embodiments, "lipid encapsulated" refers to a lipid particle that contains two to five different active agents or therapeutic agents, such as a nucleic acid (e.g., RNA, sense RNA, antisense RNA, siRNA, mRNA), with full encapsulation, partial encapsulation, or both. In embodiments, "lipid encapsulated" refers to a lipid particle that contains two to four different active agents or therapeutic agents, such as a nucleic acid (e.g., RNA, sense RNA, antisense RNA, siRNA, mRNA), with full encapsulation, partial encapsulation, or both. In embodiments, "lipid encapsulated" refers to a lipid particle that contains two or three different active agents or therapeutic agents, such as a nucleic acid (e.g., RNA, sense RNA, antisense RNA, siRNA, mRNA), with full encapsulation, partial encapsulation, or both. In embodiments, "lipid encapsulated" refers to a lipid particle that contains two different active agents or therapeutic agents, such as a nucleic acid (e.g., RNA, sense RNA, antisense RNA, siRNA, mRNA), with full encapsulation, partial encapsulation, or both. In embodiments, "lipid encapsulated" refers to a lipid particle that contains three different active agents or therapeutic agents, such as a nucleic acid (e.g., RNA, sense RNA, antisense RNA, siRNA, mRNA), with full encapsulation, partial encapsulation, or both. In embodiments, "lipid encapsulated" refers to a lipid particle that contains four different active agents or therapeutic agents, such as a nucleic acid (e.g., RNA, sense RNA, antisense RNA, siRNA, mRNA), with full encapsulation, partial encapsulation, or both.

The term "lipid conjugate" refers to a conjugated lipid that inhibits aggregation of lipid particles. Such lipid conjugates include PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., US Publication No. 2011/0313017), polyamide oligomers (e.g., ATTA-lipid conjugates), and mixtures thereof. Additional examples of POZ-lipid conjugates are described in WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In embodiments, non-ester containing linker moieties, such as amides or carbamates, are used.

In embodiments, the term "polyethylene glycol-lipid conjugate" or "PEG-lipid conjugate" refers to a polyethylene glycol having a molecular weight from about 500 Daltons to about 10,000 Daltons conjugated to a $C_{12}$-$C_{22}$ fatty acid lipid. In embodiments, a PEG-lipid conjugate is polyethylene glycol having a molecular weight from about 1,000 Daltons to about 6,000 Daltons conjugated to a $C_{12}$-$C_{22}$ fatty acid lipid. In embodiments, a PEG-lipid conjugate is polyethylene glycol having a molecular weight from about 2,000 Daltons to about 5,000 Daltons conjugated to a $C_{12}$-$C_{20}$ fatty acid lipid. In embodiments, a PEG-lipid conjugate is polyethylene glycol having a molecular weight from about 2,000 Daltons to about 5,000 Daltons conjugated to a $C_{12}$-$C_{18}$ fatty acid lipid. In embodiments, the PEG-lipid conjugate is N-palmitoyl-sphingosine-1-{succinyl[methoxy(polyethylene glycol)]} (C16 PEG ceramide), 1,2-dimyristoyl-rac-glycero-3-methoxypolyethylene glycol (DMG-PEG), 1,2-dipalmitoyl-sn-glycero-3-phosphoethanolamine-N-[azido (polyethylene glycol) (DPPE-PEG), 1,2-dipalmitoyl-rac-glycero-3-methylpolyoxyethylene (DPG-PEG), distearoyl-rac-glycerol(polyethylene glycol) (DSG-PEG), 1,2-distearoyl-sn-glycero-3-phosphoethanolamine-N-[amino (polyethylene glycol) (DSPE-PEG). In embodiments, the polyethylene glycol has an average molecular weight of about 2000 daltons (e.g., C16 PEG200 ceramide, DPPE-PEG2000, DPG-PEG2000, DSG-PEG2000, DSPE-PEG2000). The polyethylene glycol-lipid conjugate can optionally be in the form of a pharmaceutically acceptable salt (e.g., ammonium salt).

The term "C16 PEG2000 ceramide" refers to N-palmitoyl-sphingosine-1-{succinyl[methoxy(polyethylene glycol)2000]}, where 2000 refers to the average molecular weight of the polyethylene glycol.

The term "average molecular weight" refers to the average molecular weight of a polymer sample that is determined by a technique known in the art, such as gel permeation chromatography, light-scattering measurements and viscosity measurements. In embodiments, the average molecular weight is the number average molecular weight which is defined as the total weight of polymer divided by the total number of molecules.

The term "amphipathic lipid" refers, in part, to any material wherein the hydrophobic portion of the lipid orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include long-chain saturated and unsaturated aliphatic hydrocarbon groups and such groups substituted by one or more aromatic, cycloaliphatic, or heterocyclic group(s). Examples of amphipathic compounds include phospholipids, aminolipids, and sphingolipids. Exemplary phospholipids include dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine (MMPE), dimethyl-phosphatidylethanolamine (DMPE), dielaidoyl-phosphatidylethanolamine (DEPE), stearoyloleoyl-phosphatidylethanolamine (SOPE), egg phosphatidylcholine (EPC), hydrogenated soy phosphatidylcholine (HSPC), and mixtures thereof. In embodiments, DSPC is 1,2-distearoyl-sn-glycero-3-phosphocholine. Other compounds lacking in phosphorus, such as sphingolipid, glycosphingolipid families, diacylglycerols, and β-acyloxy-acids, are also within the group designated as amphipathic lipids. Additionally, the amphipathic lipids can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

The term "hydrophobic lipid" refers to compounds having apolar groups that include long-chain saturated and unsaturated aliphatic hydrocarbon groups and such groups optionally substituted by one or more aromatic, cycloaliphatic, or heterocyclic group(s). Suitable examples include diacylglycerol, dialkylglycerol, N—N-dialkylamino, 1,2-diacyloxy-3-aminopropane, and 1,2-dialkyl-3-aminopropane.

A "cationic lipid" is a positively charged lipid that has the ability to form aggregate complexes with anionic nucleic acids such as DNA or RNA. In embodiments, the term "cationic lipid" does not include a "dilinoleic cationic lipid" as that term is defined herein (i.e., a "non-dilinoleic cationic lipid"). Exemplary cationic lipids include N,N-dioleyl-N,N-dimethylammonium chloride (DODAC), 1,2-dioleyloxy-N, N-dimethylaminopropane (DODMA), 1,2-distearyloxy-N, N-dimethylaminopropane (DSDMA), N-(1-(2,3-dioleyloxy) propyl)-N,N,N-trimethylammonium chloride (DOTMA), N,N-distearyl-N,N-dimethylammonium bromide (DDAB), 1,2-dioleoyloxy-3-(trimethylammonium)propane (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioley-loxy-N-[2(spermine-carboxamido)ethyl]-N,N-dimethyl-1-propanaminium-trifluoroacetate (DOSPA), dioctadecylamidoglycyl spermine (DOGS), 3-dimethyl-amino-2-(cholest-5-en-3-beta-oxybutan-4-oxy)-1-(cis,cis-9, 12-octadecadienoxy)-propane (CLinDMA), 2-[5'-(cholest-5-en-3-beta-oxy)-3'-oxapentoxy)-3-dimethy-1-(cis,cis-9',1-2'-octadecadienoxy)-propane (CpLinDMA), N,N-dimethyl-3,4-dioleyloxybenzylamine (DMOBA), 1,2-N,N'-dioleylcarbamyl-3-dimethylaminopropane (DOcarbDAP), 3-(N,N-dioleylamino)-1,2-propanedio (DOAP), and 1,1'-((2-(4-(2-((2-bis(2-hydroxydodecyl)amino)ethyl) (C12-200).

As used herein, the term "dilinoleic cationic lipid" refers to any cationic lipid containing two linoleic moieties (e.g., two C18 moities optionally containing 1, 2, or 3 —CH=CH— groups). In embodiments, a dilinoleic cationic moiety comprises two —(CH₂)₈CH=CHCH₂CH=CH(CH₂)₄CH₃ moieties. Exemplary dilinoleic cationic lipids include MC3, MC3 derivatives, 1,2-dilinoleyloxy-N,N-dimethylaminopropane (DLinDMA), 2,2-dilinoleyl-4-(2-dimethylaminoethyl)-[1, 3]-dioxolane (DLin-KC2-DMA), 2,2-dilinoleyl-4-(3-dim-ethylaminopropyl)-[1,3]-dioxolane (DLin-K-3-DMA), 2,2-dilinoleyl-4-(4-dimethylaminobutyl)-[1,3]-dioxolane (DLin-KC4-DMA), 2,2-dilinoleyl-5-dimethylaminomethyl-[1,3]-dioxane (DLin-K6-DMA), 2,2-dilinoleyl-4-N-meth-ylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)ac-etoxypropane (DLin-DAC), 1,2-dilinoleyoxy-3-mor-pholinopropane (DLin-MA), 1,2-dilinoleoyl-3-dimethyl-aminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-meth-ylpiperazino)propane (DLin-MPZ), 3-(N,N-dilinoley-lamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), and 1,2-N,N'-dilinoleylcarbamyl-3-dimethylaminopropane (DLincarbDAP).

The term "MC3" or "Dlin-MC3-DMA" refer to dilinol-eyl-methyl-4-dimethylaminobutyrate. In embodiments, "MC3" refers to heptatriaconta-6,9,28,31-tetraen-19-yl 4-(dimethylamino)butanoate. In embodiments, "MC3" refers to (6Z,9Z,28Z,31Z)-heptatriaconta-6,9,28,31-tetraen-19-yl-4-(dimethylamino)butanoate.

The term "MC3 derivative" refers to derivatives of MC3 such as those described in US Publication No. 2017/0151333. Exemplary MC3 derivatives include LenMC3, γ-LenMC3, MC3 ether, MC4 ether, MC3MC, MC2C, MC2MC, MC3 thioester, MC3 alkyne, MC3 amide, and other compounds described in US Publication No. 2017/0151333.

The term "non-lamellar morphology" refer to a non-bilayer structure. The non-bilayer morphology can include, for example, three dimensional tubes, rods, cubic symme-tries, etc. The non-lamellar morphology (i.e., non-bilayer structure) of the lipid particles can be determined using analytical techniques including Cryo-Transmission Electron Microscopy ("Cryo-TEM"), Differential Scanning calorim-etry ("DSC"), and X-Ray Diffraction.

The term "a plurality of nucleic acid-lipid particles" refers to at least 2 particles, more preferably more than 10, $10^2$, $10^3$, $10^4$, $10^5$, $10^6$ or more particles (or any fraction thereof or range therein). In embodiments, the plurality of nucleic acid-lipid particles includes 50-100, 50-200, 50-300, 50-400, 50-500, 50-600, 50-700, 50-800, 50-900, 50-1000, 50-1100, 50-1200, 50-1300, 50-1400, 50-1500, 50-1600, 50-1700, 50-1800, 50-1900, 50-2000, 50-2500, 50-3000, 50-3500, 50-4000, 50-4500, 50-5000, 50-5500, 50-6000, 50-6500, 50-7000, 50-7500, 50-8000, 50-8500, 50-9000, 50-9500, 50-10,000 or more particles.

The term "organic lipid solution" refers to a composition comprising in whole, or in part, an organic solvent having a lipid.

"Nucleic acid" refers to nucleotides (e.g., deoxyribo-nucleotides or ribonucleotides) and polymers thereof in either single-, double- or multiple-stranded form, or comple-ments thereof. The terms "polynucleotide," "oligonucle-otide," "oligo" or the like refer, in the usual and customary sense, to a linear sequence of nucleotides. The term "nucleo-tide" refers, in the usual and customary sense, to a single unit of a polynucleotide, i.e., a monomer. Nucleotides can be ribonucleotides, deoxyribonucleotides, or modified versions thereof. Examples of nucleic acids contemplated herein include single and double stranded DNA, single and double stranded RNA, and hybrid molecules having mixtures of single and double stranded DNA and RNA. Examples of nucleic acids contemplated herein include any types of RNA (e.g., antisense RNA, mRNA, siRNA, miRNA, shRNA, guide RNA, dicer substrate RNA, dicer substrate siRNAs (dsiRNAs) (dsiRNA are cleaved by the RNase III class endoribonuclease dicer into 21-23 base duplexes having 2-base 3'-overhangs siRNA), and any type of DNA, genomic DNA, plasmid DNA, minicircle DNA, minigene, and any fragments thereof. The term "duplex" in the context of nucleic acids refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phos-phodiester derivatives including, e.g., phosphoramidate, phosphorodiamidate, phosphorothioate (also known as phosphorothioate having double bonded sulfur replacing oxygen in the phosphate), phosphorodithioate, phosphono-carboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as 2'O-methyl, 2'O-methoxy-ethoxy, 2'fluoro, 5-methyl cytidine or pseudouridine; and peptide nucleic acid backbones and linkages. Other analog nucleic acids include those with positive backbones; non-ionic backbones, modified sugars (e.g., deoxyribose), and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of natu-rally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The term "plasmid" or "expression vector" refers to a nucleic acid molecule that encodes for genes and/or regu-latory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

A "minigene" is a minimal gene fragment that includes an exon and the control regions necessary for the gene to express itself in the same way as a wild type gene fragment. This is a minigene in its most basic sense. More complex minigenes can be constructed containing multiple exons and intron(s).

Nucleic acids, including e.g., nucleic acids with a phos-phothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is comple-mentary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, Scientific American, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In embodiments, the antisense nucleic acid hybridizes to the target nucleic acid in vitro. In embodiments, the antisense nucleic acid hybridizes to the target nucleic acid in a cell. In embodiments, the antisense nucleic acid hybridizes to the target nucleic acid in an organism. In embodiments, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and anomeric sugar-phosphate, backbone-modified nucleotides.

In the cell, the antisense nucleic acids hybridize to the corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, Anal. Biochem., 172:289, (1988)). Further, antisense mol-ecules which bind directly to the DNA may be used. Antisense nucleic acids may be single or double stranded nucleic acids. Non-limiting examples of antisense nucleic acids include small interfering RNAs (siRNAs)(including their derivatives or pre-cursors, such as nucleotide analogs), short hairpin RNAs (shRNA), micro RNAs (miRNA), saR-NAs (small activating RNAs) and small nucleolar RNAs (snoRNA) or certain of their derivatives or pre-cursors.

"siRNA" and "small interfering RNA" as provided herein refers to a double-stranded or single-stranded ribonucleic acid that has the ability to reduce or inhibit expression of a gene or the activity of a target nucleic acid (e.g., a single-stranded or double-stranded RNA or a single-stranded or doubles-stranded DNA) when expressed in the same cell as the gene or target gene. Where the siRNA is a double-stranded RNA, the complementary portions of the ribo-nucleic acid that hybridize to form the double stranded molecule typically have substantial or complete identity. In embodiments, an siRNA is a nucleic acid that has substantial or complete identity to a target RNA and forms a double stranded siRNA. In embodiments, the siRNA inhibits gene expression by interacting with a complementary cellular RNA thereby interfering with the endogenous behavior of the complementary cellular RNA. Typically, the siRNA is about 15-50 nucleotides in length (e.g., each complementary sequence of the double stranded siRNA is 15-50 nucleotides in length, and the double stranded siRNA is about 15-50 base pairs in length). The siRNAs provided herein regulate expression of a target gene or activity of a target nucleic by hybridizing to the mRNA of the gene or by hybridizing to the promoter of the target nucleic or the target nucleic acid itself. Where the siRNA hybridizes to a promoter of a gene thereby modulating the expression of said gene, the siRNA may be referred to as "antigen RNA" or "agRNA." In embodiments, the nucleic acid sequences provided herein are siRNA.

The terms "short hairpin RNA" or "shRNA" refer to an anti-sense ribonucleic acid sequence as defined above, which is capable of binding (hybridizing) and inhibiting activity of a target RNA (e.g., mRNA), which it is partially or entirely complementary to. shRNA may be single stranded nucleic acid sequences having a secondary or tertiary structure and, thus, may be able to fold into diverse and intricate molecular structures such as stem-loop struc-tures.

"Dicer-substrate small interfering RNA" or "dsiRNA" are RNA duplexes that are processed by the Dicer enzyme into 25 to 30 nucleotides in length, and are effective triggers of RNA interference.

"Hybridize" and "hybridization" refer to the pairing of complementary (including partially complementary) nucleic acid strands. Hybridization and the strength of hybridization (e.g., the strength of the association between nucleic acid strands) is impacted by factors known in the art including the degree of complementarity between the nucleic acid, stringency of the conditions involved affected by such conditions as the concentration of salts, the melting temperature (Tm) of the formed hybrid, the presence of other components, the molarity of the hybridizing strands and the G:C content of the nucleic acid strands. When one nucleic acid is said to "hybridize" to another nucleic acid, it means that there is some complementarity between the two nucleic acids or that the two nucleic acids form a hybrid under high or low stringency conditions.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than thermal melting point $(T_m)$ for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary hybridization conditions can be as follows: 50% formamide, 5×SSC, and 1% SDS, incubating at 42° C., or 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For PCR amplification, a temperature of about 62° C. is typical, although high stringency annealing temperatures can range from about 50° C. to about 65° C. depending on the primer length and specificity. Typical cycle conditions for both high and low stringency amplifications include a denaturation phase of 90° C.-95° C. for 30 seconds to 2 minutes, an annealing phase lasting 30 seconds to 2 minutes, and an extension phase of about 72° C. for 1-2 min. Protocols and guidelines for low and high stringency amplification reactions are provided, e.g., in Innis et al., PCR Protocols, A Guide to Methods and Applications, Academic Press, Inc. N.Y. (1990).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (e.g., http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In embodiments, the nucleic acids described herein are isolated nucleic acids.

The term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor.

In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "target gene" refers to any nucleic acid sequence which contains an identified genes or a target region within a gene, including intergenic regions, non-coding regions, untranscribed regions, introns, exons, and transgenes. The target gene (or a target site within the gene) can be a gene derived from a cell, an endogenous gene, a transgene, or exogenous genes such as genes of a pathogen, for example a virus, which is present in the cell after infection thereof. The cell containing the target gene can be derived from or contained in any organism.

The terms "treating" or "treatment" refers to any indicia of success in therapy or amelioration of a disease, pathology or condition, including any objective or subjective parameter such as abatement; remission; diminishing of symptoms or making the pathology or condition more tolerable to the patient; slowing in the rate of degeneration or decline; making the final point of degeneration less debilitating;

improving a patient's physical well-being. The treatment or amelioration of symptoms can be based on objective or subjective parameters; including the results of a physical examination. The term "treating" and conjugations thereof, may include prevention of a pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent (e.g., nucleic acids, antisense RNA, siRNA, mRNA). The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment.

"Patient" or "subject in need thereof" refers to a living organism. Non-limiting examples include humans, other mammals, dogs, cats, bovines, rats, mice, dogs, monkeys, goat, sheep, cows, and other non-mammalian animals. In embodiments, a patient is a cat or a dog. In embodiments, a patient is a primate. In embodiments, a patient is human.

A "effective amount" as used herein, is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). In these methods, the effective amount of the nucleic acid (RNA, antisense RNA, siRNA, mRNA) described herein is an amount effective to accomplish the stated purpose of the method. An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "therapeutically effective amount," as used herein, refers to that amount of therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. For any compound described herein, therapeutically effective amount can be initially determined from cell culture assays. Target concentrations will be those concentrations of active compound(s) that are capable of achieving the methods described herein, as measured using the methods described herein or known in the art. As is in the art, therapeutically effective amounts for use in humans can also be determined from animal models. For example, a dose for humans can be formulated to achieve a concentration that has been found to be effective in animals.

The term "administering" means intranasal administration, inhalation administration, oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. In embodiments, administering does not include administration of any active agent other than the nucleic acid. In embodiments, administration is intranasal. In embodiments, administration is intravenous. In embodiments, administration is intranasal administration of lipid nanoparticles. In embodiments, administration is intravenous administration of lipid nanoparticles.

The singular terms "a," "an," and "the" include the plural reference unless the context clearly indicates otherwise.

The term "and/or" refers to either or both. For example, "SEQ ID NO:1 and/or SEQ ID NO:3" means: (i) SEQ ID NO:1, (ii) SEQ ID NO:3, or (iii) SEQ ID NO:1 and SEQ ID NO:3. In embodiments, an antisense strand and a sense strand can be hybridized.

Lipid Nanoparticles

Provided herein are lipid nanoparticles comprising a cationic lipid, a dilinoleic cationic lipid, a phospholipid, a sterol, and a polyethylene glycol-lipid conjugate (PEG-lipid conjugate). In embodiments, the cationic lipid is DOTAP, DODAC, DODMA, DSDMA, DOTMA, DDAB, DC-Chol, DMRIE, DOSPA, DOGS, CLinDMA, CpLinDMA, DMOBA, DOcarbDAP, DOAP, C12-200, or a mixture of two or more thereof, or a mixture of two or more thereof. In embodiments, the cationic lipid is DOTAP. In embodiments, the dilinoleic cationic lipid is MC3, an MC3 derivative, DLinDMA, DLin-K-C2-DMA, DLin-K-C3-DMA, DLin-K-

C4-DMA, DLin-K6-DMA, DLin-K-MPZ, DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DLin-EG-DMA, DLincarbDAP, or a mixture of two or more thereof. In embodiments, the dilinoleic cationic lipid is MC3, Dlin-KC2-DMA, or a combination thereof. In embodiments, the dilinoleic cationic lipid is MC3. In embodiments, the dilinoleic cationic lipid is Dlin-KC2-DMA. In embodiments, the phospholipid is DSPC, DPPC, DOPE, POPC, POPE, POPG, DPPE, DMPE, DSPE, MMPE, DMPE, DEPE, SOPE, EPC, HSPC, or a mixture of two or more thereof. In embodiments, the phospholipid is DSPC. In embodiments, the sterol is cholesterol, cholestanol, cholestanone, cholestenone, coprostanol, cholesteryl-2'-hydroxyethyl ether, cholesteryl-4'-hydroxybutyl ether, or a mixture of two or more thereof. In embodiments, the sterol is cholesterol. In embodiments, the PEG-lipid conjugate is a polyethylene glycol having a molecular weight from about 1,000 Daltons to about 6,000 Daltons conjugated to a $C_{12}$-$C_{22}$ fatty acid lipid. In embodiments, the PEG-lipid conjugate is C16 PEG ceramide, DMG-PEG, DPPE-PEG, DPG-PEG, DSG-PEG, DSPE-PEG, or a mixture of two or more thereof. In embodiments, the PEG-lipid conjugate is C16 PEG ceramide, DMG-PEG, DPPE-PEG, DPG-PEG, DSG-PEG, DSPE-PEG, or a mixture of two or more thereof, wherein the PEG in each compound has a molecular weight of about 2,000 Daltons. In embodiments, the PEG-lipid conjugate is C16 PEG ceramide. In embodiments, the PEG-lipid conjugate is C16 PEG200 ceramide (i.e., wherein PEG2000 refers to PEG having a molecular weight of about 2,000 Daltons). In embodiments, the cationic lipid is DOTAP, the dilinoleic cationic lipid is MC3, the phospholipid is DSPC, the sterol is cholesterol, and the PEG-lipid conjugate is C16 PEG200 ceramide. In embodiments, the lipid nanoparticles are a plurality of lipid nanoparticles. In embodiments, DSPC is distearoylphosphatidylcholine. In embodiments, DSPC is 1,2-distearoyl-sn-glycero-3-phosphocholine.

Provided herein are lipid nanoparticles comprising: (i) about 30 mole % to about 45 mole % of a cationic lipid; (ii) about 10 mole % to about 30 mole % of a dilinoleic cationic lipid; (iii) about 5 mole % to about 15 mole % of a phospholipid; (iv) about 15 mole % to about 30 mole % of a sterol; and (v) about 1 mole % to about 3.5 mole % of a PEG-lipid conjugate. In embodiments, the lipid nanoparticles comprise: (i) about 35 mole % to about 45 mole % of a cationic lipid; (ii) about 20 mole % to about 30 mole % of a dilinoleic cationic lipid; (iii) about 5 mole % to about 15 mole % of a phospholipid; (iv) about 17 mole % to about 27 mole % of a sterol; and (v) about 1 mole % to about 4 mole % of a PEG-lipid conjugate. In embodiments, the lipid nanoparticles comprise: (i) about 36 mole % to about 44 mole % of a cationic lipid; (ii) about 21 mole % to about 29 mole % of a dilinoleic cationic lipid; (iii) about 6 mole % to about 14 mole % of a phospholipid; (iv) about 18 mole % to about 26 mole % of a sterol; and (v) about 1 mole % to about 4 mole % of a PEG-lipid conjugate. In embodiments, the lipid nanoparticles comprise: (i) about 37 mole % to about 43 mole % of a cationic lipid; (ii) about 22 mole % to about 28 mole % of a dilinoleic cationic lipid; (iii) about 7 mole % to about 13 mole % of a phospholipid; (iv) about 19 mole % to about 25 mole % of a sterol; and (v) about 1.5 mole % to about 4 mole % of a PEG-lipid conjugate. In embodiments, the lipid nanoparticles comprise: (i) about 38 mole % to about 42 mole % of a cationic lipid; (ii) about 23 mole % to about 27 mole % of a dilinoleic cationic lipid; (iii) about 8 mole % to about 12 mole % of a phospholipid; (iv) about 20 mole % to about 24 mole % of a sterol; and (v) about 2 mole % to about 4 mole % of a PEG-lipid conjugate. In embodiments, the lipid nanoparticles comprise: (i) about 39 mole % to about 41 mole % of a cationic lipid; (ii) about 24 mole % to about 26 mole % of a dilinoleic cationic lipid; (iii) about 9 mole % to about 11 mole % of a phospholipid; (iv) about 21 mole % to about 23 mole % of a sterol; and (v) about 2.5 mole % to about 3.5 mole % of a PEG-lipid conjugate. In embodiments, the lipid nanoparticles comprise: (i) about 40 mole % of a cationic lipid; (ii) about 25 mole % of a dilinoleic cationic lipid; (iii) about 10 mole % of a phospholipid; (iv) about 22 mole % of a sterol; and (v) about 3 mole % of a PEG-lipid conjugate. In embodiments, the cationic lipid is DOTAP, DODAC, DODMA, DSDMA, DOTMA, DDAB, DC-Chol, DMRIE, DOSPA, DOGS, CLinDMA, CpLinDMA, DMOBA, DOcarbDAP, DOAP, C12-200, or a mixture of two or more thereof, or a mixture of two or more thereof. In embodiments, the cationic lipid is DOTAP. In embodiments, the dilinoleic cationic lipid is MC3, an MC3 derivative, DLinDMA, DLin-K-C2-DMA, DLin-K-C3-DMA, DLin-K-C4-DMA, DLin-K6-DMA, DLin-K-MPZ, DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DLin-EG-DMA, DLincarbDAP, or a mixture of two or more thereof. In embodiments, the dilinoleic cationic lipid is MC3, Dlin-KC2-DMA, or a combination thereof. In embodiments, the dilinoleic cationic lipid is MC3. In embodiments, the dilinoleic cationic lipid is Dlin-KC2-DMA. In embodiments, the phospholipid is DSPC, DPPC, DOPE, POPC, POPE, POPG, DPPE, DMPE, DSPE, MMPE, DMPE, DEPE, SOPE, EPC, HSPC, or a mixture of two or more thereof. In embodiments, the phospholipid is DSPC. In embodiments, the sterol is cholesterol, cholestanol, cholestanone, cholestenone, coprostanol, cholesteryl-2'-hydroxyethyl ether, cholesteryl-4'-hydroxybutyl ether, or a mixture of two or more thereof. In embodiments, the sterol is cholesterol. In embodiments, the PEG-lipid conjugate is a polyethylene glycol having a molecular weight from about 1,000 Daltons to about 6,000 Daltons conjugated to a $C_{12}$-$C_{22}$ fatty acid lipid. In embodiments, the PEG-lipid conjugate is C16 PEG ceramide, DMG-PEG, DPPE-PEG, DPG-PEG, DSG-PEG, DSPE-PEG, or a mixture of two or more thereof. In embodiments, the PEG-lipid conjugate is C16 PEG ceramide, DMG-PEG, DPPE-PEG, DPG-PEG, DSG-PEG, DSPE-PEG, or a mixture of two or more thereof, wherein the PEG in each compound has a molecular weight of about 2,000 Daltons. In embodiments, the PEG-lipid conjugate is C16 PEG ceramide. In embodiments, the PEG-lipid conjugate is C16 PEG200 ceramide (i.e., wherein PEG2000 refers to PEG having a molecular weight of about 2,000 Daltons). In embodiments, the cationic lipid is DOTAP, the dilinoleic cationic lipid is MC3, the phospholipid is DSPC, the sterol is cholesterol, and the PEG-lipid conjugate is C16 PEG200 ceramide. In embodiments, the lipid nanoparticles are a plurality of lipid nanoparticles.

Provided herein are lipid nanoparticles comprising: (i) 30 mole %±25% of a cationic lipid; (ii) 20 mole %±25% of a dilinoleic cationic lipid; (iii) 10 mole %±25% of a phospholipid; (iv) 37 mole %±25% of a sterol; and (v) 3 mole %±25% of a PEG-lipid conjugate. In embodiments, the lipid nanoparticles comprise: (i) 30 mole %±20% of a cationic lipid; (ii) 20 mole % 20% of a dilinoleic cationic lipid; (iii) 10 mole % 20% of a phospholipid; (iv) 37 mole %±20% of a sterol; and (v) 3 mole %±20% of a PEG-lipid conjugate. In embodiments, the lipid nanoparticles comprise: (i) 30 mole %±15% of a cationic lipid; (ii) 20 mole %±15% of a dilinoleic cationic lipid; (iii) 10 mole %±15% of a phospholipid; (iv) 37 mole %±15% of a sterol; and (v) 3 mole %±15% of a PEG-lipid conjugate. In embodiments, the lipid nanoparticles comprise: (i) 30 mole %±10% of a cationic lipid; (ii) 20 mole % 10% of a dilinoleic cationic lipid; (iii) 10 mole % 10% of a phospholipid; (iv) 37 mole %±10% of a sterol; and (v) 3 mole %±10% of a PEG-lipid conjugate. In embodiments, the lipid nanoparticles comprise: (i) 30 mole %±5% of a cationic lipid; (ii) 20 mole %±5% of a dilinoleic cationic lipid; (iii) 10 mole %±5% of a phospholipid; (iv) 37 mole %±5% of a sterol; and (v) 3 mole %±5% of a PEG-lipid conjugate. In embodiments, the lipid nanoparticles comprise: (i) about 30 mole % of a cationic lipid; (ii) about 20 mole % of a dilinoleic cationic lipid; (iii) about 10 mole % of a phospholipid; (iv) about 37 mole % of a sterol; and (v) about 3 mole % of a PEG-lipid conjugate. In embodiments, the cationic lipid is DOTAP, DODAC, DODMA, DSDMA, DOTMA, DDAB, DC-Chol, DMRIE, DOSPA, DOGS, CLinDMA, CpLinDMA, DMOBA, DOcarbDAP, DOAP, C12-200, or a mixture of two or more thereof, or a mixture of two or more thereof. In embodiments, the cationic lipid is DOTAP. In embodiments, the dilinoleic cationic lipid is MC3, an MC3 derivative, DLinDMA, DLin-K-C2-DMA, DLin-K-C3-DMA, DLin-K-C4-DMA, DLin-K6-DMA, DLin-K-MPZ, DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DLin-EG-DMA, DLincarbDAP, or a mixture of two or more thereof. In embodiments, the dilinoleic cationic lipid is MC3, Dlin-KC2-DMA, or a combination thereof. In embodiments, the dilinoleic cationic lipid is MC3. In embodiments, the dilinoleic cationic lipid is Dlin-KC2-DMA. In embodiments, the phospholipid is DSPC, DPPC, DOPE, POPC, POPE, POPG, DPPE, DMPE, DSPE, MMPE, DMPE, DEPE, SOPE, EPC, HSPC, or a mixture of two or more thereof. In embodiments, the phospholipid is DSPC. In embodiments, the sterol is cholesterol, cholestanol, cholestanone, cholestenone, coprostanol, cholesteryl-2'-hydroxyethyl ether, cholesteryl-4'-hydroxybutyl ether, or a mixture of two or more thereof. In embodiments, the sterol is cholesterol. In embodiments, the PEG-lipid conjugate is a polyethylene glycol having a molecular weight from about 1,000 Daltons to about 6,000 Daltons conjugated to a $C_{12}$-$C_{22}$ fatty acid lipid. In embodiments, the PEG-lipid conjugate is C16 PEG ceramide, DMG-PEG, DPPE-PEG, DPG-PEG, DSG-PEG, DSPE-PEG, or a mixture of two or more thereof. In embodiments, the PEG-lipid conjugate is C16 PEG ceramide, DMG-PEG, DPPE-PEG, DPG-PEG, DSG-PEG, DSPE-PEG, or a mixture of two or more thereof, wherein the PEG in each compound has a molecular weight of about 2,000 Daltons. In embodiments, the PEG-lipid conjugate is C16 PEG ceramide. In embodiments, the PEG-lipid conjugate is C16 PEG200 ceramide (i.e., wherein PEG2000 refers to PEG having a molecular weight of about 2,000 Daltons). In embodiments, the cationic lipid is DOTAP, the dilinoleic cationic lipid is MC3, the phospholipid is DSPC, the sterol is cholesterol, and the PEG-lipid conjugate is C16 PEG200 ceramide. In embodiments, the lipid nanoparticles are a plurality of lipid nanoparticles.

Provided herein are lipid nanoparticles comprising: (i) 35 mole %±25% of a cationic lipid; (ii) 15 mole %±25% of a dilinoleic cationic lipid; (iii) 10 mole %±25% of a phospholipid; (iv) 37 mole %±25% of a sterol; and (v) 3 mole %±25% of a PEG-lipid conjugate. In embodiments, the lipid nanoparticles comprise: (i) 35 mole %±20% of a cationic lipid; (ii) 15 mole % 20% of a dilinoleic cationic lipid; (iii) 10 mole % 20% of a phospholipid; (iv) 37 mole %±20% of a sterol; and (v) 3 mole %±20% of a PEG-lipid conjugate. In embodiments, the lipid nanoparticles comprise: (i) 35 mole %±15% of a cationic lipid; (ii) 15 mole %±15% of a dilinoleic cationic lipid; (iii) 10 mole %±15% of a phospholipid; (iv) 37 mole %±15% of a sterol; and (v) 3 mole %±15% of a PEG-lipid conjugate. In embodiments, the lipid nanoparticles comprise: (i) 35 mole %±10% of a cationic lipid; (ii) 15 mole % 10% of a dilinoleic cationic lipid; (iii) 10 mole % 10% of a phospholipid; (iv) 37 mole %±10% of a sterol; and (v) 3 mole %±10% of a PEG-lipid conjugate. In embodiments, the lipid nanoparticles comprise: (i) 35 mole %±5% of a cationic lipid; (ii) 15 mole %±5% of a dilinoleic cationic lipid; (iii) 10 mole %±5% of a phospholipid; (iv) 37 mole %±5% of a sterol; and (v) 3 mole %±5% of a PEG-lipid conjugate. In embodiments, the lipid nanoparticles comprise: (i) about 35 mole % of a cationic lipid; (ii) about 15 mole % of a dilinoleic cationic lipid; (iii) about 10 mole % of a phospholipid; (iv) about 37 mole % of a sterol; and (v) about 3 mole % of a PEG-lipid conjugate. In embodiments, the cationic lipid is DOTAP, DODAC, DODMA, DSDMA, DOTMA, DDAB, DC-Chol, DMRIE, DOSPA, DOGS, CLinDMA, CpLinDMA, DMOBA, DOcarbDAP, DOAP, C12-200, or a mixture of two or more thereof, or a mixture of two or more thereof. In embodiments, the cationic lipid is DOTAP. In embodiments, the dilinoleic cationic lipid is MC3, an MC3 derivative, DLinDMA, DLin-K-C2-DMA, DLin-K-C3-DMA, DLin-K-C4-DMA, DLin-K6-DMA, DLin-K-MPZ, DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DLin-EG-DMA, DLincarbDAP, or a mixture of two or more thereof. In embodiments, the dilinoleic cationic lipid is MC3, Dlin-KC2-DMA, or a combination thereof. In embodiments, the dilinoleic cationic lipid is MC3. In embodiments, the dilinoleic cationic lipid is Dlin-KC2-DMA. In embodiments, the phospholipid is DSPC, DPPC, DOPE, POPC, POPE, POPG, DPPE, DMPE, DSPE, MMPE, DMPE, DEPE, SOPE, EPC, HSPC, or a mixture of two or more thereof. In embodiments, the phospholipid is DSPC. In embodiments, the sterol is cholesterol, cholestanol, cholestanone, cholestenone, coprostanol, cholesteryl-2'-hydroxyethyl ether, cholesteryl-4'-hydroxybutyl ether, or a mixture of two or more thereof. In embodiments, the sterol is cholesterol. In embodiments, the PEG-lipid conjugate is a polyethylene glycol having a molecular weight from about 1,000 Daltons to about 6,000 Daltons conjugated to a $C_{12}$-$C_{22}$ fatty acid lipid. In embodiments, the PEG-lipid conjugate is C16 PEG ceramide, DMG-PEG, DPPE-PEG, DPG-PEG, DSG-PEG, DSPE-PEG, or a mixture of two or more thereof. In embodiments, the PEG-lipid conjugate is C16 PEG ceramide, DMG-PEG, DPPE-PEG, DPG-PEG, DSG-PEG, DSPE-PEG, or a mixture of two or more thereof, wherein the PEG in each compound has a molecular weight of about 2,000 Daltons. In embodiments, the PEG-lipid conjugate is C16 PEG ceramide. In embodiments, the PEG-lipid conjugate is C16 PEG200 ceramide (i.e., wherein PEG2000 refers to PEG having a molecular weight of about 2,000 Daltons). In embodiments, the cationic lipid is DOTAP, the dilinoleic cationic lipid is MC3, the phospholipid is DSPC, the sterol is cholesterol, and the PEG-lipid conjugate is C16 PEG200 ceramide. In embodiments, the lipid nanoparticles are a plurality of lipid nanoparticles.

Provided herein are lipid nanoparticles comprising: (i) 40 mole %±25% of a cationic lipid; (ii) 10 mole %±25% of a dilinoleic cationic lipid; (iii) 10 mole %±25% of a phospholipid; (iv) 37 mole %±25% of a sterol; and (v) 3 mole % of ±25% a PEG-lipid conjugate. In embodiments, the lipid nanoparticles comprise: (i) 40 mole %±20% of a cationic lipid; (ii) 10 mole %±20% of a dilinoleic cationic lipid; (iii) 10 mole %±20% of a phospholipid; (iv) 37 mole %±20% of a sterol; and (v) 3 mole %±20% of a PEG-lipid conjugate. In embodiments, the lipid nanoparticles comprise: (i) 40 mole %±15% of a cationic lipid; (ii) 10 mole %±15% of a dilinoleic cationic lipid; (iii) 10 mole %±15% of a phospholipid; (iv) 37 mole %±15% of a sterol; and (v) 3 mole %±15% of a PEG-lipid conjugate. In embodiments, the lipid nanoparticles comprise: (i) 40 mole %±10% of a cationic lipid; (ii) 10 mole % 10% of a dilinoleic cationic lipid; (iii) 10 mole % 10% of a phospholipid; (iv) 37 mole %±10% of a sterol; and (v) 3 mole %±10% of a PEG-lipid conjugate. In embodiments, the lipid nanoparticles comprise: (i) 40 mole %±5% of a cationic lipid; (ii) 10 mole %±5% of a dilinoleic cationic lipid; (iii) 10 mole %±5% of a phospholipid; (iv) 37 mole %±5% of a sterol; and (v) 3 mole %±5% of a PEG-lipid conjugate. In embodiments, the lipid nanoparticles comprise: (i) about 40 mole % of a cationic lipid; (ii) about 10 mole % of a dilinoleic cationic lipid; (iii) about 10 mole % of a phospholipid; (iv) about 37 mole % of a sterol; and (v) about 3 mole % of a PEG-lipid conjugate. In embodiments, the cationic lipid is DOTAP, DODAC, DODMA, DSDMA, DOTMA, DDAB, DC-Chol, DMRIE, DOSPA, DOGS, CLinDMA, CpLinDMA, DMOBA, DOcarbDAP, DOAP, C12-200, or a mixture of two or more thereof, or a mixture of two or more thereof. In embodiments, the cationic lipid is DOTAP. In embodiments, the dilinoleic cationic lipid is MC3, an MC3 derivative, DLinDMA, DLin-K-C2-DMA, DLin-K-C3-DMA, DLin-K-C4-DMA, DLin-K6-DMA, DLin-K-MPZ, DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DLin-EG-DMA, DLincarbDAP, or a mixture of two or more thereof. In embodiments, the dilinoleic cationic lipid is MC3, Dlin-KC2-DMA, or a combination thereof. In embodiments, the dilinoleic cationic lipid is MC3. In embodiments, the dilinoleic cationic lipid is Dlin-KC2-DMA. In embodiments, the phospholipid is DSPC, DPPC, DOPE, POPC, POPE, POPG, DPPE, DMPE, DSPE, MMPE, DMPE, DEPE, SOPE, EPC, HSPC, or a mixture of two or more thereof. In embodiments, the phospholipid is DSPC. In embodiments, the sterol is cholesterol, cholestanol, cholestanone, cholestenone, coprostanol, cholesteryl-2'-hydroxyethyl ether, cholesteryl-4'-hydroxybutyl ether, or a mixture of two or more thereof. In embodiments, the sterol is cholesterol. In embodiments, the PEG-lipid conjugate is a polyethylene glycol having a molecular weight from about 1,000 Daltons to about 6,000 Daltons conjugated to a $C_{12}$-$C_{22}$ fatty acid lipid. In embodiments, the PEG-lipid conjugate is C16 PEG ceramide, DMG-PEG, DPPE-PEG, DPG-PEG, DSG-PEG, DSPE-PEG, or a mixture of two or more thereof. In embodiments, the PEG-lipid conjugate is C16 PEG ceramide, DMG-PEG, DPPE-PEG, DPG-PEG, DSG-PEG, DSPE-PEG, or a mixture of two or more thereof, wherein the PEG in each compound has a molecular weight of about 2,000 Daltons. In embodiments, the PEG-lipid conjugate is C16 PEG ceramide. In embodiments, the PEG-lipid conjugate is C16 PEG200 ceramide (i.e., wherein PEG2000 refers to PEG having a molecular weight of about 2,000 Daltons). In embodiments, the cationic lipid is DOTAP, the dilinoleic cationic lipid is MC3, the phospholipid is DSPC, the sterol is cholesterol, and the PEG-lipid conjugate is C16 PEG200 ceramide. In embodiments, the lipid nanoparticles are a plurality of lipid nanoparticles.

In embodiments of the lipid nanoparticles described herein, the cationic lipid is any cationic lipid known in the art. In embodiments, the cationic lipid is a non-linoleic cationic lipid. In embodiments, the cationic lipid is DOTAP, DODAC, DODMA, DSDMA, DOTMA, DDAB, DC-Chol, DMRIE, DOSPA, DOGS, CLinDMA, CpLinDMA, DMOBA, DOcarbDAP, DOAP, C12-200, or a mixture of two or more thereof. In embodiments, the cationic lipid is DOTAP. In embodiments, the cationic lipid is DODAC. In embodiments, the cationic lipid is DODMA. In embodiments, the cationic lipid is DSDMA. In embodiments, the cationic lipid is DOTMA. In embodiments, the cationic lipid is DDAB. In embodiments, the cationic lipid is DC-Chol. In embodiments, the cationic lipid is DMRIE. In embodiments, the cationic lipid is DOSPA. In embodiments, the cationic lipid is DOGS. In embodiments, the cationic lipid is CLinDMA. In embodiments, the cationic lipid is CpLinDMA. In embodiments, the cationic lipid is DMOBA. In embodiments, the cationic lipid is DOcarbDAP. In embodiments, the cationic lipid is DOAP. In embodiments, the cationic lipid is C12-200.

In embodiments of the lipid nanoparticles described herein, the dilinoleic cationic lipid is MC3, an MC3 derivative, DLinDMA, DLin-KC2-DMA, DLin-KC3-DMA, DLin-KC4-DMA, DLin-K6-DMA, DLin-K-MPZ, DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DLin-EG-DMA, DLincarbDAP, or a mixture of two or more thereof. In embodiments, the dilinoleic cationic lipid is MC3, Dlin-KC2-DMA, or a combination thereof. In embodiments, the dilinoleic cationic lipid is MC3. In embodiments, the dilinoleic cationic lipid is Dlin-KC2-DMA.

In embodiments of the lipid nanoparticles described herein, the phospholipid is any phospholipid known in the art. In embodiments, the phospholipid is DSPC, DPPC, DOPE, POPC, POPE, POPG, DPPE, DMPE, DSPE, MMPE, DMPE, DEPE, SOPE, EPC, HSPC, or a mixture of two or more thereof. In embodiments, the phospholipid is DSPC. In embodiments, the phospholipid is DPPC. In embodiments, the phospholipid is DOPE. In embodiments, the phospholipid is POPC. In embodiments, the phospholipid is POPE. In embodiments, the phospholipid is POPG. In embodiments, the phospholipid is DPPE. In embodiments, the phospholipid is DMPE. In embodiments, the phospholipid is DSPE. In embodiments, the phospholipid is MMPE. In embodiments, the phospholipid is DMPE. In embodiments, the phospholipid is DEPE. In embodiments, the phospholipid is SOPE. In embodiments, the phospholipid is EPC. In embodiments, the phospholipid is HSPC.

In embodiments of the lipid nanoparticles described herein, the sterol is any sterol known in the art. In embodiments, the sterol is cholesterol, cholestanol, cholestanone, cholestenone, coprostanol, cholesteryl-2'-hydroxyethyl ether, cholesteryl-4'-hydroxybutyl ether, or a mixture of two or more thereof. In embodiments, the sterol is cholesterol. In embodiments, the sterol is cholestanol. In embodiments, the sterol is cholestanone. In embodiments, the sterol is cholestenone. In embodiments, the sterol is coprostanol. In embodiments, the sterol is cholesteryl-2'-hydroxyethyl ether. In embodiments, the sterol is cholesteryl-4'-hydroxybutyl ether.

In embodiments of the lipid nanoparticles described herein, the PEG-lipid conjugate is a polyethylene glycol having a molecular weight from about 1,000 Daltons to about 6,000 Daltons conjugated to a $C_{12}$-$C_{22}$ fatty acid lipid. In embodiments, the PEG-lipid conjugate is a polyethylene glycol having a molecular weight from about 1,000 Daltons to about 6,000 Daltons conjugated to a $C_{12}$-$C_{20}$ fatty acid lipid. In embodiments, the PEG-lipid conjugate is a polyethylene glycol having a molecular weight from about 1,000 Daltons to about 6,000 Daltons conjugated to a $C_{12}$-$C_{18}$ fatty acid lipid. In embodiments, the PEG-lipid conjugate is a polyethylene glycol having a molecular weight from about 2,000 Daltons to about 5,000 Daltons conjugated to a $C_{12}$-$C_{22}$ fatty acid lipid. In embodiments, the PEG-lipid conjugate is a polyethylene glycol having a molecular weight from about 2,000 Daltons to about 5,000 Daltons conjugated to a $C_{12}$-$C_{20}$ fatty acid lipid. In embodiments, the PEG-lipid conjugate is a polyethylene glycol having a molecular weight from about 2,000 Daltons to about 5,000 Daltons conjugated to a $C_{12}$-$C_{18}$ fatty acid lipid. In embodiments, the PEG-lipid conjugate is a polyethylene glycol having a molecular weight from about 2,000 Daltons to about 5,000 Daltons conjugated to a $C_{14}$-$C_{18}$ fatty acid lipid. In embodiments, the PEG-lipid conjugate is a polyethylene glycol having a molecular weight from about 2,000 Daltons to about 5,000 Daltons conjugated to a $C_{16}$ fatty acid lipid. In embodiments, the fatty acid lipid is saturated. In embodiments, the fatty acid lipid is unsaturated. In embodiments, the fatty acid lipid comprises one, two, or three —CH=CH— groups. In embodiments, the fatty acid lipid comprises one —CH=CH— group. In embodiments, the fatty acid lipid comprises two —CH=CH— groups. In embodiments, the PEG-lipid conjugate is C16 PEG ceramide, DMG-PEG, DPPE-PEG, DPG-PEG, DSG-PEG, DSPE-PEG, or a mixture of two or more thereof. In embodiments, the PEG-lipid conjugate is C16 PEG ceramide. In embodiments, the PEG-lipid conjugate is DMG-PEG. In embodiments, the PEG-lipid conjugate is DPPE-PEG. In embodiments, the PEG-lipid conjugate is DPG-PEG. In embodiments, the PEG-lipid conjugate is DSG-PEG. In embodiments, the PEG-lipid conjugate is DSPE-PEG. In embodiments, the PEG-lipid conjugate is C16 PEG2000 ceramide, DMG-PEG2000, DPPE-PEG2000, DPG-PEG2000, DSG-PEG2000, DSPE-PEG2000, or a mixture of two or more thereof, wherein PEG2000 refers to PEG having a molecular weight of about 2,000 Daltons. In embodiments, the PEG-lipid conjugate is C16 PEG200 ceramide. In embodiments, the PEG-lipid conjugate is DMG-PEG2000. In embodiments, the PEG-lipid conjugate is DPPE-PEG2000. In embodiments, the PEG-lipid conjugate is DPG-PEG2000. In embodiments, the PEG-lipid conjugate is DSG-PEG2000. In embodiments, the PEG-lipid conjugate is DSPE-PEG2000.

The lipid nanoparticles (or plurality of lipid nanoparticles) described herein typically have an average size (e.g., mean diameter) from about 10 nm to about 200 nm, from about 20 nm to about 190 nm, from about 30 nm to about 175 nm, from about 40 nm to about 160 nm, from about 50 nm to about 150 nm, or from about 60 nm to about 140 nm. In embodiments, the lipid nanoparticles described herein have an average size from about 30 nm to about 130 nm. In embodiments, the lipid nanoparticles have an average size from about 35 nm to about 125 nm. In embodiments, the lipid nanoparticles have an average size from about 40 nm to about 120 nm. In embodiments, the lipid nanoparticles have an average size from about 45 nm to about 115 nm. In embodiments, the lipid nanoparticles have an average size from about 50 nm to about 110 nm. In embodiments, the lipid nanoparticles have an average size from about 55 nm to about 105 nm. In embodiments, the lipid nanoparticles have an average size from about 60 nm to about 105 nm. In embodiments, the lipid nanoparticles have an average size from about 60 nm to about 100 nm. In embodiments, the lipid nanoparticles have an average size from about 65 nm to about 95 nm. In embodiments, the lipid nanoparticles have an average size from about 70 nm to about 90 nm. In embodiments, the lipid nanoparticles have an average size from about 75 nm to about 85 nm. In embodiments, the lipid nanoparticles have an average size from about 75 nm to about 80 nm. In embodiments, the lipid nanoparticles have an average size of about 70 nm. In embodiments, the lipid nanoparticles have an average size of about 75 nm. In embodiments, the lipid nanoparticles have an average size of about 80 nm. In embodiments, the lipid nanoparticles have an average size of about 85 nm. In embodiments, the lipid nanoparticles have an average size of about 90 nm. In embodiments, lipid nanoparticles refers to a plurality of lipid nanoparticles.

With respect to particle size distribution characterization, a parameter used to define the size range of the lipid nanoparticles is called the "polydispersity index" (PDI). The term "polydispersity" is used to describe the degree of non-uniformity of a size distribution of particles. PDI is a number calculated from a two-parameter fit to the correlation data (the cumulants analysis). PDI is a representation of the distribution of size populations within a given sample. In embodiments, the lipid nanoparticles described herein have a PDI from about 0.1 to about 0.2. In embodiments, the lipid nanoparticles have a polydispersity of less than 0.27. In embodiments, the lipid nanoparticles have a PDI from about 0.11 to about 0.2. In embodiments, the lipid nanoparticles have a PDI from about 0.12 to about 0.2. In embodiments, the lipid nanoparticles have a PDI from about 0.13 to about 0.19. In embodiments, the lipid nanoparticles have a PDI from about 0.14 to about 0.18. In embodiments, the lipid nanoparticles have a PDI from about 0.15 to about 0.17. In embodiments, the lipid nanoparticles have a PDI from about 0.14 to about 0.16. In embodiments, the lipid nanoparticles have a PDI from about 0.16 to about 0.18. In embodiments, the lipid nanoparticles have a PDI of about 0.1. In embodiments, the lipid nanoparticles have a PDI of about 0.11. In embodiments, the lipid nanoparticles have a PDI of about 0.12. In embodiments, the lipid nanoparticles have a PDI of about 0.12. In embodiments, the lipid nanoparticles have a PDI of about 0.14. In embodiments, the lipid nanoparticles have a PDI of about 0.15. In embodiments, the lipid nanoparticles have a PDI of about 0.16. In embodiments, the lipid nanoparticles have a PDI of about 0.17. In embodiments, the lipid nanoparticles have a PDI of about 0.18. In embodiments, the lipid nanoparticles have a PDI of about 0.19. In embodiments, the lipid nanoparticles have a PDI of about 0.20. In embodiments, the lipid nanoparticles have a PDI of about 0.16. For PDI, lipid nanoparticles refers to a plurality of lipid nanoparticles.

"Zeta potential" is a measure of the effective electric charge on the nanoparticle surface. The magnitude of the zeta potential provides information about particle stability, with particles with higher magnitude zeta potentials exhibiting increased stability due to a larger electrostatic repulsion between particles. In embodiments, the lipid nanoparticles described herein have a zeta potential from about 10 mV to about 26 mV. In embodiments, the lipid nanoparticles have a zeta potential from about 1 mV to about 25 mV In embodiments, the lipid nanoparticles have a zeta potential from about 12 mV to about 24 mV. In embodiments, the lipid nanoparticles have a zeta potential from about 13 mV to about 23 mV. In embodiments, the lipid nanoparticles have a zeta potential from about 14 mV to about 22 mV. In embodiments, the lipid nanoparticles have a zeta potential from about 15 mV to about 21 mV. In embodiments, the lipid nanoparticles have a zeta potential from about 16 mV to about 20 mV. In embodiments, the lipid nanoparticles have a zeta potential from about 17 mV to about 20 mV In embodiments, the lipid nanoparticles have a zeta potential from about 17 mV to about 19 mV In embodiments, the lipid nanoparticles have a zeta potential from about 18 mV to about 19 mV. In embodiments, the lipid nanoparticles have a zeta potential from about 19 mV to about 20 mV. In embodiments, the lipid nanoparticles have a zeta potential of about 12 mV. In embodiments, the lipid nanoparticles have a zeta potential of about 13 mV. In embodiments, the lipid nanoparticles have a zeta potential of about 14 mV. In embodiments, the lipid nanoparticles have a zeta potential of about 15 mV. In embodiments, the lipid nanoparticles have a zeta potential of about 16 mV. In embodiments, the lipid nanoparticles have a zeta potential of about 17 mV. In embodiments, the lipid nanoparticles have a zeta potential of about 18 mV. In embodiments, the lipid nanoparticles have a zeta potential of about 18.5 mV. In embodiments, the lipid nanoparticles have a zeta potential of about 18.58 mV. In embodiments, the lipid nanoparticles have a zeta potential of about 19 mV. In embodiments, the lipid nanoparticles have a zeta potential of about 20 mV. In embodiments, the lipid nanoparticles have a zeta potential of about 21 mV. In embodiments, the lipid nanoparticles have a zeta potential of about 22 mV. In embodiments, the lipid nanoparticles have a zeta potential of about 23 mV. In embodiments, the lipid nanoparticles have a zeta potential of about 24 mV.

In embodiments, the disclosure provides a plurality of the lipid nanoparticles described herein.

Lipid Nanoparticles Encapsulating Therapeutic Agent

In embodiments, the disclosure provides a lipid nanoparticle comprising a nucleic acid encapsulated within the lipid nanoparticle. In embodiments, the nucleic acid is RNA. In embodiments, the nucleic acid is DNA. In embodiments, the nucleic acid is sense RNA. In embodiments, the nucleic acid is antisense RNA. In embodiments, the nucleic acid is siRNA. In embodiments, the nucleic acid is mRNA. In embodiments, the nucleic acid is a plasmid. In embodiments, the nucleic acid is a minigene. In embodiments, the nucleic acid is a nucleic acid described in WO 2021/195025.

In embodiments, the disclosure provides a lipid nanoparticle comprising a nucleic acid encapsulated therein, wherein the nucleic acid comprises 15 nucleotides to 30 nucleotides and is capable of hybridizing to a target sequence in Table 1. In embodiments, the nucleic acid comprises 20 nucleotides to 25 nucleotides. In embodiments, the nucleic acid comprises 21 to 23 nucleotides. In embodiments, the nucleic acid comprises 21 nucleotides. In embodiments, the nucleic acid comprises 22 nucleotides. In embodiments, the nucleic acid comprises 23 nucleotides. In embodiments, the nucleic acid is siRNA. In embodiments, the nucleic acid is antisense RNA. In embodiments, the nucleic acid is sense RNA. In embodiments, the nucleic acid comprises a modified base, a modified sugar, a modified phosphate, or a combination of two or more thereof. In embodiments, the nucleic acid comprises a modified sugar and a modified phosphate. In embodiments, the nucleic acid comprises a modified base and a modified phosphate. In embodiments, the nucleic acid comprises a modified base and a modified sugar. In embodiments, the nucleic acid comprises a modified base. In embodiments, the nucleic acid comprises a modified sugar. In embodiments, the nucleic acid comprises a modified phosphate. In embodiments, the modified base is 2'O-Methyl modified base, a 2'O-methoxy-ethoxy modified base, a 2'fluoro modified base, a 5-methyl-modified cytidine, or pseudouridine. In embodiments, the modified base is a 2'O-Methyl modified base. In embodiments, the modified phosphate is phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite. In embodiments, the modified phosphate is phosphorothioate. In embodiments, the modified sugar is deoxyribose.

In embodiments, the disclosure provides a lipid nanoparticle comprising a nucleic acid encapsulated therein, wherein the nucleic acid comprises 15 nucleotides to 30 nucleotides and is capable of hybridizing to SEQ ID NO:57, SEQ ID NO:51, SEQ ID NO:63, SEQ ID NO:55, SEQ ID NO:45, SEQ ID NO:50, or SEQ ID NO:62. In embodiments, the lipid nanoparticle comprises a nucleic acid encapsulated therein, wherein the nucleic acid comprises 15 nucleotides to 30 nucleotides and is capable of hybridizing to SEQ ID NO:57. In embodiments, the lipid nanoparticle comprises a nucleic acid encapsulated therein, wherein the nucleic acid comprises 15 nucleotides to 30 nucleotides and is capable of hybridizing to SEQ ID NO:51. In embodiments, the lipid nanoparticle comprises a nucleic acid encapsulated therein, wherein the nucleic acid comprises 15 nucleotides to 30 nucleotides and is capable of hybridizing to SEQ ID NO:63. In embodiments, the lipid nanoparticle comprises a nucleic acid encapsulated therein, wherein the nucleic acid comprises 15 nucleotides to 30 nucleotides and is capable of hybridizing to SEQ ID NO:55. In embodiments, the lipid nanoparticle comprises a nucleic acid encapsulated therein, wherein the nucleic acid comprises 15 nucleotides to 30 nucleotides and is capable of hybridizing to SEQ ID NO:45. In embodiments, the lipid nanoparticle comprises a nucleic acid encapsulated therein, wherein the nucleic acid comprises 15 nucleotides to 30 nucleotides and is capable of hybridizing to SEQ ID NO:50. In embodiments, the lipid nanoparticle comprises a nucleic acid encapsulated therein, wherein the nucleic acid comprises 15 nucleotides to 30 nucleotides and is capable of hybridizing to SEQ ID NO:62. In embodiments, the nucleic acid comprises 20 nucleotides to 25 nucleotides. In embodiments, the nucleic acid comprises 21 to 23 nucleotides. In embodiments, the nucleic acid comprises 21 nucleotides. In embodiments, the nucleic acid comprises 22 nucleotides. In embodiments, the nucleic acid comprises 23 nucleotides. In embodiments, the nucleic acid is siRNA. In embodiments, the nucleic acid is antisense RNA. In embodiments, the nucleic acid is sense RNA. In embodiments, the nucleic acid comprises a modified base, a modified sugar, a modified phosphate, or a combination of two or more thereof. In embodiments, the nucleic acid comprises a modified sugar and a modified phosphate. In embodiments, the nucleic acid comprises a modified base and a modified phosphate. In embodiments, the nucleic acid comprises a modified base and a modified sugar. In embodiments, the nucleic acid comprises a modified base. In embodiments, the nucleic acid comprises a modified sugar. In embodiments, the nucleic acid comprises a modified phosphate. In embodiments, the modified base is 2'O-Methyl modified base, a 2'O-methoxyethoxy modified base, a 2'fluoro modified base, a 5-methyl-modified cytidine, or pseudouridine. In embodiments, the modified base is a 2'O-Methyl modified base. In embodiments, the modified phosphate is phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite. In embodiments, the modified phosphate is phosphorothioate. In embodiments, the modified sugar is deoxyribose.

In embodiments, the disclosure provides a lipid nanoparticle comprising a nucleic acid encapsulated therein, wherein the nucleic acid comprises SEQ ID NO:1 hybridized to SEQ ID NO:3. In embodiments, the disclosure provides a lipid nanoparticle comprising a nucleic acid encapsulated therein, wherein the nucleic acid comprises SEQ ID NO:1 and/or SEQ ID NO:3. In embodiments, the disclosure provides a lipid nanoparticle comprising a nucleic acid encapsulated therein, wherein the nucleic acid comprises SEQ ID NO:2 hybridized to SEQ ID NO:4. In embodiments, the disclosure provides a lipid nanoparticle comprising a nucleic acid encapsulated therein, wherein the nucleic acid comprises SEQ ID NO:2 and/or SEQ ID NO:4. In embodiments, the disclosure provides a lipid nanoparticle comprising a nucleic acid encapsulated therein, wherein the nucleic acid comprises SEQ ID NO:9 hybridized to SEQ ID NO:10. In embodiments, the disclosure provides a lipid nanoparticle comprising a nucleic acid encapsulated therein, wherein the nucleic acid comprises SEQ ID NO:9 and/or SEQ ID NO:10. In embodiments, the disclosure provides a lipid nanoparticle comprising a nucleic acid encapsulated therein, wherein the nucleic acid comprises SEQ ID NO:11 hybridized to SEQ ID NO:12. In embodiments, the disclosure provides a lipid nanoparticle comprising a nucleic acid encapsulated therein, wherein the nucleic acid comprises SEQ ID NO:11 and/or SEQ ID NO:12. In embodiments, the disclosure provides a lipid nanoparticle comprising a nucleic acid encapsulated therein, wherein the nucleic acid comprises SEQ ID NO:5 hybridized to SEQ ID NO:7. In embodiments, the disclosure provides a lipid nanoparticle comprising a nucleic acid encapsulated therein, wherein the nucleic acid comprises SEQ ID NO:5 and/or SEQ ID NO:7. In embodiments, the disclosure provides a lipid nanoparticle comprising a nucleic acid encapsulated therein, wherein the nucleic acid comprises SEQ ID NO:6 hybridized to SEQ ID NO:8. In embodiments, the disclosure provides a lipid nanoparticle comprising a nucleic acid encapsulated therein, wherein the nucleic acid comprises SEQ ID NO:6 and/or SEQ ID NO:8. In embodiments, the disclosure provides a lipid nanoparticle comprising a nucleic acid encapsulated therein, wherein the nucleic acid comprises SEQ ID NO:13 hybridized to SEQ ID NO:14. In embodiments, the disclosure provides a lipid nanoparticle comprising a nucleic acid encapsulated therein, wherein the nucleic acid comprises SEQ ID NO:13 and/or SEQ ID NO:14. In embodiments, the disclosure provides a lipid nanoparticle comprising a nucleic acid encapsulated therein, wherein the nucleic acid comprises SEQ ID NO:15 hybridized to SEQ ID NO:16. In embodiments, the disclosure provides a lipid nanoparticle comprising a nucleic acid encapsulated therein, wherein the nucleic acid comprises SEQ ID NO:15 and/or SEQ ID NO:16. In embodiments, the disclosure provides a lipid nanoparticle comprising a nucleic acid encapsulated therein, wherein the nucleic acid comprises SEQ ID NO:17 hybridized to SEQ ID NO:18. In embodiments, the disclosure provides a lipid nanoparticle comprising a nucleic acid encapsulated therein, wherein the nucleic acid comprises SEQ ID NO:17 and/or SEQ ID NO:18. In embodiments, the disclosure provides a lipid nanoparticle comprising a nucleic acid encapsulated therein, wherein the nucleic acid comprises SEQ ID NO:19 hybridized to SEQ ID NO:20. In embodiments, the disclosure provides a lipid nanoparticle comprising a nucleic acid encapsulated therein, wherein the nucleic acid comprises SEQ ID NO:21 hybridized to SEQ ID NO:22. In embodiments, the disclosure provides a lipid nanoparticle comprising a nucleic acid encapsulated therein, wherein the nucleic acid comprises SEQ ID NO:23 hybridized to SEQ ID NO:24. In embodiments, the disclosure provides a lipid nanoparticle comprising a nucleic acid encapsulated therein, wherein the nucleic acid comprises SEQ ID NO:25 hybridized to SEQ ID NO:26. In embodiments, the disclosure provides a lipid nanoparticle comprising a nucleic acid encapsulated therein, wherein the nucleic acid comprises SEQ ID NO:27 hybridized to SEQ ID NO:28. In embodiments, the disclosure provides a lipid nanoparticle comprising a nucleic acid encapsulated therein, wherein the nucleic acid comprises SEQ ID NO:29 hybridized to SEQ ID NO:30. In embodiments, the disclosure provides a lipid nanoparticle comprising a nucleic acid encapsulated therein, wherein the nucleic acid comprises SEQ ID NO:31 hybridized to SEQ ID NO:32. In embodiments, the disclosure provides a lipid nanoparticle comprising a nucleic acid encapsulated therein, wherein the nucleic acid comprises SEQ ID NO:33 hybridized to SEQ ID NO:34. In embodiments, the disclosure provides a lipid nanoparticle comprising a nucleic acid encapsulated therein, wherein the nucleic acid comprises SEQ ID NO:35 hybridized to SEQ ID NO:36. In embodiments, the disclosure provides a lipid nanoparticle comprising a nucleic acid encapsulated therein, wherein the nucleic acid comprises SEQ ID NO:37 hybridized to SEQ ID NO:38. In embodiments, the disclosure provides a lipid nanoparticle comprising a nucleic acid encapsulated therein, wherein the nucleic acid comprises SEQ ID NO:39 hybridized to SEQ ID NO:40. In embodiments, the disclosure provides a lipid nanoparticle comprising a nucleic acid encapsulated therein, wherein the nucleic acid comprises SEQ ID NO:41 hybridized to SEQ ID NO:42. In embodiments, the disclosure provides a lipid nanoparticle comprising a nucleic acid encapsulated therein, wherein the nucleic acid comprises SEQ ID NO:43 hybridized to SEQ ID NO:44. In embodiments, the nucleic acid is siRNA. In embodiments, the nucleic acid is antisense RNA. In embodiments, the nucleic acid is sense RNA. In embodiments, the nucleic acid comprises a modified base, a modified sugar, a modified phosphate, or a combination of two or more thereof. In embodiments, the nucleic acid comprises a modified sugar and a modified phosphate. In embodiments, the nucleic acid comprises a modified base and a modified phosphate. In embodiments, the nucleic acid comprises a modified base and a modified sugar. In embodiments, the nucleic acid comprises a modified base. In embodiments, the nucleic acid comprises a modified sugar. In embodiments, the nucleic acid comprises a modified phosphate. In embodiments, the modified base is 2'O-Methyl modified base, a 2'O-methoxyethoxy modified base, a 2'fluoro modified base, a 5-methyl-modified cytidine, or pseudouridine. In embodiments, the modified base is a 2'O-Methyl modified base. In embodiments, the modified phosphate is phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite. In embodiments, the modified phosphate is phosphorothioate. In embodiments, the modified sugar is deoxyribose.

In embodiments, the lipid nanoparticles comprise a nucleic acid encapsulated therein, wherein the nucleic acid comprises a sense strand from Table 1 hybridized to the corresponding antisense strand from Table 1. In embodiments, the lipid nanoparticles comprise a nucleic acid encapsulated therein, wherein the nucleic acid comprises a sense strand from Table 1. In embodiments, the lipid nanoparticles comprise a nucleic acid encapsulated therein, wherein the nucleic acid comprises an antisense strand from Table 1. In embodiments, the nucleic acid in Table 1 further comprises a modified base, a modified sugar, a modified phosphate, or a combination of two or more thereof. In embodiments, the nucleic acid in Table 1 further comprises a modified sugar and a modified phosphate. In embodiments, the nucleic acid in Table 1 further comprises a modified base and a modified phosphate. In embodiments, the nucleic acid in Table 1 further comprises a modified base and a modified sugar. In embodiments, the nucleic acid in Table 1 further comprises a modified base. In embodiments, the nucleic acid in Table 1 further comprises a modified sugar. In embodiments, the nucleic acid in Table 1 further comprises a modified phosphate. In embodiments, the modified base is 2'O-Methyl modified base, a 2'O-methoxyethoxy modified base, a 2'fluoro modified base, a 5-methyl-modified cytidine, or pseudouridine. In embodiments, the modified base is a 2'O-Methyl modified base. In embodiments, the modified phosphate is phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite. In embodiments, the modified phosphate is phosphorothioate. In embodiments, the modified sugar is deoxyribose.

TABLE 1

| SIRNA Code Name | Target Sequence SARS-CoV-2 site 5'-3' | siRNA sequence (5'-3') |
|---|---|---|
| siUC1 | SEQ ID NO: 45 | Sense: SEQ ID NO: 13 |
| | | Antisense: SEQ ID NO: 14 |
| siUC2 | SEQ ID NO: 46 | Sense: SEQ ID NO: 19 |
| | | Antisense: SEQ ID NO: 20 |
| siUC3 | SEQ ID NO: 47 | Sense: SEQ ID NO: 21 |
| | | Antisense: SEQ ID NO: 22 |
| siUC4 | SEQ ID NO: 48 | Sense: SEQ ID NO: 23 |
| | | Antisense: SEQ ID NO: 24 |
| siUC5 | SEQ ID NO: 27 | Sense: SEQ ID NO: 25 |
| | | Antisense: SEQ ID NO: 26 |
| siUC6 | SEQ ID NO: 50 | Sense: SEQ ID NO: 15 |
| | | Antisense: SEQ ID NO: 16 |
| siUC7 | SEQ ID NO: 51 | Sense: SEQ ID NO: 9 |
| | | Antisense: SEQ ID NO: 10 |
| siUC8 | SEQ ID NO: 52 | Sense: SEQ ID NO: 27 |
| | | Antisense: SEQ ID NO: 28 |
| siUC9 | SEQ ID NO: 53 | Sense: SEQ ID NO: 29 |
| | | Antisense: SEQ ID NO: 30 |
| siUC10 | SEQ ID NO: 54 | Sense: SEQ ID NO: 31 |
| | | Antisense: SEQ ID NO: 32 |
| siUTR1 | SEQ ID NO: 55 | dsiRNA Sense: SEQ ID NO: 5 |
| | | siRNA Antisense: SEQ ID NO: 7 |
| siUTR1 Modified | SEQ ID NO: 55 | dsiRNA Sense: SEQ ID NO: 6 |
| | | siRNA Antisense: SEQ ID NO: 8 |
| siUTR2 | SEQ ID NO: 56 | dsiRNA Sense: SEQ ID NO: 33 |
| | | siRNA Antisense: SEQ ID NO: 34 |
| siUTR3 | SEQ ID NO: 57 | dsiRNA Sense: SEQ ID NO: 1 |
| | | siRNA Antisense: SEQ ID NO: 3 |
| siUTR3 Modified | SEQ ID NO: 57 | dsiRNA Sense: SEQ ID NO: 2 |
| | | siRNA Antisense: SEQ ID NO: 4 |
| siUTR4 | SEQ ID NO: 58 | dsiRNA Sense: SEQ ID NO: 35 |
| | | siRNA Antisense: SEQ ID NO: 36 |
| siUTR5 | SEQ ID NO: 59 | dsiRNA Sense: SEQ ID NO: 37 |
| | | siRNA Antisense: SEQ ID NO: 38 |
| siRdRp1 | SEQ ID NO: 60 | Sense: SEQ ID NO: 39 |
| | | Antisense: SEQ ID NO: 40 |
| siRdRp4 | SEQ ID NO: 61 | Sense: SEQ ID NO: 41 |
| | | Antisense: SEQ ID NO: 42 |
| siHel1 | SEQ ID NO: 62 | Sense: SEQ ID NO: 17 |
| | | Antisense: SEQ ID NO: 18 |
| siHel2 | SEQ ID NO: 63 | Sense: SEQ ID NO: 11 |
| | | Antisense: SEQ ID NO: 12 |
| RdRp1b | SEQ ID NO: 78 | Sense: SEQ ID NO: 43 |
| | | Antisense: SEQ ID NO: 44 |

In embodiments, the disclosure provides a lipid nanoparticle comprising a nucleic acid encapsulated therein, wherein the nucleic acid comprises 15 nucleotides to 30 nucleotides and is capable of hybridizing to a SARS-CoV-2 target sequence in Table 2. In embodiments, the nucleic acid comprises 20 nucleotides to 25 nucleotides. In embodiments, the nucleic acid comprises 21 to 23 nucleotides. In embodiments, the nucleic acid comprises 21 nucleotides. In embodiments, the nucleic acid comprises 22 nucleotides. In embodiments, the nucleic acid comprises 23 nucleotides. In embodiments, the nucleic acid is siRNA. In embodiments, the nucleic acid is antisense RNA. In embodiments, the nucleic acid is sense RNA. In embodiments, the nucleic acid comprises a modified base, a modified sugar, a modified phosphate, or a combination of two or more thereof. In embodiments, the nucleic acid comprises a modified sugar and a modified phosphate. In embodiments, the nucleic acid comprises a modified base and a modified phosphate. In embodiments, the nucleic acid comprises a modified base and a modified sugar. In embodiments, the nucleic acid comprises a modified base. In embodiments, the nucleic acid comprises a modified sugar. In embodiments, the nucleic acid comprises a modified phosphate. In embodiments, the modified base is 2'O-Methyl modified base, a 2'O-methoxy-ethoxy modified base, a 2'fluoro modified base, a 5-methyl-modified cytidine, or pseudouridine. In embodiments, the modified base is a 2'O-Methyl modified base. In embodiments, the modified phosphate is phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite. In embodiments, the modified phosphate is phosphorothioate. In embodiments, the modified sugar is deoxyribose.

In embodiments, the disclosure provides a lipid nanoparticle comprising a nucleic acid encapsulated therein, wherein the nucleic acid comprises 15 nucleotides to 30 nucleotides and is capable of hybridizing to a MERS-CoV target sequence in Table 2. In embodiments, the nucleic acid comprises 20 nucleotides to 25 nucleotides. In embodiments, the nucleic acid comprises 21 to 23 nucleotides. In embodiments, the nucleic acid comprises 21 nucleotides. In embodiments, the nucleic acid comprises 22 nucleotides. In embodiments, the nucleic acid comprises 23 nucleotides. In embodiments, the nucleic acid is siRNA. In embodiments, the nucleic acid is antisense RNA. In embodiments, the nucleic acid is sense RNA. In embodiments, the nucleic acid comprises a modified base, a modified sugar, a modified phosphate, or a combination of two or more thereof. In embodiments, the nucleic acid comprises a modified sugar and a modified phosphate. In embodiments, the nucleic acid comprises a modified base and a modified phosphate. In embodiments, the nucleic acid comprises a modified base and a modified sugar. In embodiments, the nucleic acid comprises a modified base. In embodiments, the nucleic acid comprises a modified sugar. In embodiments, the nucleic acid comprises a modified phosphate. In embodiments, the modified base is 2'O-Methyl modified base, a 2'O-methoxy-ethoxy modified base, a 2'fluoro modified base, a 5-methyl-modified cytidine, or pseudouridine. In embodiments, the modified base is a 2'O-Methyl modified base. In embodiments, the modified phosphate is phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite.

In embodiments, the modified phosphate is phosphorothioate. In embodiments, the modified sugar is deoxyribose.

In embodiments, the disclosure provides a lipid nanoparticle comprising a nucleic acid encapsulated therein, wherein the nucleic acid comprises 15 nucleotides to 30 nucleotides and is capable of hybridizing to a SARS-CoV-1 target sequence in Table 2. In embodiments, the nucleic acid comprises 20 nucleotides to 25 nucleotides. In embodiments, the nucleic acid comprises 21 to 23 nucleotides. In embodiments, the nucleic acid comprises 21 nucleotides. In embodiments, the nucleic acid comprises 22 nucleotides. In embodiments, the nucleic acid comprises 23 nucleotides. In embodiments, the nucleic acid is siRNA. In embodiments, the nucleic acid is antisense RNA. In embodiments, the nucleic acid is sense RNA. In embodiments, the nucleic acid comprises a modified base, a modified sugar, a modified phosphate, or a combination of two or more thereof. In embodiments, the nucleic acid comprises a modified sugar and a modified phosphate. In embodiments, the nucleic acid comprises a modified base and a modified phosphate. In embodiments, the nucleic acid comprises a modified base and a modified sugar. In embodiments, the nucleic acid comprises a modified base. In embodiments, the nucleic acid comprises a modified sugar. In embodiments, the nucleic acid comprises a modified phosphate. In embodiments, the modified base is 2'O-Methyl modified base, a 2'O-methoxy-ethoxy modified base, a 2'fluoro modified base, a 5-methyl-modified cytidine, or pseudouridine. In embodiments, the modified base is a 2'O-Methyl modified base. In embodiments, the modified phosphate is phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite. In embodiments, the modified phosphate is phosphorothioate. In embodiments, the modified sugar is deoxyribose.

TABLE 2

| | | Target Site Sequence (5'-3') |
| --- | --- | --- |
| siRdRp1 | | |
| SARS-COV-2 | MN985325 | SEQ ID NO: 60 |
| SARS-COV-1 | NC_004718 | SEQ ID NO: 64 |
| MERS | KX034094 | SEQ ID NO: 235 |
| siRdRp4 | | |
| SARS-COV-2 | MN985325 | SEQ ID NO: 61 |
| SARS-COV-1 | NC_004718 | SEQ ID NO: 61 |
| MERS | KX034094 | SEQ ID NO: 65 |
| siHel1 | | |
| SARS-COV-2 | MN985325 | SEQ ID NO: 62 |
| SARS-COV-1 | NC_004718 | SEQ ID NO: 66 |
| MERS | KX034094 | SEQ ID NO: 67 |
| siHel2 | | |
| SARS-COV-2 | MN985325 | SEQ ID NO: 63 |
| SARS-COV-1 | NC_004718 | SEQ ID NO: 68 |
| MERS | KX034094 | SEQ ID NO: 69 |

Table 2 shows siRNA conservation between targeting various beta coronaviruses. Alignments are shown between SARS-CoV-1, SARS-CoV-2 and MERs. Underlined DNA bases indicate a different nucleotide compared to SARS-CoV-2.

In embodiments, the lipid nanoparticle comprises a nucleic acid (e.g., RNA, sense RNA, antisense RNA, siRNA, mRNA, DNA, plasmid, minigene) described herein.

In embodiments, the lipid nanoparticle comprises two to six different nucleic acids (e.g., RNA, sense RNA, sense RNA, antisense RNA, siRNA, mRNA, DNA, plasmid, minigene) described herein. In embodiments, the lipid nanoparticle comprises two to five different nucleic acids (e.g., RNA, sense RNA, sense RNA, antisense RNA, siRNA, mRNA, DNA, plasmid, minigene) described herein. In embodiments, the lipid nanoparticle comprises two to four different nucleic acids (e.g., RNA, sense RNA, sense RNA, antisense RNA, siRNA, mRNA, DNA, plasmid, minigene) described herein. In embodiments, the lipid nanoparticle comprises two or three different nucleic acids (e.g., RNA, sense RNA, antisense RNA, siRNA, mRNA, DNA, plasmid, minigene) described herein. In embodiments, the lipid nanoparticle comprises two different nucleic acids (e.g., RNA, sense RNA, sense RNA, antisense RNA, siRNA, mRNA, DNA, plasmid, minigene) described herein. In embodiments, the lipid nanoparticle comprises three different nucleic acids (e.g., RNA, sense RNA, sense RNA, antisense RNA, siRNA, mRNA, DNA, plasmid, minigene) described herein. In embodiments, the lipid nanoparticle comprises four different nucleic acid (e.g., RNA, sense RNA, sense RNA, antisense RNA, siRNA, mRNA, DNA, plasmid, minigene) described herein.

Pharmaceutical Compositions

Provided herein are pharmaceutical compositions comprising a plurality of lipid nanoparticles which comprise nucleic acids encapsulated therein (e.g., RNA, sense RNA, antisense RNA, siRNA, mRNA, DNA, plasmid, minigene) and a pharmaceutically acceptable excipient.

In embodiments, the pharmaceutical compositions comprise a first lipid nanoparticle which comprises a first nucleic acid (e.g., RNA, sense RNA, antisense RNA, siRNA mRNA, DNA, plasmid, minigene) and a second lipid nanoparticle which comprises a second nucleic acid (e.g., RNA, sense RNA, antisense RNA, siRNA mRNA, DNA, plasmid, minigene); wherein the first lipid nanoparticle and the second lipid nanoparticle are the same or different, and wherein the first nucleic acid and second nucleic acid are different. In embodiments, the first lipid nanoparticle and the second lipid nanoparticle are the same (i.e., comprise the same lipids). In embodiments, the pharmaceutical compositions comprise a first lipid nanoparticle which comprises a first nucleic acid (e.g., RNA, sense RNA, antisense RNA, siRNA mRNA, DNA, plasmid, minigene); a second lipid nanoparticle which comprises a second nucleic acid (e.g., RNA, sense RNA, antisense RNA, siRNA mRNA, DNA, plasmid, minigene); and a third lipid nanoparticle which comprises a third nucleic acid (e.g., RNA, sense RNA, antisense RNA, siRNA mRNA, DNA, plasmid, minigene); wherein the first, second, and third lipid nanoparticles are the same or different, and wherein the first, second, and third nucleic acids are different. In embodiments, the first, second, and third lipid nanoparticles are the same (i.e., comprise the same lipids). In embodiments, the first, second, and third nucleic acids are selected from the group consisting of siUTR3, siUC7, siHel2, siUTR1, siUC1, siUC6, and siHel1, and the lipid nanoparticles comprise the same lipid components. In embodiments, the first, second, and third nucleic acids are siUTR3, siUC7, and siHel2, and the lipid nanoparticles comprise the same lipid components. In embodiments, the pharmaceutical compositions comprise a first lipid nanoparticle which comprises a first nucleic acid (e.g., RNA, sense RNA, antisense RNA, siRNA mRNA, DNA, plasmid, minigene); a second lipid nanoparticle which comprises a second nucleic acid (e.g., RNA, sense RNA, antisense RNA, siRNA mRNA, DNA, plasmid, minigene); a third lipid nanoparticle which comprises a third nucleic acid (e.g., RNA, sense RNA, antisense RNA, siRNA mRNA, DNA, plasmid, minigene); a fourth lipid nanoparticle which comprises a fourth nucleic acid (e.g., RNA, sense RNA, antisense RNA, siRNA mRNA, DNA, plasmid, minigene); wherein the first, second, third, and fourth lipid nanoparticles are the same or different, and wherein the first, second, third, and fourth nucleic acids are different. In embodiments, the first, second, third, and fourth lipid nanoparticles are the same (i.e., comprise the same lipids). The pharmaceutical compositions can optionally further comprises a fifth lipid nanoparticle which comprises a fifth nucleic acid (e.g., RNA, sense RNA, antisense RNA, siRNA mRNA, DNA, plasmid, minigene); wherein the first, second, third, fourth, and fifth lipid nanoparticles are the same or different, and wherein the first, second, third, fourth, and fifth nucleic acids are different. In embodiments, the first, second, third, fourth, and fifth lipid nanoparticles are the same (i.e., comprise the same lipids). The compositions are suitable for formulation and administration in vitro or in vivo. Suitable pharmaceutically acceptable excipients are known in the art and described, e.g., in Remington: The Science and Practice of Pharmacy, 21st Edition, David B. Troy, ed., Lippicott Williams & Wilkins (2005).

In embodiments, the disclosure provides pharmaceutical compositions comprising a plurality of first lipid nanoparticles comprising a first nucleic acid and a plurality of second lipid nanoparticles comprising a second nucleic acid; wherein the plurality of the first and second lipid nanoparticles are described herein; wherein the first nucleic acid and the second nucleic acid are different; and wherein the first nucleic acid and second nucleic acid are selected from the group consisting of: (a) SEQ ID NO:1 hybridized to SEQ ID NO:3 or SEQ ID NO:2 hybridized to SEQ ID NO:4; (b) SEQ ID NO:9 hybridized to SEQ ID NO: 10; (c) SEQ ID NO: 11 hybridized to SEQ ID NO: 12; (d) SEQ ID NO:5 hybridized to SEQ ID NO:7 or SEQ ID NO:6 hybridized to SEQ ID NO: 8; (e) SEQ ID NO:13 hybridized to SEQ ID NO: 14; (f) SEQ ID NO:15 hybridized to SEQ ID NO:16; and (g) SEQ ID NO:17 hybridized to SEQ ID NO:18. In embodiments, the first nucleic acid and second nucleic acid are selected from the group consisting of: (i) SEQ ID NO:1 hybridized to SEQ ID NO:3 or SEQ ID NO:2 hybridized to SEQ ID NO:4; (ii) SEQ ID NO:9 hybridized to SEQ ID NO: 10; (iii) SEQ ID NO: 11 hybridized to SEQ ID NO: 12; and (iv) SEQ ID NO:17 hybridized to SEQ ID NO:18. In embodiments, the first nucleic acid and second nucleic acid are selected from the group consisting of: (i) SEQ ID NO:1 hybridized to SEQ ID NO:3 or SEQ ID NO:2 hybridized to SEQ ID NO:4; (ii) SEQ ID NO:9 hybridized to SEQ ID NO: 10; and (iii) SEQ ID NO:11 hybridized to SEQ ID NO: 12. In embodiments, the first nucleic acid and second nucleic acid are selected from the group consisting of: (i) SEQ ID NO:1 hybridized to SEQ ID NO:3; (ii) SEQ ID NO:9 hybridized to SEQ ID NO:10; and (iii) SEQ ID NO:11 hybridized to SEQ ID NO:12. In embodiments, the first nucleic acid and second nucleic acid are selected from the group consisting of: (i) SEQ ID NO:2 hybridized to SEQ ID NO:4; (ii) SEQ ID NO:9 hybridized to SEQ ID NO:10; and (iii) SEQ ID NO: 11 hybridized to SEQ ID NO: 12. In embodiments, the first nucleic acid and second nucleic acid are selected from the group consisting of: (i) SEQ ID NO:1 hybridized to SEQ ID NO:3 or SEQ ID NO:2 hybridized to SEQ ID NO: 4; (ii) SEQ ID NO:9 hybridized to SEQ ID NO:10; and (iii) SEQ ID NO:17 hybridized to SEQ ID NO:18. In embodiments, the first nucleic acid and second nucleic acid are selected from the group consisting of: (i) SEQ ID NO:1 hybridized to SEQ ID NO:3; (ii) SEQ ID NO:9 hybridized to SEQ ID NO: 10; and (iii) SEQ ID NO:17 hybridized to SEQ ID NO:18. In embodiments, the first nucleic acid and second nucleic acid are selected from the group consisting of: (i) SEQ ID NO:2 hybridized to SEQ ID NO:4; (ii) SEQ ID NO:9 hybridized to SEQ ID NO:10; and (iii) SEQ ID NO: 17 hybridized to SEQ ID NO:18. In embodiments, the pharmaceutical compositions comprise a pharmaceutically acceptable excipient.

In embodiments, the disclosure provides pharmaceutical compositions comprising a plurality of first lipid nanoparticles comprising a first nucleic acid, a plurality of second lipid nanoparticles comprising a second nucleic acid; a plurality of third lipid nanoparticles comprising a third nucleic acid wherein the plurality of the first, second, and third lipid nanoparticles are as described herein; wherein the first nucleic acid, the second nucleic acid, and the third nucleic acid are different; and wherein the first nucleic acid, second nucleic acid, and third nucleic acid are selected from the group consisting of: (a) SEQ ID NO:1 hybridized to SEQ ID NO:3 or SEQ ID NO:2 hybridized to SEQ ID NO:4; (b) SEQ ID NO:9 hybridized to SEQ ID NO: 10; (c) SEQ ID NO:11 hybridized to SEQ ID NO: 12; (d) SEQ ID NO:5 hybridized to SEQ ID NO:7 or SEQ ID NO:6 hybridized to SEQ ID NO: 8; (e) SEQ ID NO: 13 hybridized to SEQ ID NO:14; (f) SEQ ID NO:15 hybridized to SEQ ID NO: 16; and (g) SEQ ID NO:17 hybridized to SEQ ID NO:18. In embodiments, the first nucleic acid, second nucleic acid, and third nucleic acid are selected from the group consisting of: (i) SEQ ID NO:1 hybridized to SEQ ID NO:3 or SEQ ID NO:2 hybridized to SEQ ID NO:4; (ii) SEQ ID NO:9 hybridized to SEQ ID NO:10; (iii) SEQ ID NO:11 hybridized to SEQ ID NO:12; and (iv) SEQ ID NO:17 hybridized to SEQ ID NO: 18. In embodiments, the first nucleic acid is SEQ ID NO:1 hybridized to SEQ ID NO:3 or SEQ ID NO:2 hybridized to SEQ ID NO:4; the second nucleic acid is SEQ ID NO:9 hybridized to SEQ ID NO:10; and the third nucleic acid is SEQ ID NO: 11 hybridized to SEQ ID NO: 12. In embodiments, the first nucleic acid is SEQ ID NO:1 hybridized to SEQ ID NO:3; the second nucleic acid is SEQ ID NO:9 hybridized to SEQ ID NO: 10; and the third nucleic acid is SEQ ID NO:11 hybridized to SEQ ID NO:12. In embodiments, the first nucleic acid is SEQ ID NO:2 hybridized to SEQ ID NO:4; the second nucleic acid is SEQ ID NO:9 hybridized to SEQ ID NO:10; and the third nucleic acid is SEQ ID NO: 11 hybridized to SEQ ID NO:12. In embodiments, the first nucleic acid is SEQ ID NO:1 hybridized to SEQ ID NO:3 or SEQ ID NO:2 hybridized to SEQ ID NO:4; the second nucleic acid is SEQ ID NO:9 hybridized to SEQ ID NO: 10; and the third nucleic acid is SEQ ID NO: 17 hybridized to SEQ ID NO: 18. In embodiments, the first nucleic acid is SEQ ID NO:1 hybridized to SEQ ID NO:3; the second nucleic acid is SEQ ID NO:9 hybridized to SEQ ID NO: 10; and the third nucleic acid is SEQ ID NO:17 hybridized to SEQ ID NO:18. In embodiments, the first nucleic acid is SEQ ID NO:2 hybridized to SEQ ID NO:4; the second nucleic acid is SEQ ID NO:9 hybridized to SEQ ID NO:10; and the third nucleic acid is SEQ ID NO:17 hybridized to SEQ ID NO:18. In embodiments, the pharmaceutical compositions comprise a pharmaceutically acceptable excipient.

"Pharmaceutically acceptable excipient" and "pharmaceutically acceptable carrier" refer to a substance that aids the administration of an active agent to and absorption by a subject and can be included in the compositions of the disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions, alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful.

Solutions of the nucleic acids or lipid nanoparticles containing nucleic acids can be prepared in water suitably mixed with a lipid or surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions. The intranasal composition can be a spray, aerosol, or inhalant. The inhalable composition can be a spray, aerosol, or inhalant. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known in the art.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In embodiments, oral pharmaceutical compositions will comprise an inert diluent or edible carrier, or they may be enclosed in hard or soft shell gelatin capsule, or they may be compressed into tablets, or they may be incorporated directly with the food. For oral therapeutic administration, the active compounds may be incorporated with excipients and used in the form of ingestible tablets, buccal tablets, troches, capsules, elixirs, suspensions, syrups, wafers, and the like. The percentage of the compositions and preparations may, of course, be varied and may be between about 1 to about 75% of the weight of the unit. The amount of nucleic acids in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the nucleic acids in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. Dimethyl sulfoxide can be used as solvent for extremely rapid penetration, delivering high concentrations of the active agents to a small area.

The formulations of nucleic acids or lipid nanoparticles containing nucleic acids can be presented in unit-dose or multi-dose sealed containers, such as nebulizers, ventilators, ampules, and vials. Thus, the composition can be in unit dosage form. In such form the preparation is subdivided into unit doses containing appropriate quantities of nucleic acids or lipid nanoparticles containing nucleic acids. Thus, the compositions can be administered in a variety of unit dosage forms depending upon the method of administration. For example, unit dosage forms suitable for oral administration include, but are not limited to, powder, tablets, pills, capsules and lozenges.

The nucleic acids (e.g., RNA, sense RNA, antisense RNA, siRNA mRNA, DNA, plasmid, minigene), lipid nanoparticles containing nucleic acids (e.g., R RNA, sense RNA, antisense RNA, siRNA mRNA, DNA, plasmid, minigene), and pharmaceutical compositions can be administered to the patient in any manner as described herein. In embodiments, the disclosure provides a drug delivery device comprising the nucleic acids (e.g., RNA, sense RNA, antisense RNA, siRNA mRNA, DNA, plasmid, minigene), lipid nanoparticles, or pharmaceutical compositions described herein. In embodiments, the disclosure provides a nebulizer comprising the nucleic acids (e.g., RNA, sense RNA, antisense RNA, siRNA mRNA, DNA, plasmid, minigene), lipid nanoparticles, or pharmaceutical compositions described herein. In embodiments, the disclosure provides a syringe comprising the nucleic acids (e.g., RNA, sense RNA, antisense RNA, siRNA mRNA, DNA, plasmid, minigene), lipid nanoparticles, or pharmaceutical compositions described herein. In embodiments, the disclosure provides a ventilator comprising the nucleic acids (e.g., RNA, sense RNA, antisense RNA, siRNA mRNA, DNA, plasmid, minigene), lipid nanoparticles, or pharmaceutical compositions described herein.

In embodiments, the disclosure provides a ventilator which comprises a nebulizer comprising the nucleic acids (e.g., RNA, sense RNA, antisense RNA, siRNA mRNA, DNA, plasmid, minigene), lipid nanoparticles, or pharmaceutical compositions described herein. Drug delivery devices, such as nebulizers, ventilators, and syringes, are commercially available and well known in the art.

Methods of Treatment

In embodiments, the disclosure provides methods of treating COVID-19 in a subject in need thereof by administering to the subject an effective amount of a lipid nanoparticle comprising a nucleic acid (e.g., RNA, sense RNA, antisense RNA, siRNA mRNA, DNA, plasmid, minigene) that targets a nucleotide sequence of SARS-associated coronavirus 2. In embodiments, the disclosure provides methods of treating COVID-19 in a subject in need thereof by intranasally administering to the subject an effective amount of a nucleic acid (e.g., RNA, sense RNA, antisense RNA, siRNA mRNA, DNA, plasmid, minigene) that targets a nucleotide sequence of SARS-associated coronavirus 2. In embodiments, the disclosure provides methods of treating COVID-19 in a subject in need thereof by intravenously administering to the subject an effective amount of a nucleic acid (e.g., RNA, sense RNA, antisense RNA, siRNA mRNA, DNA, plasmid, minigene) that targets a nucleotide sequence of SARS-associated coronavirus 2.

In embodiments, the disclosure provides methods of treating severe acute respiratory syndrome (SARS) in a subject in need thereof by administering to the subject an effective amount of a lipid nanoparticle comprising a nucleic acid (e.g., RNA, sense RNA, antisense RNA, siRNA mRNA, DNA, plasmid, minigene) that targets a nucleotide sequence of SARS. In embodiments, the nucleic acid that targets a nucleotide sequence of SARS is any nucleic acid described herein. In embodiments, the nucleic acid that targets a nucleotide sequence of SARS is a sense strand described herein. In embodiments, the nucleic acid that targets a nucleotide sequence of SARS is any nucleic acid described herein. In embodiments, the nucleic acid that targets a nucleotide sequence of SARS is an antisense strand described herein. In embodiments, the nucleic acid that targets a nucleotide sequence of SARS is any nucleic acid described herein. In embodiments, the nucleic acid that targets a nucleotide sequence of SARS is a sense strand hybridized to an antisense strand described herein. In embodiments, the disclosure provides methods of treating severe acute respiratory syndrome (SARS) in a subject in need thereof by intranasally administering to the subject an effective amount of a nucleic acid that targets a nucleotide sequence of SARS. In embodiments, the disclosure provides methods of treating severe acute respiratory syndrome (SARS) in a subject in need thereof by intravenously administering to the subject an effective amount of a nucleic acid that targets a nucleotide sequence of SARS. In embodiments, SARS is SARS-associated coronavirus. In embodiments, SARS is SARS-associated coronavirus. In embodiments, SARS is SARS-associated coronavirus 1 (SARS-CoV-1). In embodiments, SARS is SARS-associated coronavirus 2 (SARS-CoV-2). In embodiments, SARS is Middle Eastern respiratory syndrome coronavirus (MERS-CoV).

In embodiments, the methods comprise administering an effective amount of a pharmaceutical composition comprising an pharmaceutically acceptable excipient and a lipid nanoparticle comprising a lipid and a nucleic acid described herein (e.g., a sense strand, an antisense strand, or a sense strand hybridized to an antisense strand). In embodiments, the nucleic acid is a sense strand as described herein. In embodiments, the nucleic acid is an antisense strand described herein. In embodiments, the nucleic acid is a sense strand hybridized to an antisense strand as described herein. In embodiments, one or more nucleotides in the nucleic acids comprise a modified base, a modified sugar, a modified phosphate, or a combination of two or more thereof. In embodiments, the method is for treating COVID-19. In embodiments, the method is for treating SARS-CoV-2. In embodiments, the method is for treating MERS. In embodiments, the methods comprise intranasal administration. In embodiments, the methods comprise intranasal administration with a nebulizer. In embodiments, the methods comprise intravenous administration.

Dose and Dosing Regimens

The dosage and frequency (single or multiple doses) of the nucleic acids (e.g., RNA, sense RNA, antisense RNA, siRNA mRNA, DNA, plasmid, minigene) administered to a subject can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and nucleic acids (e.g., RNA, sense RNA, antisense RNA, siRNA mRNA, DNA, plasmid, minigene) described herein. Adjustment and manipulation of established dosages (e.g., frequency and duration) are within the ability of the skilled artisan.

For any composition and nucleic acids (e.g., RNA, sense RNA, antisense RNA, siRNA mRNA, DNA, plasmid, minigene) described herein, the effective amount can be initially determined from cell culture assays. Target concentrations will be those concentrations of nucleic acids (e.g., RNA, sense RNA, antisense RNA, siRNA mRNA, DNA, plasmid, minigene) that are capable of achieving the methods described herein, as measured using the methods described herein or known in the art. As is known in the art, effective amounts of nucleic acids (e.g., RNA, sense RNA, antisense RNA, siRNA mRNA, DNA, plasmid, minigene) for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages of the nucleic acids (e.g., RNA, sense RNA, antisense RNA, siRNA mRNA, DNA, plasmid, minigene) may be varied depending upon the requirements of the patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. Dosage amounts and intervals can be adjusted individually to provide levels of the nucleic acids (e.g., RNA, sense RNA, antisense RNA, siRNA mRNA, DNA, plasmid, minigene) effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical disease or symptoms demonstrated by the particular patient. This planning should involve the careful choice of nucleic acids (e.g., RNA, sense RNA, antisense RNA, siRNA mRNA, DNA, plasmid, minigene) by considering factors such as compound potency, relative bioavailability, patient body weight, presence and severity of adverse side effects.

In embodiments, the nucleic acid (e.g., RNA, sense RNA, antisense RNA, siRNA mRNA, DNA, plasmid, minigene) is administered to a patient at an amount of about 0.001 mg/kg to about 500 mg/kg. In embodiments, the nucleic acids is administered to a patient in an amount of about 0.01 mg/kg, 0.1 mg/kg, 0.5 mg/kg, 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, or 300 mg/kg. It is understood that where the amount is referred to as "mg/kg," the amount is milligram per kilogram body weight of the subject being administered with the nucleic acid (e.g., RNA, sense RNA, antisense RNA, siRNA mRNA, DNA, plasmid, minigene). In embodiments, the nucleic acid (e.g., RNA, sense RNA, antisense RNA, siRNA mRNA, DNA, plasmid, minigene) is administered to a patient in an amount from about 0.01 mg to about 500 mg per day, as a single dose, or in a dose administered two or three times per day.

TABLE 3

| dsiRNA and siRNA sequences | | |
| --- | --- | --- |
| SIRNA | RNA sequence sense | RNA sequence antisense |
| SiRdRp1 | SEQ ID NO: 39 | SEQ ID NO: 40 |
| SiRdRp1b | SEQ ID NO: 43 | SEQ ID NO: 44 |
| SiRdRp4 | SEQ ID NO: 41 | SEQ ID NO: 42 |
| SiHel1 | SEQ ID NO: 17 | SEQ ID NO: 18 |
| SiHel2 | SEQ ID NO: 11 | SEQ ID NO: 12 |
| SIUTR1 | SEQ ID NO: 5 | SEQ ID NO: 7 |
| SIUTR3 | SEQ ID NO: 1 | SEQ ID NO: 3 |
| siUC1 | SEQ ID NO: 13 | SEQ ID NO: 14 |
| siUC2 | SEQ ID NO: 19 | SEQ ID NO: 20 |
| siUC3 | SEQ ID NO: 21 | SEQ ID NO: 22 |
| siUC4 | SEQ ID NO: 23 | SEQ ID NO: 24 |
| siUC5 | SEQ ID NO: 25 | SEQ ID NO: 26 |
| siUC6 | SEQ ID NO: 15 | SEQ ID NO: 16 |
| siUC7 | SEQ ID NO: 9 | SEQ ID NO: 10 |
| siUC8 | SEQ ID NO: 27 | SEQ ID NO: 28 |
| siUC9 | SEQ ID NO: 29 | SEQ ID NO: 30 |
| siUC10 | SEQ ID NO: 31 | SEQ ID NO: 32 |
| NC | SEQ ID NO: 70 | SEQ ID NO: 71 |
| L362 | SEQ ID NO: 72 | SEQ ID NO: 73 |
| N367 | SEQ ID NO: 74 | SEQ ID NO: 75 |
| Lamin A/C | SEQ ID NO: 76 | SEQ ID NO: 77 |

Embodiments 1 to 57

Embodiment 1. A lipid nanoparticle comprising: (i) about 30 mole % to about 45 mole % of a cationic lipid; (ii) about 10 mole % to about 30 mole % of a dilinoleic cationic lipid; (iii) about 5 mole % to about 15 mole % of a phospholipid; (iv) about 17 mole % to 30 mole % of a sterol; and (v) about 1 mole % to about 4 mole % of a polyethylene glycol-lipid conjugate.

Embodiment 2. The lipid nanoparticle of Embodiment 1 comprising: (i) about 38 mole % to about 42 mole % of the cationic lipid; (ii) about 23 mole % to about 27 mole % of the dilinoleic cationic lipid; (iii) about 8 mole % to about 12 mole % of the phospholipid; (iv) about 20 mole % to 24 mole % of the sterol; and (v) about 2 mole % to about 4 mole % of the polyethylene glycol-lipid conjugate.

Embodiment 3. The lipid nanoparticle of Embodiment 2 comprising: (i) about 40 mole % of the cationic lipid; (ii) about 25 mole % of the dilinoleic cationic lipid; (iii) about 10 mole % of the phospholipid; (iv) about 22 mole % of the sterol; and (v) about 3 mole % of the polyethylene glycol-lipid conjugate.

Embodiment 4. The lipid nanoparticle of any one of Embodiments 1 to 3, wherein the cationic lipid is DOTAP, DODAC, DODMA, DSDMA, DOTMA, DDAB, DC-Chol, DMRIE, DOSPA, DOGS, CLinDMA, CpLinDMA, DMOBA, DOcarbDAP, DOAP, C12-200, or a mixture of two or more thereof.

Embodiment 5. The lipid nanoparticle of Embodiment 4, wherein the cationic lipid is DOTAP.

Embodiment 6. The lipid nanoparticle of any one of Embodiments 1 to 5, wherein the dilinoleic cationic lipid is MC3, an MC3 derivative, DLinDMA, DLin-K-C2-DMA, DLin-K-C3-DMA, DLin-K-C4-DMA, DLin-K6-DMA, DLin-K-MPZ, DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DLin-EG-DMA, DLincarbDAP, or a mixture of two or more thereof.

Embodiment 7. The lipid nanoparticle of Embodiment 6, wherein the dilinoleic cationic lipid is MC3.

Embodiment 8. The lipid nanoparticle of any one of Embodiments 1 to 7, wherein the phospholipid is DSPC, DPPC, DOPE, POPC, POPE, POPG, DPPE, DMPE, DSPE, MMPE, DMPE, DEPE, SOPE, EPC, HSPC, or a mixture of two or more thereof.

Embodiment 9. The lipid nanoparticle of Embodiment 8, wherein the phospholipid is DSPC.

Embodiment 10. The lipid nanoparticle of any one of Embodiments 1 to 9, wherein the sterol is cholesterol, cholestanol, cholestanone, cholestenone, coprostanol, cholesteryl-2'-hydroxyethyl ether, cholesteryl-4'-hydroxybutyl ether, or a mixture of two or more thereof.

Embodiment 11. The lipid nanoparticle of Embodiment 10, wherein the sterol is cholesterol.

Embodiment 12. The lipid nanoparticle of any one of Embodiments 1 to 7, wherein the polyethylene glycol-lipid conjugate is a polyethylene glycol having a molecular weight from about 1,000 Daltons to about 6,000 Daltons conjugated to a $C_{12}$-$C_{22}$ fatty acid lipid.

Embodiment 13. The lipid nanoparticle of Embodiment 12, wherein the polyethylene glycol-lipid conjugate is C16 PEG ceramide, DMG-PEG, DPPE-PEG, DPG-PEG, DSG-PEG, DSPE-PEG, or a mixture of two or more thereof.

Embodiment 14. The lipid nanoparticle of Embodiment 13, wherein the polyethylene glycol-lipid conjugate is C16 PEG2000 ceramide.

Embodiment 15. The lipid nanoparticle of any one of Embodiments 1 to 3, wherein: (i) the cationic lipid is DOTAP; (ii) the dilinoleic cationic lipid is MC3; (iii) the phospholipid is DSPC; (iv) the sterol is cholesterol; and (v) the polyethylene glycol-conjugated lipid is C16 PEG2000 ceramide.

Embodiment 16. The lipid nanoparticle of any one of Embodiments 1 to 15, wherein a plurality of the lipid nanoparticles have an average size from about 50 nm to about 110 nm.

Embodiment 17. The lipid nanoparticle of Embodiment 16, wherein a plurality of the lipid nanoparticles have an average size from about 70 nm to about 90 nm.

Embodiment 18. The lipid nanoparticle of any one of Embodiments 1 to 17, wherein a plurality of the lipid nanoparticles have a zeta potential from about 10 mV to about 30 mV.

Embodiment 19. The lipid nanoparticle of Embodiment 18, wherein a plurality of the lipid nanoparticles have a zeta potential from about 15 mV to about 22 mV.

Embodiment 20. The lipid nanoparticle of any one of Embodiments 1 to 19, wherein a plurality of the lipid nanoparticles have a polydispersity of less than 0.27.

Embodiment 21. The lipid nanoparticle of Embodiment 20, wherein a plurality of the lipid nanoparticles have a polydispersity from about 0.12 to 0.2.

Embodiment 22. The lipid nanoparticle of any one of Embodiments 1 to 21, further comprising a nucleic acid encapsulated within the lipid nanoparticle.

Embodiment 23. The lipid nanoparticle of Embodiment 22, wherein the nucleic acid is RNA.

Embodiment 24. The lipid nanoparticle of Embodiment 23, wherein the RNA is siRNA or mRNA.

Embodiment 25. The lipid nanoparticle of Embodiment 22, wherein the nucleic acid is DNA.

Embodiment 26. The lipid nanoparticle of Embodiment 25, wherein the DNA is a plasmid or a minigene.

Embodiment 27. The lipid nanoparticle of Embodiment 22, wherein the nucleic acid comprises 15 nucleotides to 30 nucleotides and is capable of hybridizing to: (i) a target sequence in Table 1; (ii) a SARS-CoV-2 target sequence in Table 2; (iii) a SARS-CoV-1 target sequence in Table 2; or (iv) a MERS-CoV target sequence in Table 2.

Embodiment 28. The lipid nanoparticle of Embodiment 22, wherein the nucleic acid comprises 15 nucleotides to 30 nucleotides and is capable of hybridizing to SEQ ID NO:57, SEQ ID NO:51, SEQ ID NO:63, SEQ ID NO:55, SEQ ID NO:45, SEQ ID NO:50, or SEQ ID NO:62.

Embodiment 29. The lipid nanoparticle of Embodiment 27 or 28, wherein the nucleic acid comprises 20 nucleotides to 25 nucleotides.

Embodiment 30. The lipid nanoparticle of Embodiment 22, wherein the nucleic acid comprises: (a) SEQ ID NO:1 hybridized to SEQ ID NO: 3; (b) SEQ ID NO:2 hybridized to SEQ ID NO:4; (c) SEQ ID NO:9 hybridized to SEQ ID NO:10; (d) SEQ ID NO:11 hybridized to SEQ ID NO: 12; (e) SEQ ID NO:5 hybridized to SEQ ID NO:7; (f) SEQ ID NO:6 hybridized to SEQ ID NO:8; (g) SEQ ID NO: 13 hybridized to SEQ ID NO: 14; (h) SEQ ID NO: 15 hybridized to SEQ ID NO:16; (i) SEQ ID NO:17 hybridized to SEQ ID NO: 18; (j) SEQ ID NO: 19 hybridized to SEQ ID NO:20; (k) SEQ ID NO:21 hybridized to SEQ ID NO: 22; (l) SEQ ID NO:23 hybridized to SEQ ID NO:24; (m) SEQ ID NO:25 hybridized to SEQ ID NO:26; (n) SEQ ID NO:27 hybridized to SEQ ID NO:28; (o) SEQ ID NO:29 hybridized to SEQ ID NO:30; (p) SEQ ID NO: 31 hybridized to SEQ ID NO:32; (q) SEQ ID NO:33 hybridized to SEQ ID NO:34; (r) SEQ ID NO:35 hybridized to SEQ ID NO:36; (s) SEQ ID NO:37 hybridized to SEQ ID NO:38; (t) SEQ ID NO:39 hybridized to SEQ ID NO:40; (u) SEQ ID NO:41 hybridized to SEQ ID NO:42; (v) SEQ ID NO:43 hybridized to SEQ ID NO:44; or (w) a combination of two or more of the foregoing.

Embodiment 31. The lipid nanoparticle of Embodiment 30, wherein the nucleic acid comprises SEQ ID NO:1 hybridized to SEQ ID NO:3.

Embodiment 32. The lipid nanoparticle of Embodiment 30, wherein the nucleic acid comprises SEQ ID NO:2 hybridized to SEQ ID NO:4.

Embodiment 33. The lipid nanoparticle of Embodiment 30, wherein the nucleic acid comprises SEQ ID NO:9 hybridized to SEQ ID NO:10.

Embodiment 34. The lipid nanoparticle of Embodiment 30, wherein the nucleic acid comprises SEQ ID NO: 11 hybridized to SEQ ID NO:12.

Embodiment 35. The lipid nanoparticle of Embodiment 30, wherein the nucleic acid comprises SEQ ID NO:5 hybridized to SEQ ID NO:7.

Embodiment 36. The lipid nanoparticle of Embodiment 30, wherein the nucleic acid comprises SEQ ID NO:6 hybridized to SEQ ID NO:8.

Embodiment 37. The lipid nanoparticle of Embodiment 30, wherein the nucleic acid comprises SEQ ID NO: 13 hybridized to SEQ ID NO:14.

Embodiment 38. The lipid nanoparticle of Embodiment 30, wherein the nucleic acid comprises SEQ ID NO: 15 hybridized to SEQ ID NO:16.

Embodiment 39. The lipid nanoparticle of Embodiment 30, wherein the nucleic acid comprises SEQ ID NO: 17 hybridized to SEQ ID NO:18.

Embodiment 40. The lipid nanoparticle of any one of Embodiments 27 to 39, wherein the nucleic acid is siRNA.

Embodiment 41. The lipid nanoparticle of any one of Embodiments 22 to 40, wherein the nucleic acid comprises a modified base, a modified sugar, a modified phosphate, or a combination of two or more thereof.

Embodiment 42. The lipid nanoparticle of Embodiment 41, wherein the modified base is 2'O-Methyl modified base, a 2'O-methoxyethoxy modified base, a 2'fluoro modified base, a 5-methyl-modified cytidine, or pseudouridine.

Embodiment 43. The lipid nanoparticle of Embodiment 42, wherein the modified base is a 2'O-Methyl modified base.

Embodiment 44. The lipid nanoparticle of any one of Embodiments 41 to 43, wherein the modified phosphate is phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite.

Embodiment 45. The lipid nanoparticle of Embodiment 44, wherein the modified phosphate is phosphorothioate.

Embodiment 46. The lipid nanoparticle of any one of Embodiments 41 to 45, wherein the modified sugar is deoxyribose.

Embodiment 47. A plurality of the lipid nanoparticles of any one of Embodiments 1 to 46.

Embodiment 48. A pharmaceutical composition comprising the plurality of the lipid nanoparticles of Embodiment 47 and a pharmaceutically acceptable excipient.

Embodiment 49. A pharmaceutical composition comprising a plurality of first lipid nanoparticles comprising a first nucleic acid and a plurality of second lipid nanoparticles comprising a second nucleic acid; wherein the plurality of the first and second lipid nanoparticles comprise a plurality of the lipid nanoparticles of any one of Embodiments 1 to 21; wherein the first nucleic acid and the second nucleic acid are different; and wherein the first nucleic acid and second nucleic acid are selected from the group consisting of: (a) SEQ ID NO:1 hybridized to SEQ ID NO:3 or SEQ ID NO:2 hybridized to SEQ ID NO:4; (b) SEQ ID NO:9 hybridized to SEQ ID NO: 10; (c) SEQ ID NO: 11 hybridized to SEQ ID NO:12; (d) SEQ ID NO:5 hybridized to SEQ ID NO:7 or SEQ ID NO:6 hybridized to SEQ ID NO:8; (e) SEQ ID NO: 13 hybridized to SEQ ID NO:14; (f) SEQ ID NO: 15 hybridized to SEQ ID NO: 16; and (g) SEQ ID NO: 17 hybridized to SEQ ID NO:18.

Embodiment 50. The pharmaceutical composition of Embodiment 49, further comprising a plurality of third lipid nanoparticles comprising a third nucleic acid; wherein the plurality of the third lipid nanoparticles comprise a plurality of the lipid nanoparticles of any one of Embodiments 1 to 21; wherein the first nucleic acid, the second nucleic acid, and the third nucleic acid are different; and wherein the third nucleic acid is selected from the group consisting of: (a) SEQ ID NO:1 hybridized to SEQ ID NO:3 or SEQ ID NO:2 hybridized to SEQ ID NO:4; (b) SEQ ID NO:9 hybridized to SEQ ID NO:10; (c) SEQ ID NO:11 hybridized to SEQ ID NO:12; (d) SEQ ID NO:5 hybridized to SEQ ID NO:7 or SEQ ID NO:6 hybridized to SEQ ID NO: 8; (e) SEQ ID NO: 13 hybridized to SEQ ID NO:14; (f) SEQ ID NO: 15 hybridized to SEQ ID NO: 16; and (g) SEQ ID NO:17 hybridized to SEQ ID NO:18.

Embodiment 51. The pharmaceutical composition of Embodiment 50, wherein the first nucleic acid comprises SEQ ID NO:1 hybridized to SEQ ID NO:3 or SEQ ID NO:2 hybridized to SEQ ID NO:4; the second nucleic acid comprises SEQ ID NO:9 hybridized to SEQ ID NO:10; and the third nucleic acid comprises SEQ ID NO:11 hybridized to SEQ ID NO:12.

Embodiment 52. The pharmaceutical composition of Embodiment 50, wherein the first nucleic acid comprises SEQ ID NO:1 hybridized to SEQ ID NO:3 or SEQ ID NO:2 hybridized to SEQ ID NO:4; the second nucleic acid comprises SEQ ID NO:9 hybridized to SEQ ID NO:10; and the third nucleic acid comprises SEQ ID NO:17 hybridized to SEQ ID NO:18.

Embodiment 53. A method for administering a lipid nanoparticle to a lung of a patient in need thereof, the method comprising administering to the patient the lipid nanoparticle of any one of Embodiments 1 to 46, the plurality of the lipid nanoparticles of Embodiment 47, or the pharmaceutical composition of any one of Embodiments 48 to 52.

Embodiment 54. A method for treating a SARS coronavirus infection in a patient in need thereof, the method comprising administering to the patient the lipid nanoparticle of any one of Embodiments 24 to 46, the plurality of the lipid nanoparticles of Embodiment 47, or the pharmaceutical composition of any one of Embodiments 48 to 52.

Embodiment 55. The method of Embodiment 54, wherein the SARS coronavirus infection is SARS-CoV-1, SARS-CoV-2, or MERS-CoV.

Embodiment 56. A method for treating COVID-19 in a patient in need thereof, the method comprising administering to the patient the lipid nanoparticle of any one of Embodiments 24 to 46, the plurality of the lipid nanoparticles of Embodiment 47, or the pharmaceutical composition of any one of Embodiments 48 to 52.

Embodiment 57. The method of any one of Embodiments 53 to 56, comprising intravenously administering to the patient the lipid nanoparticle, the plurality of the lipid nanoparticles, or the pharmaceutical composition.

Example

Coronavirus disease 2019 (COVID-19) is caused by SARS-CoV-2 infection in humans. Despite several emerging vaccines, there remains no verifiable therapeutic targeted specifically to the virus. Here we present a highly effective siRNA therapeutic against SARS-CoV-2 infection using a novel lipid nanoparticle delivery system. Multiple small-interfering RNAs (siRNAs) targeting highly conserved regions of the SARS-CoV-2 virus were screened and candidate siRNAs emerged that effectively inhibit virus by greater than 90% either alone or in combination with one another. We developed and screened novel lipid nanoparticle formulations for the delivery of these candidate siRNA therapeutics to the lungs, an organ that incurs immense damage during SARS-CoV-2 infection. Our LNP-siRNA approaches are scalable and can be administered upon the first sign of SARS-CoV-2 infection in humans. This siRNA-LNP therapeutic approach will be highly useful in treating COVID-19 disease as an adjunctive therapy to current vaccine strategies.

Introduction

Coronaviruses have been previously linked to public health crises including the SARS-CoV-1 outbreak in 2003 and the Middle East Respiratory Coronavirus (MERS-CoV) in 2012. These viruses led to approximately 8,096 infections for SARS-CoV-1 and 1,728 infections for MERS (WHO reports, 2004 and 2016). In contrast, the highly transmissible novel SARS-CoV-2 virus quickly escalated to a pandemic with over 117 million cases reported worldwide along with multi-organ failure, acute respiratory distress syndrome and death in the elderly and in those with underlying morbidities. The race to develop a SARS-CoV-2 vaccine began swiftly and is ongoing, however the emergence of viral variants has demonstrated the limited effectiveness of some vaccines to these variants. These observations suggest an urgent and unmet need for SARS-CoV-2 specific therapies to treat COVID-19. While dexamethasone and remdesivir appear to provide some benefit to COVID-19 patients (3), a therapeutic targeted to directly inhibit SARS-CoV-2 is lacking.

RNA encodes the genome of Coronaviruses, rendering them highly susceptible to RNA interference, particularly when delivered to the lungs of primates. Small interfering RNAs (siRNAs) are short double stranded RNA molecules that induce gene silencing at the transcriptional or post-transcriptional level and can be delivered to the lungs through either intranasal or intravenous routes. We report here the screening of several siRNAs targeted to highly conserved regions of SARS-COV-2 that block virus expression and replication. The siRNAs will be able to functionally repress virus expression in vivo and inhibit the emergence of COVID-19 disease when delivered (e.g., intravenously) using lipid nanoparticle (LNP) siRNA formulations.

Example 1 siRNA Targeting SARS-CoV-2

To determine the effectiveness of RNAi to SARS-CoV-2 we designed several siRNAs targeted to the ultra-conserved regions in the RNA dependent RNA Polymerase (RdRp), Helicase (Hel), and 5' untranslated leader region (5'UTR). Ultra-conserved siRNAs that target structurally accessible regions were (a) discovered by characterizing the 29,903 bp RNA genome of SARS-CoV-2 for structural features sequence conservation, (b) RNA modifications and (c) the absence of seed sequences in the human transcriptome. Andrews et al., An in silico map of the SARS-CoV-2 RNA Structurome. bioRxiv, 2020; Rangan et al, RNA 26, 937-959 (2020); Kim et al, Cell 181, 914-921 e910 (2020). We used these data to prioritize approximately 9,500 candidate siR-NAs generated by OligoWalk (Mathews, 2010 #4459) and DSIR (Vert, 2006 #4460). In addition, 163 experimentally validated SARS-CoV-1 siRNAs were assessed for homology with SARS-CoV-2 (Thakur, 2012 #4461). From this stringent bioinformatic approach the siRNAs in Table 1 were selected for further testing.

Chemical modifications can be used to stabilize siRNAs, which results in a longer-term expression and persistence in vivo that results in more potent repression. Selvam et al, Chem Biol Drug Des 90, 665-678 (2017). We selected siUTR3, as this target site resides in stem loop 1, a highly conserved region in the 5'UTR required for downstream transcriptional processing and expression of several viral RNAs. Miao et al, RNA Biol 18, 447-456 (2021).

Lipid Nanoparticle In Vivo Delivery of Anti-SARS-COV-2 siRNAs

Developing therapeutic strategies for viral infections based on siRNAs has so far proved challenging, with poor clinical success primarily being the result of subpar delivery. SARS-CoV-2 infection occurs predominantly in epithelial cells of the respiratory tract and results in diffuse alveolar damage. Macrophage and monocytes are also infected with SARS and may be one source of the observed cytokine storm in COVID-19 disease. We previously developed an intravenous liposome delivery platform that resulted in robust delivery of siRNAs to the lungs in vivo. Unlike standard liposomes, these "stealth" lipid nanoparticles (sLNPs) are formulated to be stable in serum, circulate for long periods of time, and to protect siRNA payloads from nucleases. These liposomes can be formulated based on alterations of size and composition to traffic to the lung. Hu et al, Nat Rev Microbiol 19, 141-154 (2021); Yilla et al., Virus Res 107, 93-101 (2005); Channappanavar et al, Semin Immunopathol 39, 529-539 (2017); McCray, Jr. et al., J Virol 81, 813-821 (2007); McCaskill et al., Mol Ther Nucleic Acids 2, e96 (2013); Wu et al., Pharm Res 26, 512-522 (2009).

Previously published work fully characterized the sLNPs with an average size of 190 nm, polydispersity index of 0.326, zeta potential of 52.1 millivolts (mV), and 94.8% siRNA encapsulation efficiency. Additionally, this work demonstrated that sLNPs can target the lung (about 35%), liver (about 55%) and spleen (about 10%). Recent studies have found that increased concentrations of 1,2-dioleoyl-3-trimethylammonium-propane (DOTAP) with DLin-MC3-DMA (MC3) into the LNP formulations results in enhanced targeting to the lung. As such we sought to contrast earlier formulated sLNPs containing 50% DOTAP with next generation modified LNPs containing 40% DOTAP+MC3 (dmLNP) for delivery of anti-SARS-CoV-2 siRNAs in vivo. McCaskill et al, Mol Ther Nucleic Acids 2, e96 (2013); Wu et al, Pharm Res 26, 512-522 (2009); Cheng et al., Nat Nanotechnol 15, 313-320 (2020).

We screened a panel of formulations with reduced DOTAP at 40 mole %, 35 mole %, and 30 mole %, as shown in Table 4. Our goal was to develop a next generation 'stealth LNP' formulation with reduced DOTAP and in turn incorporate the cationic ionizable lipid MC3 to help facilitate the endosomal release of siRNAs. The numbers in Table 4 are mole %.

TABLE 4

| Formulation Name | DOTAP | MC3 | DSPC | Cholesterol | C16 PEG200 ceramide |
|---|---|---|---|---|---|
| DOTAP 40 | 40 | 10 | 10 | 37 | 3 |
| DOTAP 35 | 35 | 15 | 10 | 37 | 3 |
| DOTAP 30 | 30 | 20 | 10 | 37 | 3 |
| dmLNP (DOTAP 40C) | 40 | 25 | 10 | 22 | 3 |

Figure 2A:
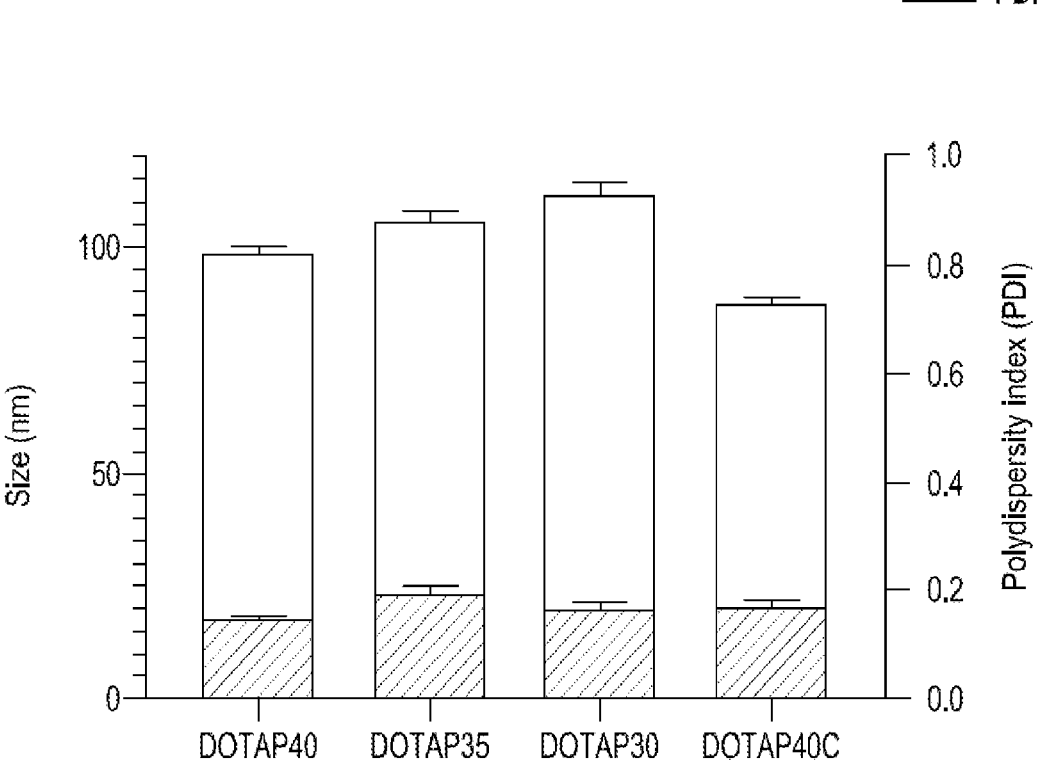
FIGS. 2A-2D provide data on reduced DOTAP nanoparticle formulations.
Figure 2B:
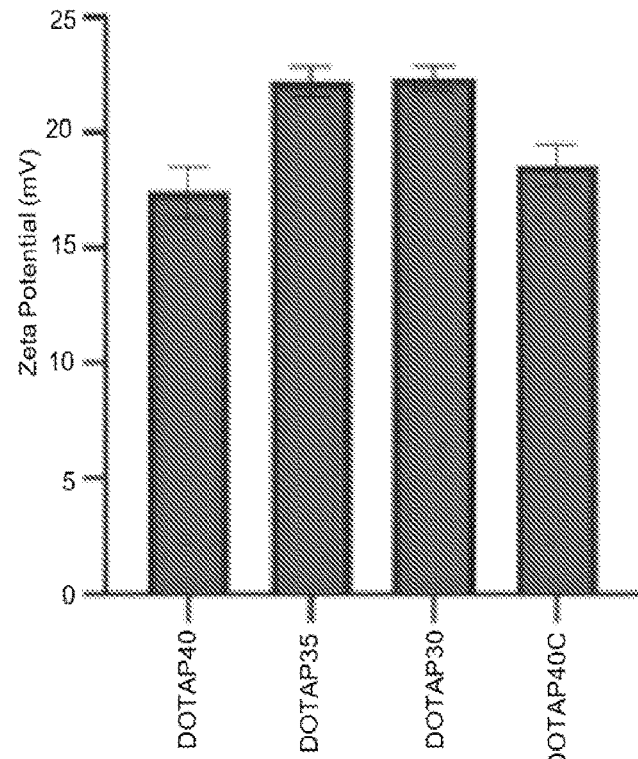
Figure 2C:
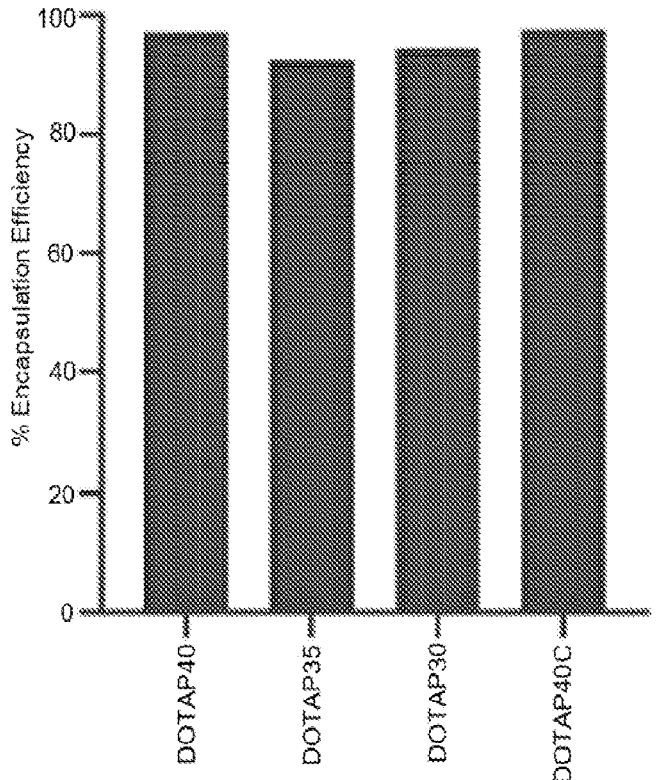
Figure 2D:
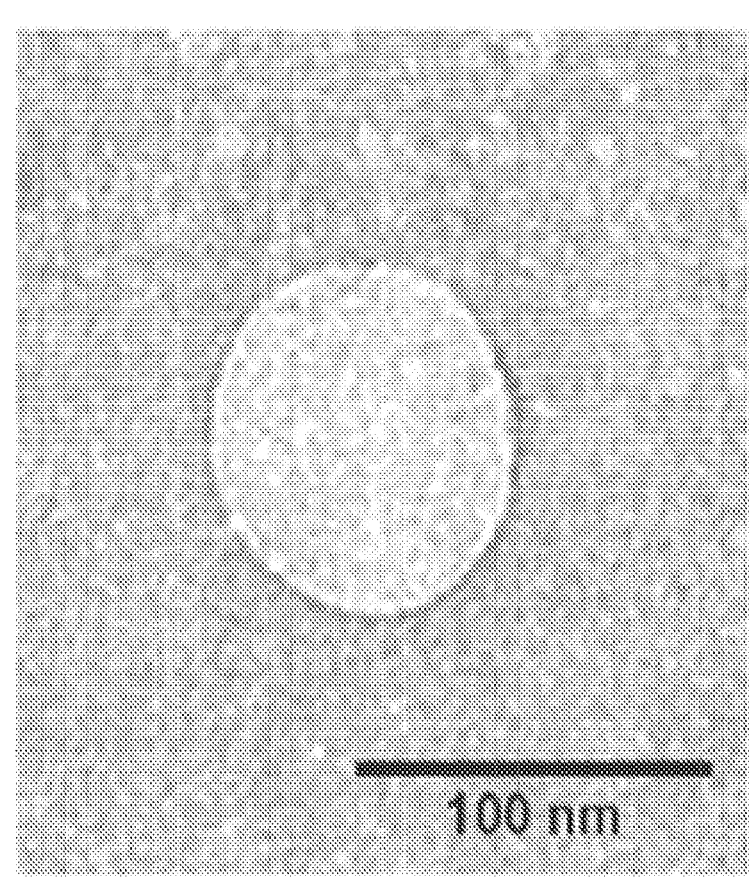

We observe that our DOTAP LNP formulations range from 80 to 115 nm in size and display low polydispersity values (FIG. 2A). The zeta potential of our reduced DOTAP LNP formulations range from 17 to 23 mV (FIG. 2B). Notably, there was little difference in the zeta potential values between these new formulations despite the stepwise reduction in DOTAP (FIG. 2B). Because highly positive surface charges of nanoparticles and liposomes are linked to toxicity we view our reduction in surface charge as compared to the previous sLNP-siRNA formulation as a favorable step toward reducing potential toxicity. Furthermore, all formulations in the panel had ≥92% encapsulation efficiency of siRNA cargo (FIG. 2C) and transmission electron microscope imaging of the DOTAP40 LNPs (LNPs containing 40 mole % DOTAP) exhibited a uniform spherical shape (FIG. 2D). Xue et al, Nanomedicine (Lond) 9, 295-312 (2014).

Figure 1B:
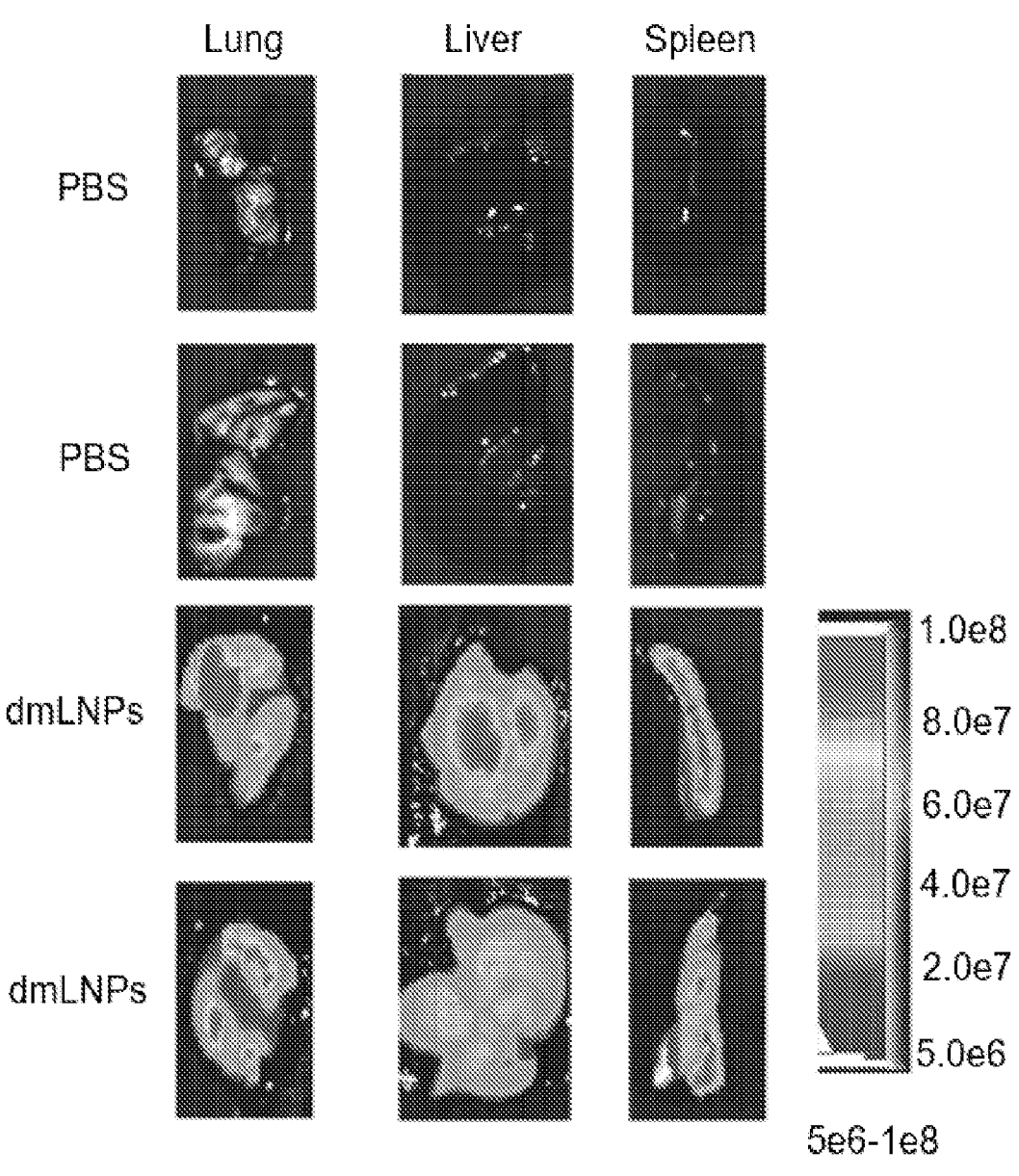
Figure 1C:
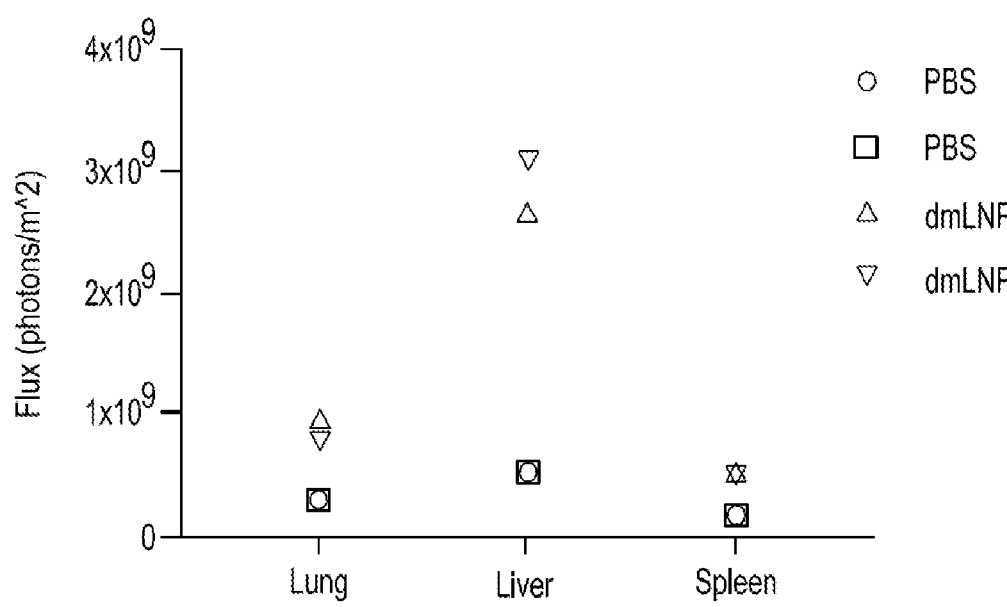
Figure 3A:
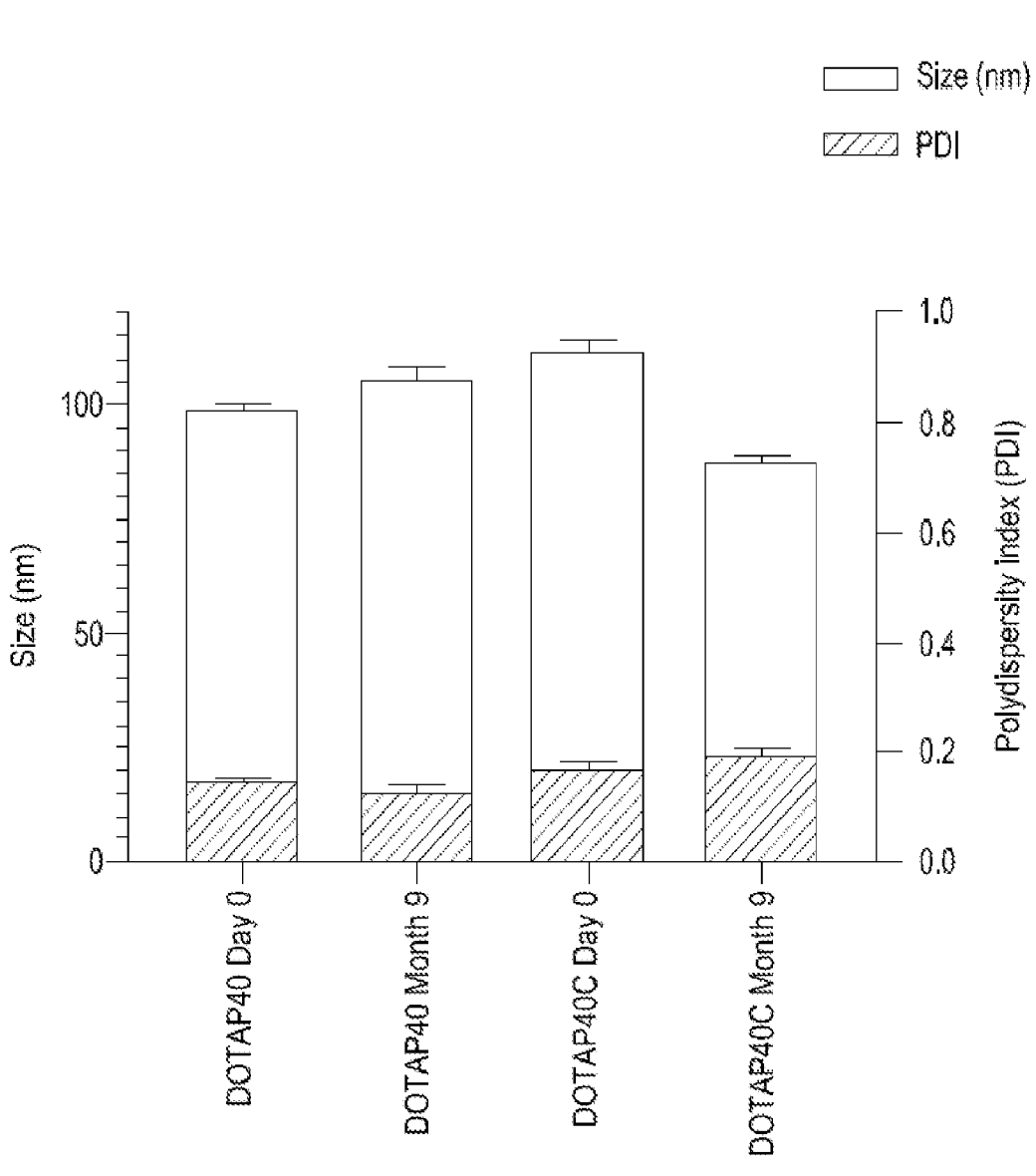
FIGS. 3A-3D provide stability evaluations of DOTAP40 and DOTAP40C nanoparticles.
Figure 3B:
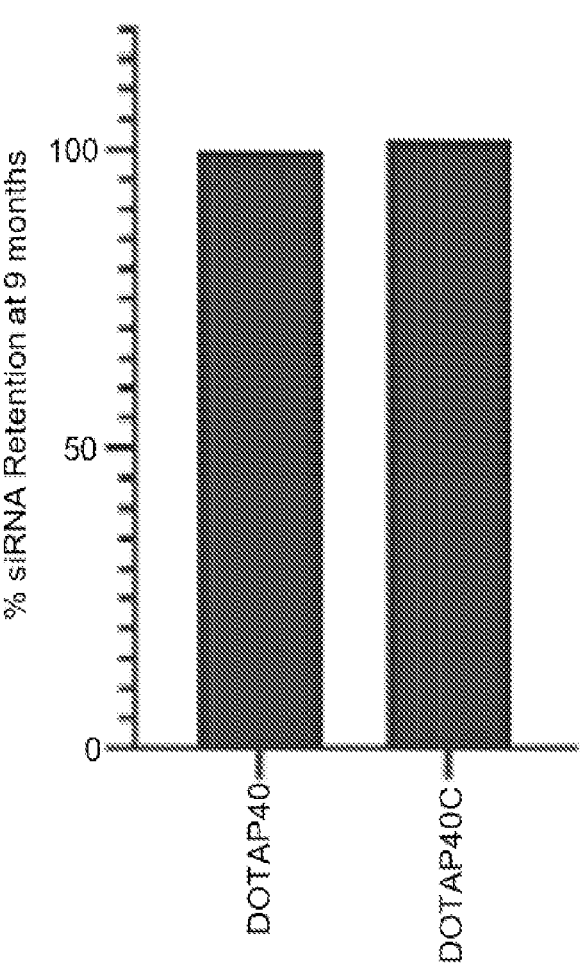
Figure 3C:
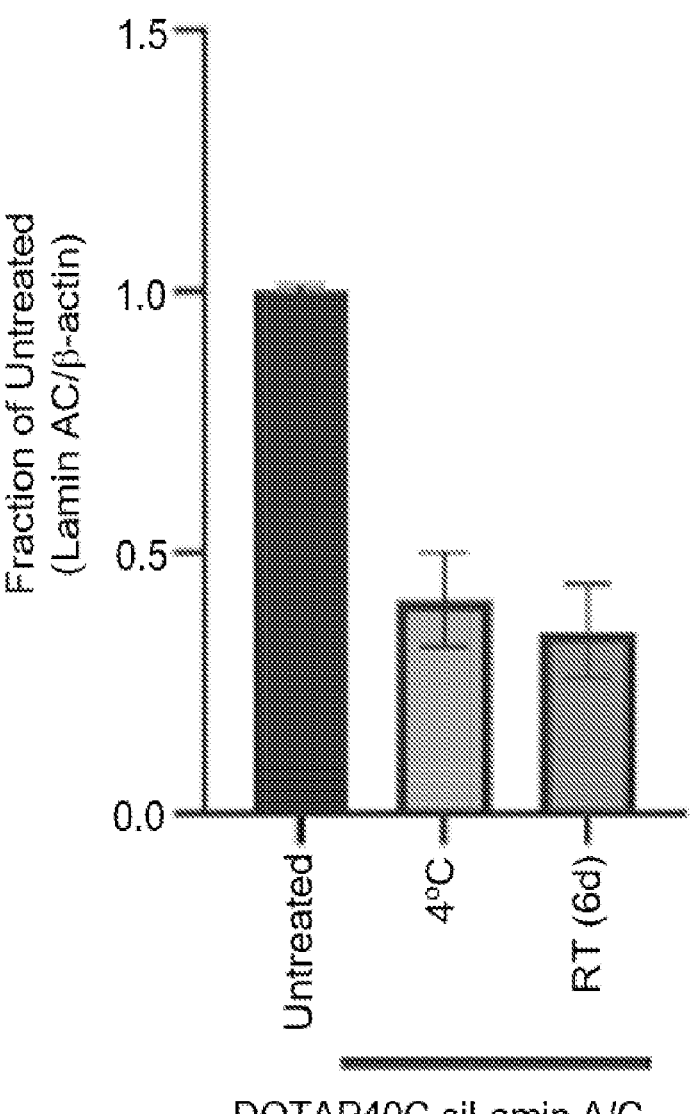
Figure 3D:
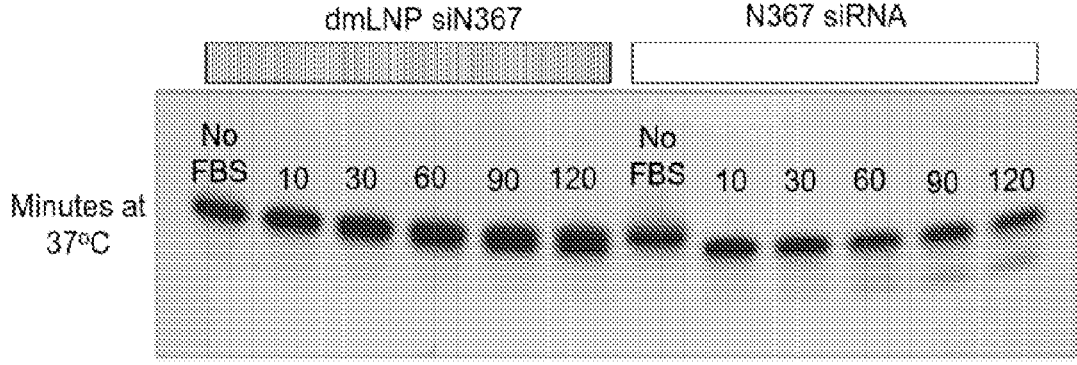
Figure 4A:
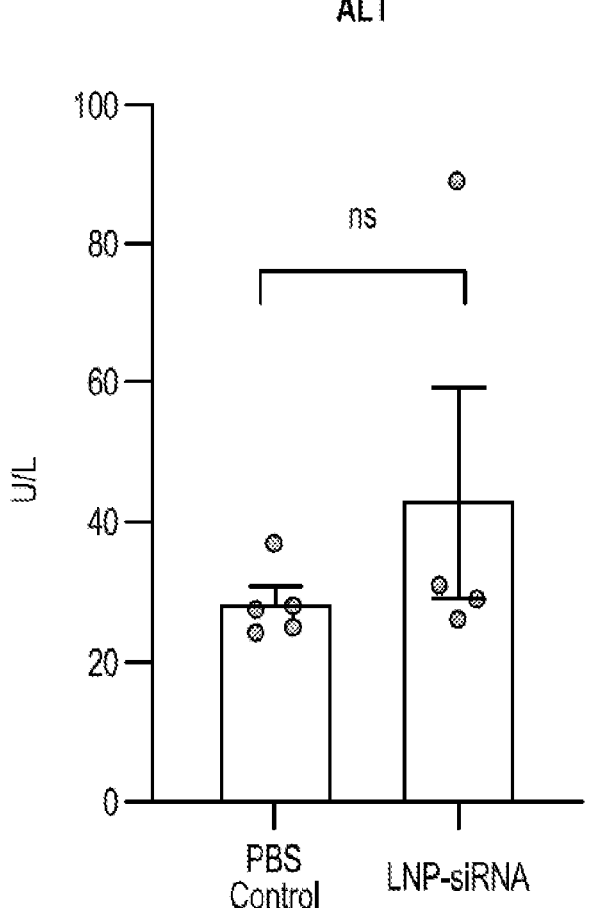
FIGS. 4A-4D: Evaluating DOTAP 40C LNP safety profile. C57BL/6 mice were evaluated for liver toxicity and cytokine levels after a 2.5 mg/kg dose of DOTAP 40C LNPs (LNP-siRNA) or PBS vehicle control by intravenous administration. A universal negative control (NC) siRNA was encapsulated in DOTAP 40 LNPs for this study. Twenty-four hours post administration whole blood was collected and was evaluated for liver toxicity using a VetScan Mammalian Liver Profile kit. Serum concentration of alanine aminotransferase (ALT) (FIG. 4A), aspartate aminotransferase (AST) (FIG. 4B), blood urea nitrogen (BUN) (FIG. 4C), and creatine (CREA) (FIG. 4D) are reported. Data presented as mean±S.E.M for n=5 for PBS mice and n=4 for LNP-siRNA mice. Significance was determined using an unpaired, two-tailed t-test; ns=not significant, *** p<0.001.
Figure 4B:
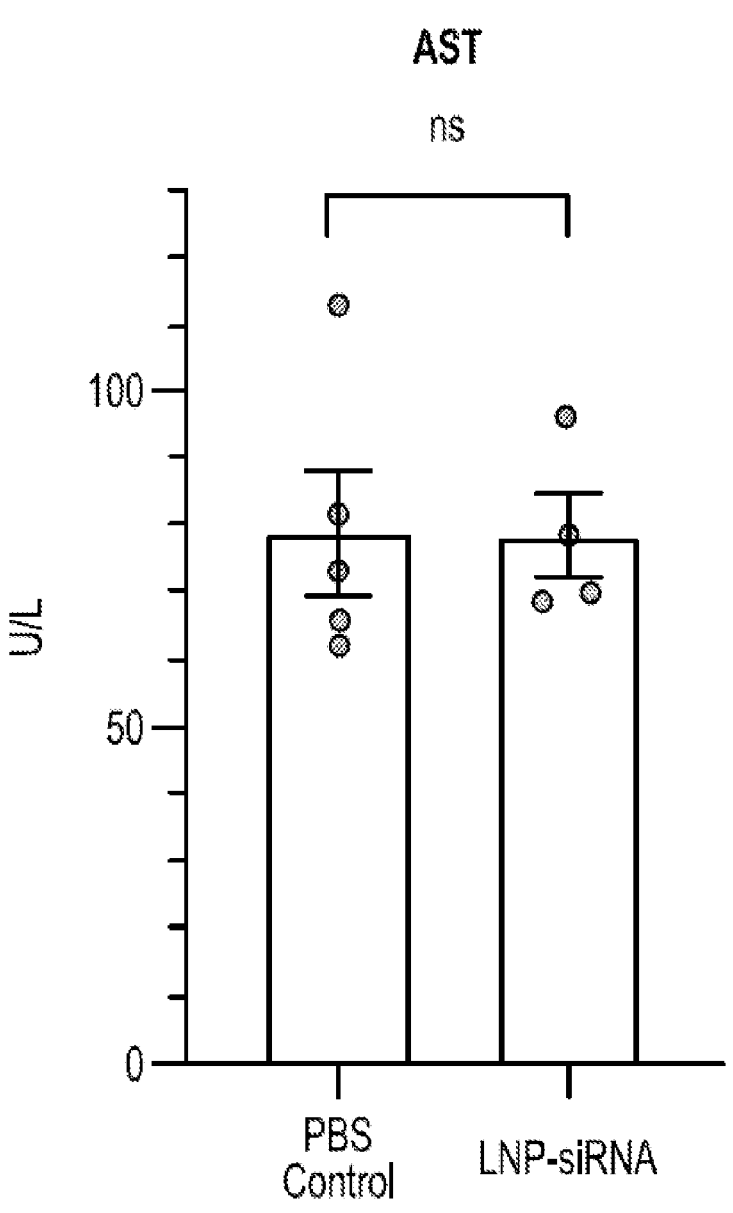
Figure 4C:
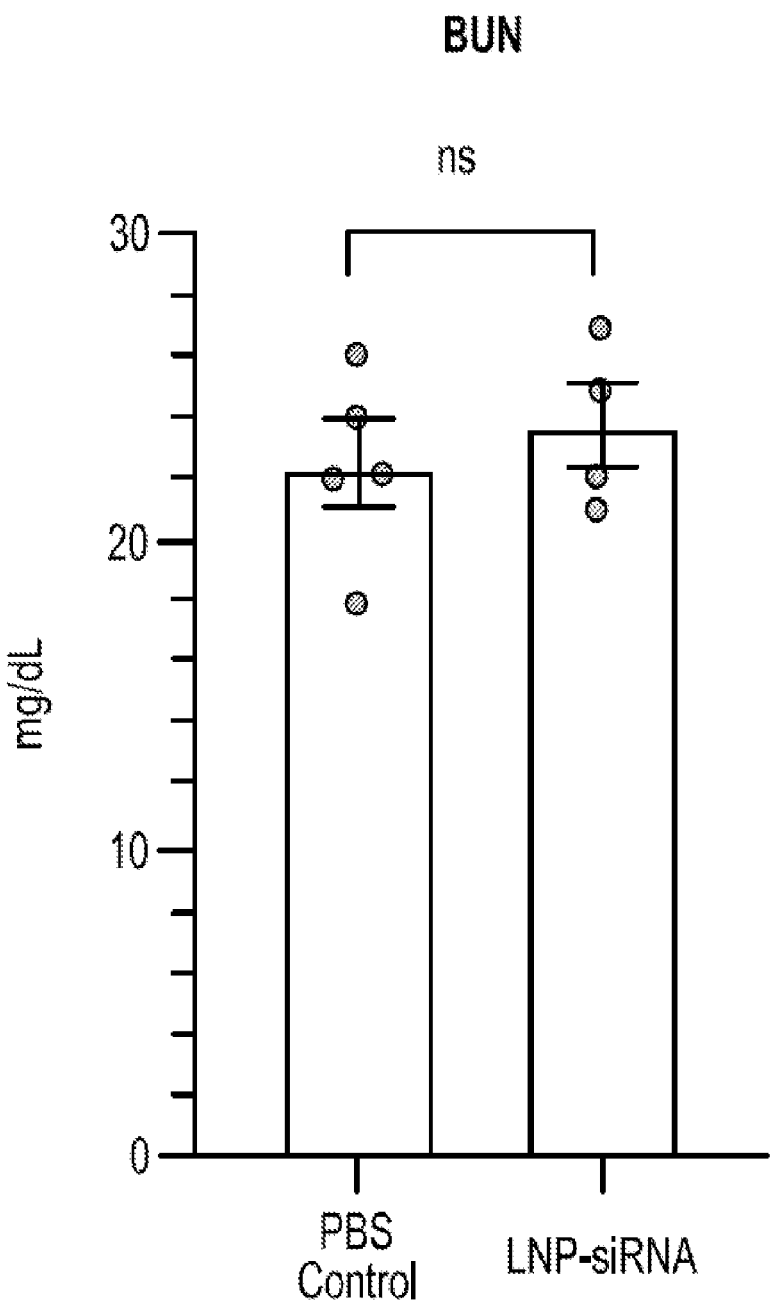
Figure 4D:
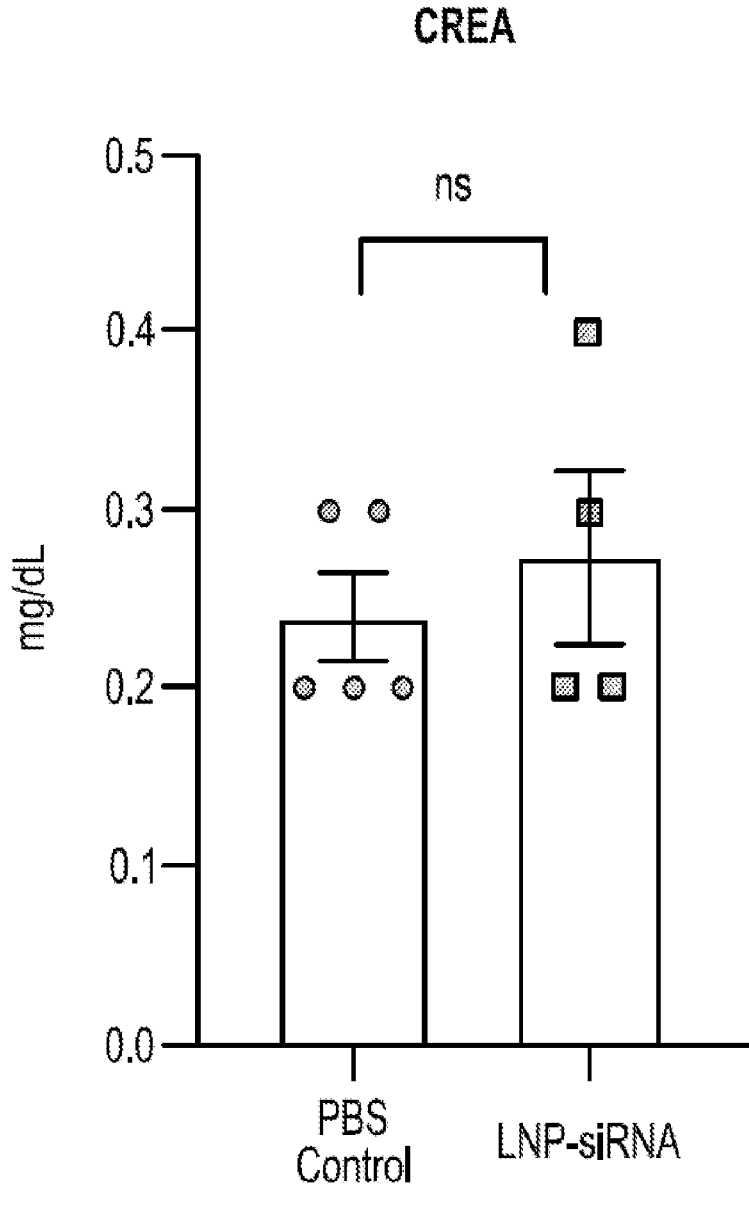

Notably, the DOTAP40 and DOTAP40C LNPs remain stable for at least 9 months when stored at 4° C. with nearly 100% retention of encapsulated siRNA (FIGS. 3A-3B) and DOTAP40C LNPs retain function after six days at room temperature. Furthermore, the siRNAs are largely resistant to enzymatic degradation when encapsulated in these LNPs (FIGS. 3C-3D). Based on these observations we selected the "DOTAP40C" formulation which contains the highest proportion of MC3 while also retaining a high proportion of DOTAP which is important for achieving lung delivery of the candidate SARS-CoV-2 siRNAs. To determine the ability of these newly formulated DOTAP/MP3 LNP-siRNAs (dmLNP-siRNAs, formerly identified as DOTAP40C) to effectively target the lung, DiD labelled dmLNP-siRNA formulations (Table 5) were generated and found to be about 80 nm (FIG. 1A) with a zeta potential of about 18.58 mV and to encapsulate ≥97% of the control siRNAs (Table 6). When injected IV into mice and assessed 24 hrs later there was localization of DiD fluorescence in the lung (21%), liver (67%) and less so in the spleen (12%) (FIGS. 1B-1C), which was similar to previous observations with sLNPs. McCaskill et al., Mol Ther Nucleic Acids 2, e96 (2013); Wu et al., Pharm Res 26, 512-522 (2009).

TABLE 5

| dmLNP | |
| --- | --- |
| Lipid Component | Molar % |
| DOTAP | 40 |
| MC3 | 25 |
| DSPC | 10 |
| Cholesterol | 22 |
| C16-PEG200-ceramide | 3 |

TABLE 6

| Characteristics of Table 5 Nanoparticle | |
| --- | --- |
| Characteristic | |
| Average Size | 80 nm |
| Polydispersity (PDI) | 0.16 |
| Zeta Potential | 18.58 mV |
| siRNA Encapsulation Efficiency | 97.6% |

Discussion

Currently there are scant antivirals reported which directly target SARS-CoV-2 RNA genome. CRISPR has recently been used to target SARS-CoV-2, but pre-existing antibodies to CRISPRs and the need to translate the packaged CRISPR mRNA and gRNA in virus infected cells will hinder the clinical translation of this approach. RNAi does not require translation of mRNA, is programmable, scalable, sTable lnd has been observed to potently repress coronaviruses. RNAi and particular siRNAs, siHel1, siHel2, UC7 and siUTR3 will significantly repress SARS-COV-2 in vitro and in vivo and will be a useful therapeutic to treating COVID-19 disease. However, delivery of siRNAs to sites of disease, such as the lungs in COVID-19 afflicted individuals, has remained enigmatic. Blanchard et al., Treatment of influenza and SARS-CoV-2 infections via mRNA-encoded Cas13a in rodents. Nat Biotechnol, (2021); Charlesworth et al., Nat Med 25, 249-254 (2019); Wu et al, Antiviral Res 65, 45-48 (2005); Shi et al., Cell Res 15, 193-200 (2005); Wu et al, Expert Opin Investig Drugs 15, 89-97 (2006).

The persistent cough and shortness of breath endemic in COVID-19 disease highlight the lungs as a site of significant stress and inflammation during SARS-CoV-2 infection. The thick mucosa associated with COVID-19 will likely impede the delivery of aerosolized therapeutics to infected tissues and additionally, nebulizers increase droplet dispersion which could lead to infectious particles remaining in the air thereby increasing the risk of the disease spreading. For these reasons we surmised that an IV route of administration as a backdoor delivery system, might prove both safe and effective. Building on this notion we turned to "stealth"

LNPs, which have been shown to deliver siRNAs to the lung, liver and spleen following an IV administration. McCaskill et al., Mol Ther Nucleic Acids 2, e96 (2013); Wu et al., Pharm Res 26, 512-522 (2009).

Recent work by Cheng et al., Nat Nanotechnol 15, 313-320 (2020) demonstrated that LNP formulations can be tuned to specifically target the lung by adjusting the amount of DOTAP incorporated into the particles. Increasing the DOTAP concentration to greater than 50 mole % has been reported to result in lung specific expression of a luciferase mRNA reporter. Notably, this group used a combination of DOTAP (50 mole %) and MC3 (25 mole %) to achieve efficient LNP lung targeting. Our sLNP-siRNAs containing 50 mole % DOTAP and no MC3 target the lung, however we find the liver and spleen are also targeted. Our dmLNP-siRNAs contain 40 mole % DOTAP and 25 mole % MC3, but also display targeting of the lung, liver and spleen. Notably, the dmLNP-siRNAs (Table 5) contained 40 mole % DOTAP and exhibited a concomitant reduction in lung targeting when administered IV, regardless of the MC3 incorporation, suggesting that DOTAP is the key component to targeting the lung with LNPs. DOTAP is a cationic lipid that contributes to the positive surface charge of liposomes and LNPs, and has been shown to activate the immune system resulting in systemic toxicity. By reducing the amount of DOTAP in our dmLNP-siRNAs we have reduced the positive surface charge on the particles by approximately half compared to the sLNP-siRNAs. McCaskill et al., Mol Ther Nucleic Acids 2, e96 (2013); Wu et al., Pharm Res 26, 512-522 (2009); Kedmi et al, Biomaterials 31, 6867-6875 (2010). Our data indicate that minimal 2'OMethyl and phosphorothioate modifications are sufficient to increase the stability of the tested dsiRNA (UTR3) in vitro.

The SARS-CoV-2 vaccine race led by Pfizer-BioNTech and Modema has opened the door for future LNP based therapies. Both Pfizer-BioNTech and Modema vaccines (BNT162b2 and mRNA-1273, respectively) contain an mRNA encoding the spike protein encapsulated in an LNP delivery vehicle. Prior to the pandemic, the only FDA approved LNP based therapy was the siRNA-LNP drug patisiran (ONPATTRO® by Alnylam) used for the treatment of polyneuropathy caused by hereditary transthyretin-mediated amyloidosis. Recent successes in the clinical translation of LNPs portend a new era in nanomedicine, whereby LNPs are now viewed favorably as bonafide and safe delivery vehicles for mRNAs and RNAi. Building on this realized consensus of interpretation we will show that IV administered stealth LNPs will deliver siRNAs as a therapeutic to treat COVID-19.

Materials and Methods

Lipids/Reagents:

The following lipids 1,2-dioleoyl-3-trimethylammonium-propane (DOTAP), 1,2-distearoyl-sn-glycero-3-phosphocholine (DSPC), cholesterol, N-palmitoyl-sphingosine-1-{succinyl[methoxy(polyethylene glycol)2000]} (C16 PEG2000 Ceramide) were purchased from Avanti Polar Lipids (Alabaster, AL, USA). DLin-MC3-DMA was purchased from (MedChemExpress; Monmouth Junction, NJ, USA). All lipids were dissolved in ethanol and aliquoted in amber glass vials. Lipophilic dye DiL (DilC$_{18}$(3) or DiD (DilC$_{18}$(5) (1,1'-dioctadecyl-3,3,3',3'-tetramethylindocarbocyanine perchlorate) at 1 mM stock in ethanol (Invitrogen; Carlsbad, CA, USA) was used to label nanoparticles at 0.5 μM for biodistribution studies.

dmLNP Synthesis:

Lipids were prepared at a 40:25:10:22:3 (DOTAP:MC3: DSPC:cholesterol:(C16-PEG200-ceramide)) molar ratio. Lipids in ethanol were mixed with nucleic acids in an aqueous phase at a mol cationic lipid:mol RNA (N:P) ratio of 3:1 using the NanoAssemblr Benchtop machine (Precision NanoSystems; Vancouver, BC, Canada). This machine contains a microfluidic chip by which the injected lipids and nucleic acids are mixed rapidly in a staggered herringbone pattern at a total flow rate of 12 mL/min. The controlled mixing of the aqueous and organic streams produces homogeneous nanoparticles. Immediately following the mixing process, the nanoparticles were diluted 1:4 with 1×PBS to reduce the amount of ethanol present in solution. The nanoparticle solution was further diluted with 1×PBS up to 15 mL and then concentrated using a 10 kDa Amicon ultra-15 filter (Millipore; Burlington, MA, USA) via centrifugation at 2,000×G for 30 minutes. The flow through was discarded and another 15 mL 1×PBS was added to the column and centrifuged at 2,000×G for 40 mins. The concentrated nanoparticles were then pushed through a 0.22 μm filter and stored at 4° C.

Characterization of dmLNPs:

Nanoparticles were analyzed using dynamic light scattering (DLS) to determine polydispersity (PDI) and surface charge was determined by measuring zeta potential on a ZetaPals (Brookhaven Instruments Corporation; Holtsville, NY, USA). Concentration and relative nanoparticle size was determined using nanoparticle tracking analysis (NTA) on the Nanosight (NS300) (Malvern Panalytical; Malvern, UK) and the qNANO Gold (IZON; Christchurch, New Zealand). For the NTA, samples were diluted 10,000×× in PBS and samples measured in triplicate technical replicates. A blue 488 laser was used to detect the LNPs, with a slide shutter level set to 1200× and the slider gain set to 146Y, and the syringe pump speed set to 30 using a flow-cell top plate module. For the qNano, a NP150 nanopore (iZON; Christchurch, New Zealand) was used to measure the LNPs. LNPs were diluted 40× in measuring solution measured at 2 different pressures. Concentration was determined by measuring calibration beads at known concentrations and extrapolating particles/mL for each sample evaluated using the iZON control suite software (V3.4.2.48name, version).

To measure the amount of siRNA encapsulated inside the nanoparticles the Quant-IT Ribogreen assay was carried out (Molecular Probes; Eugene, OR, USA). The standard protocol was modified to include a 15 minute, 37° C. incubation of the nanoparticles in the presence of 2% Triton to facilitate release of the encapsulated nucleic acids. % encapsulation= (siRNA-LNP in 2% Triton−siRNA-LNP in TE)/siRNA-LNP in 2% Triton-X100 (based on Leung 2012, PMID: 22962627).

siRNAs:

siRNAs or dsiRNAs targeted to SARS-CoV-2 were ordered from Integrated DNA Technologies (Coralville, IA, USA) as duplexed RNA. Target sequences for siRNAs are listed in Table 1 and Table 3. The negative control (NC) dsiRNA was purchased from IDT. Control siRNAs, N367 and L362 were designed towards the miRNA-N367 target site and the 5'LTR of HIV-1 respectively, and were synthesized as duplexed RNA by IDT. Sequences for all dsiRNAs and siRNAs employed in this study are in Table 1 and Table 3. modUTR3 was designed and synthesized by IDT as an RNA duplex. HPLC purified and high quantity dsiRNAs and siRNAs, UTR3, Hel2, UC7, N367 were synthesized by the RNA/DNA Synthesis core at the City of Hope (Duarte, CA) and used in the in vivo experiments. You et al, PLoS One 7, e36157 (2012); Omoto et al, J Gen Virol 86, 751-755 (2005); Omoto et al, Methods Mol Biol 342, 255-265 (2006); Turner, Ackley, Matrone, and Morris, Hum Gene Ther 23, 473-483 (2012); Weinberg et al., RNA 12, 256-262 (2006).

dmLNP-siRNA Uptake Evaluation In Vivo:

All animal experiments were approved by the City of Hope IACUC (20025). To determine if siRNA loaded nanoparticles show preferential lung accumulation we injected C57/BL6 mice IV with DiD-labeled nanoparticles at 1 mg/kg siRNA dose. 24 hours after injection, mice were euthanized and the lung, liver, and spleen were removed. Organs were imaged for DiD fluorescence using a LagoX imager (Spectral Instruments Imaging, AZ) at an excitation and emission wavelength of 640 and 690 nm, respectively.

Long-Term Stability:

To determine the long-term stability of our LNPs we evaluated size and polydispersity using DLS and monitored siRNA encapsulation at 9 months post formulation.

qRTPCR and gene expression analysis: To evaluate the in vitro activity of LNPs carrying Lamin A/C siRNA, RT-qPCR analysis was carried out. RNA was isolated using the Maxwell RSC purification kit (Promega; Madison, WI, USA). A total of 10 ng of RNA was used in Luna Universal One-Step RT-qPCR analysis (NEB; Ipswich, MA, USA) for Lamin A/C (SEQ ID NO:79) and (SEQ ID NO:80) and R-actin (SEQ ID NO:81) and (SEQ ID NO:82) genes using the LightCycler96 real-time PCR system (Roche; Basel, Switzerland). Cycling conditions were as follows: reverse transcription (55° C. for 10 min) and initial denaturation (95° C. for 1 min) followed by 40 cycles of denaturation (95° C. for 10 sec) and extension (60° C. for 30 sec, with plate read). The fold change in gene expression was determined using the 2-DDCt method. The following qPCR primers were purchased from IDT.

Statistical Analysis:

Significance was determined using a one-way analysis of variance (ANOVA) with post hoc correction performed using a Dunnett's multiple comparison test. All statistical analyses were performed using the statistical software package GraphPad Prism 9. Significance was denoted as an asterisk with * p<0.05,  p<0.001 and * p<0.0001.

Example 2

In order to better understand how the DOTAP 40C LNPs act in vivo, we performed safety studies to evaluate acute toxicity and immune responses. Mice were treated with a high dose of 50 μg (approximately 2.5 mg/kg) DOTAP 40C LNPs or PBS (vehicle control) and evaluated for liver toxicity at 24 hours post administration. There was a non-significant difference between the DOTAP 40C LNP and PBS treated mice for serum alanine aminotransferase (ALT), aspartate aminotransferase (AST), blood urea nitrogen (BUN), and creatine (CREA) levels (FIGS. 4A-4D). There was one DOTAP 40C LNP treated mouse which appeared to have an elevated level of ALT; however, it falls within the normal ALT values for this strain. (Otto et al, J Am Assoc Lab Anim Sci 2016; 55: 375-386). This experiment indicates that the DOTAP 40C LNPs did not cause significant hepatic toxicity 24 hours after administration.

Figure 5A:
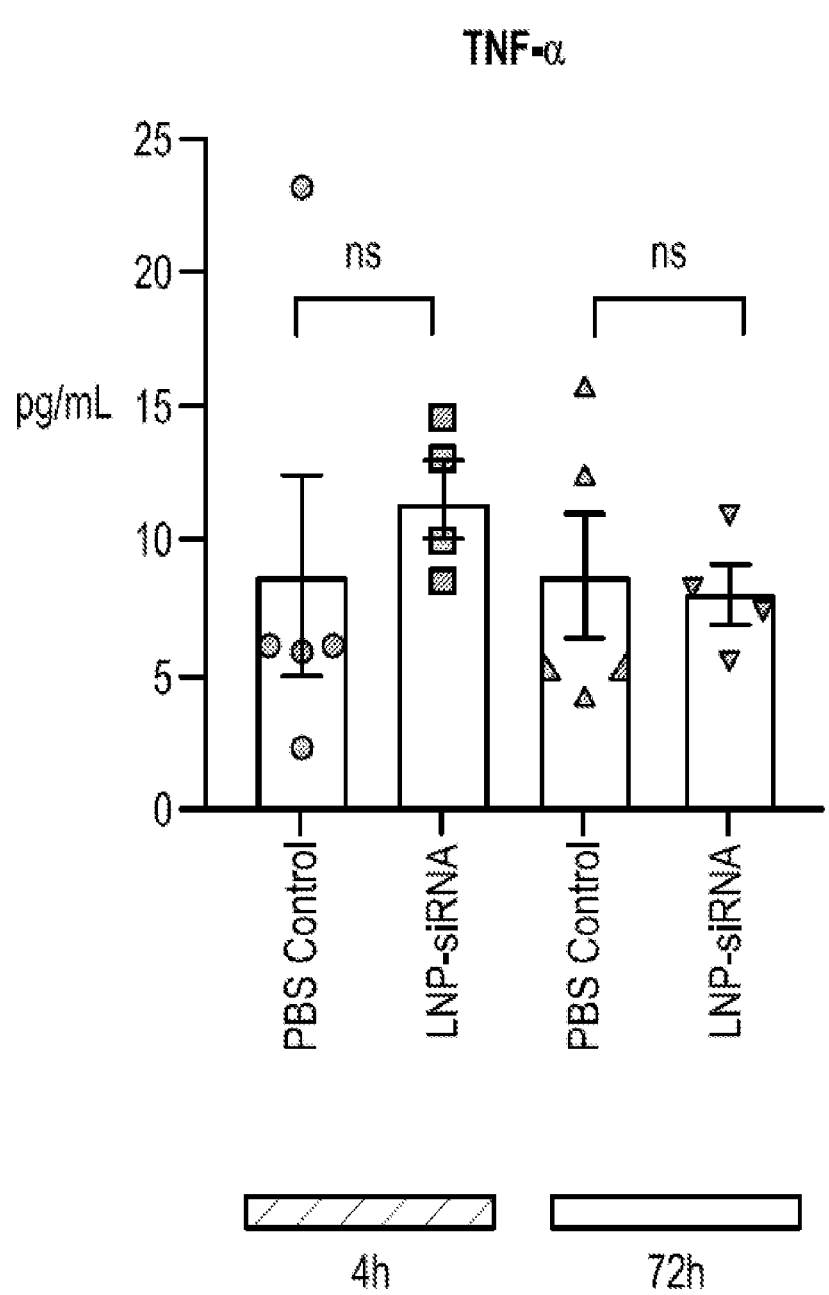
FIGS. 5A-5E: Evaluating DOTAP 40C LNP safety profile. C57BL/6 mice were evaluated for liver toxicity and cytokine levels after a 2.5 mg/kg dose of DOTAP 40C LNPs (LNP-siRNA) or PBS vehicle control by intravenous administration. A universal negative control (NC) siRNA was encapsulated in DOTAP 40 LNPs for this study. (A) Twenty-four hours post administration whole blood was collected and was evaluated for liver toxicity using a VetScan Mammalian Liver Profile kit. Luminex serum cytokine analysis of TNF-α (FIG. 5A), IL-6 (FIG. 5B), IFN-γ (FIG. 5C), IFN-α (FIG. 5D), and IFN-β (FIG. 5E) at 4 and 72 hours post LNP administration. Data presented as mean±S.E.M for n=5 for PBS mice and n=4 for LNP-siRNA mice. Significance was determined using an unpaired, two-tailed t-test; ns=not significant, *** p<0.001.
Figure 5B:
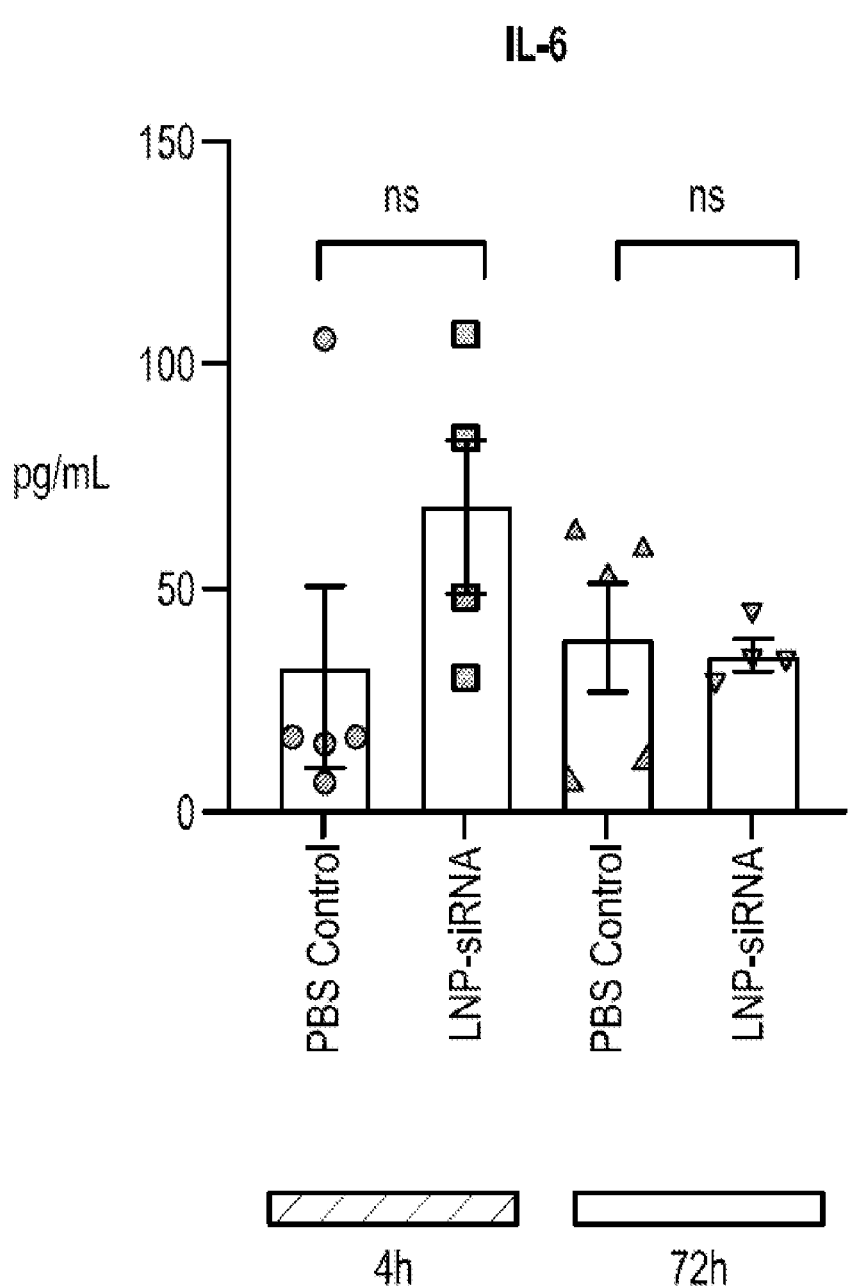
Figure 5C:
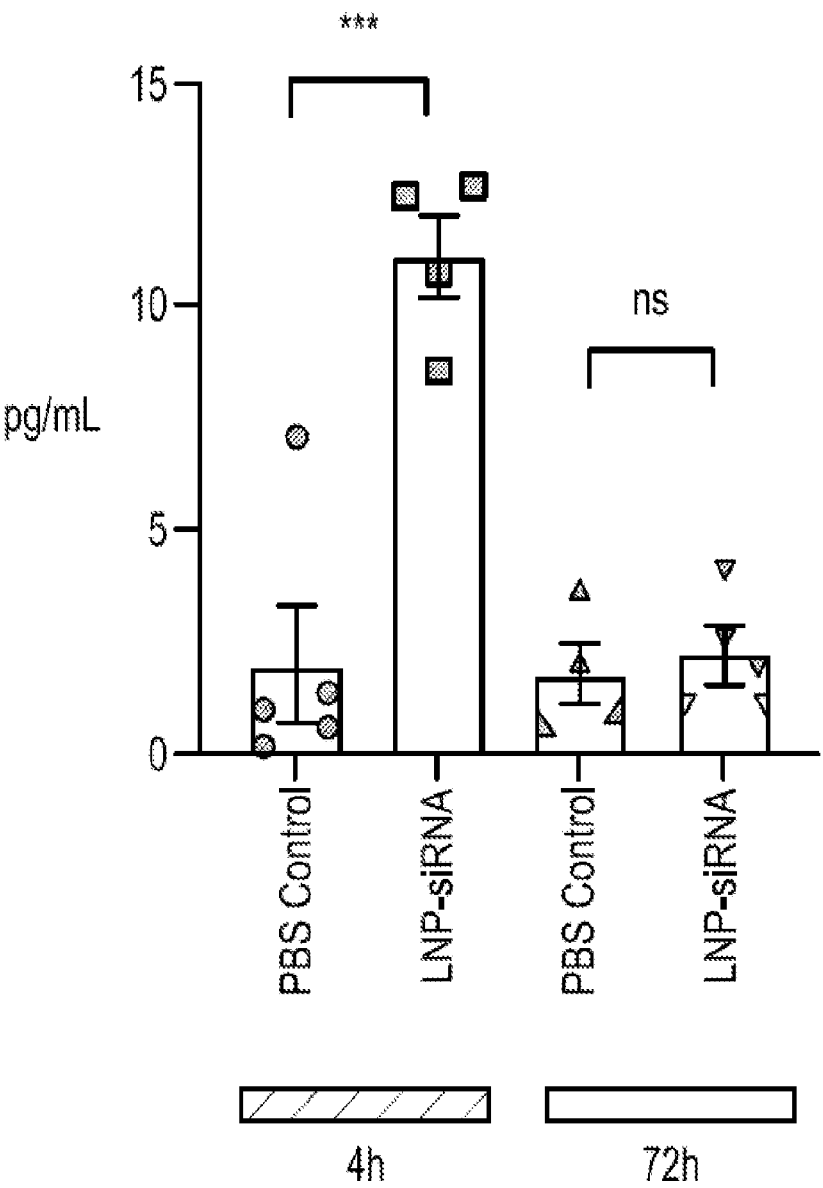
Figure 5D:
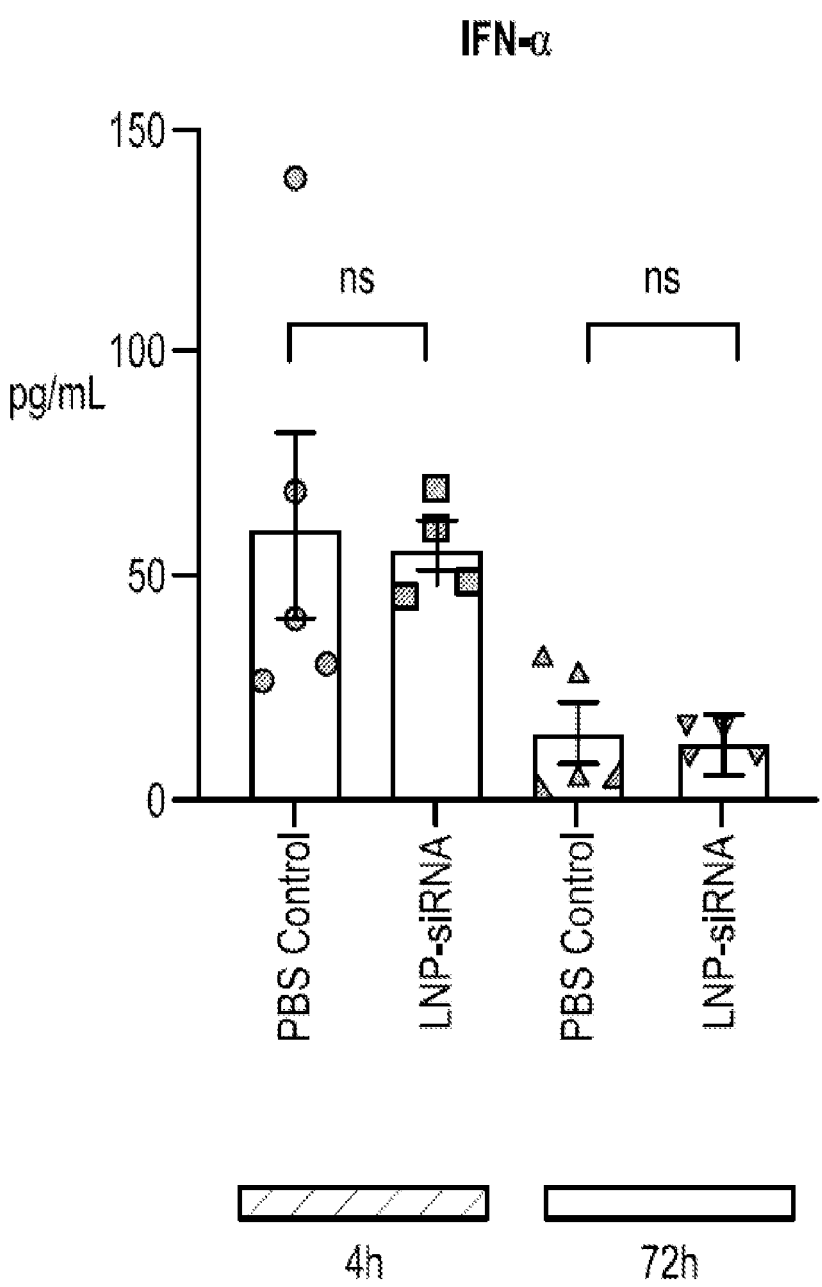
Figure 5E:
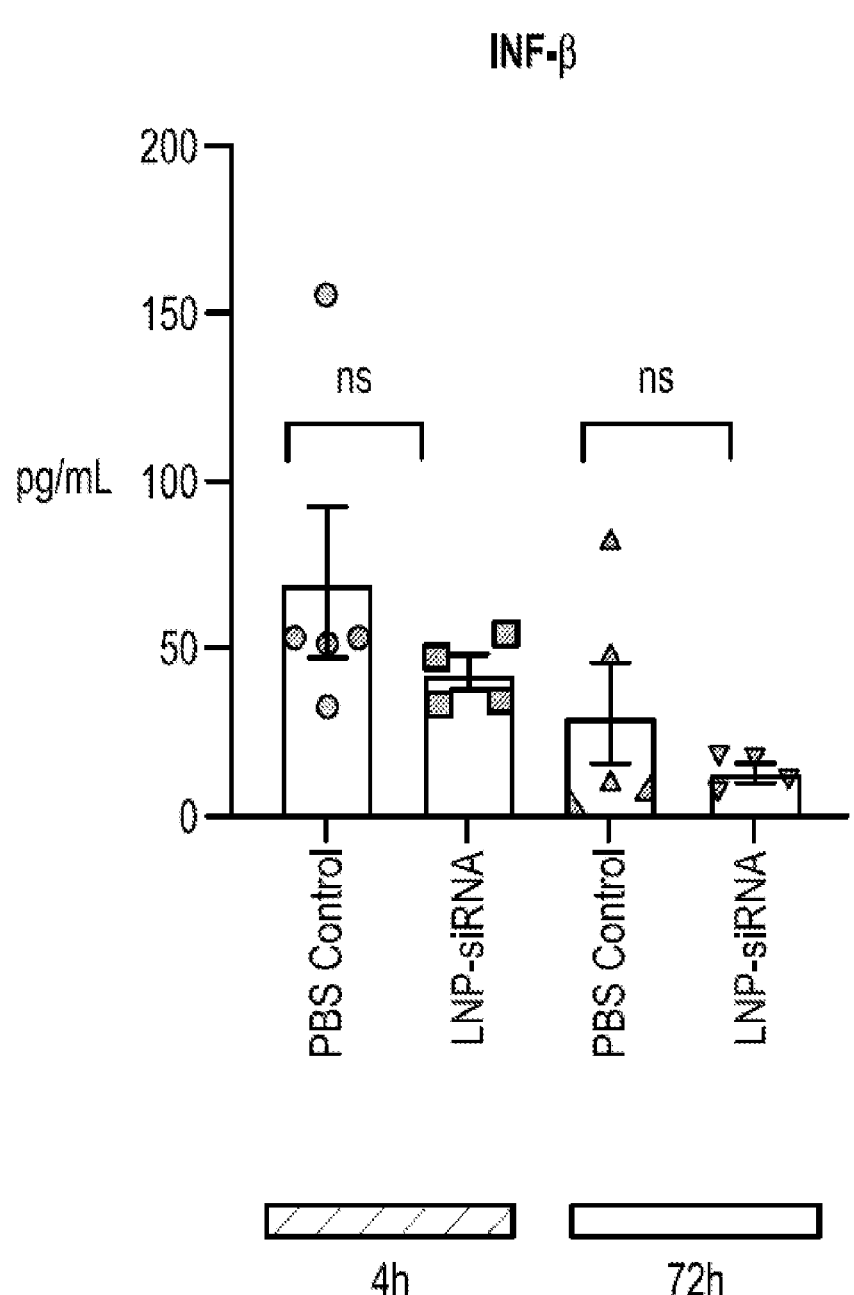

It is well known that LNPs have the potential to induce immunogenicity and evaluating the immune response of LNPs is a critical component of their characterization. (Zolnik et al, Endocrinology 2010; 151: 458-465). There are many systemically delivered LNP formulations, including those with the FDA approved lipid MC3, that demonstrate a small spike in inflammatory cytokines within hours of administration that resolves shortly after. (Maugeri et al, Nat Commun 2019; 10: 4333; Riley et al, Sci Adv 2021; 7. doi:10.1126/sciadv.aba1028; Kumar et al, Mol Ther Nucleic Acids 2014; 3: e210). We investigated serum cytokine release in response to DOTAP 40C LNPs at 4 and 72 hours post administration (FIGS. 5A-5E). An increase in TNF-α, IL-6, and IFN-γ was observed at 4 hours (FIGS. 5A-5C). However, these elevated levels resolved to levels similar to PBS by 72 hours. There was no significant difference between the treatment groups in the serum levels of IFN-α and IFN-β at 4 and 72 h post administration, indicating that the encapsulated siRNAs do not stimulate the RIG-I pathway (FIG. 5A, 5C).

Discussion

Exploring the liver toxicity of the DOTAP 40C LNPs revealed no significant difference in serum ALT, AST, BUN, and CREA levels compared to PBS vehicle control mice at 24 hours post-administration. Preliminary studies of immune activation of DOTAP 40C LNPs revealed an increase in TNF-α, IL-6, and IFN-γ at 4 hours post administration that resolves by 72 hours. Acute increases in these cytokines have been previously observed for LNP formulations including the FDA approved lipid MC3. (Maugeri et al, Nat Commun 2019; 10: 4333; Riley et al, Sci Adv 2021; 7. doi:10.1126/sciadv.aba1028). A recent study by Alameh et al, Immunity 2021; 54: 2877-2892.e7, demonstrated that the ionizable lipid in the BioNTech COVID-19 mRNA vaccine is responsible for an increase in IL-6 which provides adjuvant activity and enhances efficacy of the vaccine. Taken together, the data indicate that our novel formulation falls within the acceptable parameters for use as a delivery vehicle.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

52
Methods

To evaluate the safety profile of the DOTAP 40C LNPs liver toxicity and cytokine levels were assessed post treatment. Twelve- to thirteen-week-old female C57BL/6N mice (Jackson Laboratory; MA, USA) were injected via tail vein with 50 μg of LNP-siRNAs or PBS vehicle control (in a total volume of 200 μl) (n=4 for per LNP treatment and n=5 PBS mice). This study was approved by the City of Hope IACUC (#20025).

Liver Toxicity Analysis

Twenty-four hours after siRNA-LNP administration approximately ~200 μl of blood was collected in heparin tubes (Greiner Bio-One #22-030-406; Kremsmunster, Austria) for liver toxicity analysis using the VetScan Mammalian Liver Profile kit (Abaxis #500-0040-12; CA, USA). Immediately following collection, whole blood of each animal was applied to the reagent rotor containing the assay components and inserted into the VetScan Chemistry Analyzer device (Abaxis; CA, USA).

Luminex Cytokine Analysis

Serum was collected for cytokine analysis at 4, and 72 hours using Essential Th1/Th2 Cytokine 6-Plex Mouse ProcartaPlex and IFN-alpha/IFN-beta 2-Plex Mouse ProcartaPlex Panels (Invitrogen #EPX060-20831-901 and EPX02A-22187-901). Panels were analyzed by the Analytical Pharmacology Core (City of Hope, Duarte, CA) using the Flexmap 3D Luminex system (Luminexcorp; TX, USA). Cytokine concentrations were calculated using the Bio-Plex Manager 6.2 software (Bio-Rad; CA, USA) with a five parameter curve-fitting algorithm applied for standard curve calculations for duplicate samples. Data is reported as mean S.E.M.

Information Sequence Listing

For SEQ ID NOS:1-82, "m" preceding a nucleotide means that nucleotide based is modified with 2'O-methyl, * refers to a phosphorothioate linkage between two nucleotides. The nucleotides of SEQ ID NOS:1-82 have ribose sugars except that those that are underlined have a deoxyribose sugar.

```
SEQ ID NO: 1 = UTR3 (unmodified dsiRNA sense sequence)
5'AUACCUUCCCAGGUAACAAACCAAC 3'

SEQ ID NO: 2 = UTR3 (dsiRNA sense sequence)
5'AmUmACmCmUUCCmCmAGGUAmAmCA*A*ACCAAC 3', SEQ ID NO: 3 = siUTR3 (unmodified siRNA antisense sequence)
5' GUUGGUUUGUUACCUGGGAAGGUAUAA 3'

SEQ ID NO: 4 = siUTR3 (siRNA antisense sequence)
5' G*UUGGUUUGUmUmAmCCUGGGAAGGmUAmUmAA 3'

SEQ ID NO: 5 = siUTR1 (unmodified dsiRNA sense sequence)
5'GUCCCUGGUUUCAACGAGAAAACAC 3'

SEQ ID NO: 6 = siUTR1 (dsiRNA sense sequence)
5'GmUmCCCmCmUGGUUmUmCAmAmCGAG*A*AAAmCAC 3'

SEQ ID NO: 7 = siUTR1 (unmodified siRNA antisense sequence)
5' GUGUUUUCUCGUUGAAACCAGGGACAA 3'

SEQ ID NO: 8 = siUTR1 (siRNA antisense sequence)
3' AmAmCmAGGGmAmCCAAAGUUGmCmUCUUUUGU*G 5'

SEQ ID NO: 9 =
UGGACUGAGACUGACCUUACU
```

-continued

```
SEQ ID NO: 10 =
UAAGGUCAGUCUCAGUCCAAC

SEQ ID NO: 11 =
ACCUUAUAAUUCACAGAAUGCUGUA

SEQ ID NO: 12 =
UACAGCAUUCUGUGAAUUAUAAGGUGA

SEQ ID NO: 13 =
AACUUAUGUACUCAUUCGUUU

SEQ ID NO: 14 =
ACGAAUGAGUACAUAAGUUCG

SEQ ID NO: 15 =
AACCACCUUGUAGGUUUGUUA

SEQ ID NO: 16 =
ACAAACCUACAAGGUGGUUCC

SEQ ID NO: 17 =
UGUUGAUUCAUCACAGGGCUCAGAA

SEQ ID NO: 18 =
UUCUGAGCCCUGUGAUGAAUCAACAGU

SEQ ID NO: 19 =
ACUUAUGUACUCAUUCGUUUC

SEQ ID NO: 20 =
AACGAAUGAGUACAUAAGUUC

SEQ ID NO: 21 =
UUUGAAUGUGGCUAAAUCUGA

SEQ ID NO: 22 =
AGAUUUAGCCACAUUCAAAGA

SEQ ID NO: 23 =
ACCACCUUGUAGGUUUGUUAC

SEQ ID NO: 24 =
AACAAACCUACAAGGUGGUUC

SEQ ID NO: 25 =
UGGAACCACCUUGUAGGUUUG

SEQ ID NO: 26 =
AACCUACAAGGUGGUUCCAGU

SEQ ID NO: 27 =
ACUGGAACCACCUUGUAGGUU

SEQ ID NO: 28 =
CCUACAAGGUGGUUCCAGUUC

SEQ ID NO: 29 =
AUGAUGAUUAUUUCAAUAAAA

SEQ ID NO: 30 =
UUAUUGAAAUAAUCAUCAUCA

SEQ ID NO: 31 =
ACUAUAUGUUAAACCAGGUGG

SEQ ID NO: 32 =
ACCUGGUUUAACAUAUAGUGA

SEQ ID NO: 33 =
GCUUAGUAGAAGUUGAAAAAGGCGT

SEQ ID NO: 34 =
ACGCCUUUUUCAACUUCUACUAAGCCA

SEQ ID NO: 35 =
AAGAUGGCACUUGUGGCUUAGUAGA

SEQ ID NO: 36 =
UCUACUAAGCCACAAGUGCCAUCUUUA
```

-continued

SEQ ID NO: 37 =
CCCUGGUUUCAACGAGAAAACAC<u>AC</u>

SEQ ID NO: 38 =
GUGUGUUUUCUCGUUGAAACCAGGGAC

SEQ ID NO: 39 =
UAUGGGUUGGGAUUAUCCUAAAUG<u>T</u>

SEQ ID NO: 40 =
ACAUUUAGGAUAAUCCCAACCCAUAAG

SEQ ID NO: 41 =
CAAAGAAUAGAGCUCGCACCGUAG<u>C</u>

SEQ ID NO: 42 =
GCUACGGUGCGAGCUCUAUUCUUUGCA

SEQ ID NO: 43 =
UAUGGGUUGGGAUUACCCUAAAUG<u>T</u>

SEQ ID NO: 44 =
ACAUUUAGGGUAAUCCCAACCCAUAAG

SEQ ID NO: 45 =
CGAACUUAUGUACUCAUUCGU

SEQ ID NO: 46 =
GAACUUAUGUACUCAUUCGUU

SEQ ID NO: 47 =
UCUUUGAAUGUGGCUAAAUCU

SEQ ID NO: 48 =
GAACCACCUUGUAGGUUUGUU

SEQ ID NO: 49 =
ACUGGAACCACCUUGUAGGUU

SEQ ID NO: 50 = GGAACCACCUUGUAGGUUUGU

SEQ ID NO: 51 =
GUUGGACUGAGACUGACCUUA

SEQ ID NO: 52 =
GAACUGGAACCACCUUGUAGG

SEQ ID NO: 53 =
UGAUGAUGAUUAUUUCAAUAA

SEQ ID NO: 54 =
UCACUAUAUGUUAAACCAGGU

SEQ ID NO: 55 =
UUGUCCCUGGUUUCAACGAGA

SEQ ID NO: 56 =
UGGCUUAGUAGAAGUUGAAAA

SEQ ID NO: 57 =
UUAUACCUUCCCAGGUAACAA

SEQ ID NO: 58 =
UAAAGAUGGCACUUGUGGCUU

SEQ ID NO: 59 =
GUCCCUGGUUUCAACGAGAAA

SEQ ID NO: 60 =
CUUAUGGGUUGGGAUUAUCCU

SEQ ID NO: 61 =
UGCAAAGAAUAGAGCUCGCAC

SEQ ID NO: 62 =
ACUGUUGAUUCAUCACAGGGC

SEQ ID NO: 63 =
UCACCUUAUAAUUCACAGAAU

-continued

SEQ ID NO: 64 =
CUUAUGGGUUGGGAUUAUCCA

SEQ ID NO: 65 =
UGCUAAGAAUAGAGCUCGCAC

SEQ ID NO: 66 =
ACUGUUGAUUCAUCACAGGGU

SEQ ID NO: 67 =
ACUGUUGAUUCCUCACAGGGU

SEQ ID NO: 68 =
UCACCUUAUAAUUCACAGAAC

SEQ ID NO: 69 =
UCGCCUUAUAAUUCACAGAAU

SEQ ID NO: 70 =
CAUAUUGCGCGUAUAGUCGCGUUAG

SEQ ID NO: 71 =
CUAACGCGACUAUACGCGCAAUAUGGU

SEQ ID NO: 72 =
GACUUUCCGCUGGGGACUUUC

SEQ ID NO: 73 =
UGGAAAGUCCCCAGCGGAAAG

SEQ ID NO: 74 =
CUGACCUUUGGAUGGUGCUUC

SEQ ID NO: 75 =
UGGAAAGUCCCCAGCGGAAAG

SEQ ID NO: 76 =
GACUUGGUGUGGAAGGCGCAGAACA

SEQ ID NO: 77 =
UGUUCUGCGCCUUCCACACCAAGUCAG

SEQ ID NO: 78 =
CUUAUGGGUUGGGAUUACCCU

SEQ ID NO: 79 =
GAGAGGCTAAGAAGCAGC

SEQ ID NO: 80 =
ACGCAGTTCCTCGCTGTAA

SEQ ID NO: 81 =
GCTACAGCTTCACCACCACA

SEQ ID NO: 82 =
TCTCCAGGGAGGAAGAGGAT

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A lipid nanoparticle comprising:

(i) about 36 mole % to about 44 mole % of a cationic lipid; wherein the cationic lipid is N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), 1,2-dioleoyloxy-3-(trimethylammonium)propane (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propanaminium-trifluoroacetate (DOSPA), dioctadecylamidoglycyl spermine (DOGS), N,N-dimethyl-3,4-dioleyloxybenzylamine (DMOBA), 1,2-N,N'-dioleylcarbamyl-3-dimethylaminopropane (DOcarbDAP), 3-(N,N-dioleylamino)-1,2-propanedio (DOAP), or a mixture of two or more thereof;

(ii) about 21 mole % to about 29 mole % of a dilinoleic cationic lipid; wherein the dilinoleic cationic lipid is dilinoleyl-methyl-4-dimethylaminobutyrate (MC3), 1,2-dilinoleyloxy-N,N-dimethylaminopropane (DLinDMA), 2,2-dilinoleyl-4-(2-dimethylaminoethyl)-[1,3]-dioxolane (DLin-KC2-DMA), 2,2-dilinoleyl-4-(3-dimethylaminopropyl)-[1,3]-dioxolane (DLin-K-3-DMA), 2,2-dilinoleyl-4-(4-dimethylaminobutyl)-[1,3]-dioxolane (DLin-KC4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 1,2-N,N'-dilinoleylcarbamyl-3-dimethylaminopropane (DLincarbDAP), or a combination of two or more thereof;

(iii) about 6 mole % to about 14 mole % of a phospholipid; wherein the phospholipid is dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine (MMPE), dimethyl-phosphatidylethanolamine (DMPE), dielaidoyl-phosphatidylethanolamine (DEPE), stearoyloleoyl-phosphatidylethanolamine (SOPE), egg phosphatidylcholine (EPC), hydrogenated soy phosphatidylcholine (HSPC), or a mixture of two or more thereof;

(iv) about 18 mole % to 26 mole % of a sterol; wherein the sterol is cholesterol, cholestanol, cholestanone, cholestenone, coprostanol, cholesteryl-2'-hydroxyethyl ether, cholesteryl-4'-hydroxybutyl ether, or a mixture of two or more thereof; and (v) about 1 mole % to about 4 mole % of a polyethylene glycol-lipid conjugate; wherein polyethylene glycol-lipid conjugate is N-palmitoyl-sphingosine-1-{succinyl [methoxy(polyethylene glycol)]} (C16 PEG ceramide), 1,2-dimyristoyl-rac-glycero-3-methoxypolyethylene glycol (DMG-PEG), 1,2-dipalmitoyl-sn-glycero-3-phosphoethanolamine-N-[azido(polyethylene glycol)] (DPPE-PEG), 1,2-dipalmitoyl-rac-glycero-3-methylpolyoxyethylene (DPG-PEG), distearoyl-rac-glycerol (polyethylene glycol) (DSG-PEG), 1,2-distearoyl-sn-glycero-3-phosphoethanolamine-N-[amino (polyethylene glycol) (DSPE-PEG), or a mixture of two or more thereof; wherein the polyethylene glycol has an average molecular weight from about 1,000 Daltons to about 6,000 Daltons.

2. The lipid nanoparticle of claim 1, comprising:
(i) about 38 mole % to about 42 mole % of the cationic lipid;
(ii) about 23 mole % to about 27 mole % of the dilinoleic cationic lipid;
(iii) about 8 mole % to about 12 mole % of the phospholipid;
(iv) about 20 mole % to 24 mole % of the sterol; and
(v) about 2 mole % to about 4 mole % of the polyethylene glycol-lipid conjugate.

3. The lipid nanoparticle of claim 1, comprising:
(i) about 40 mole % of the cationic lipid;
(ii) about 25 mole % of the dilinoleic cationic lipid;
(iii) about 10 mole % of the phospholipid;
(iv) about 22 mole % of the sterol; and
(v) about 3 mole % of the polyethylene glycol-lipid conjugate.

4. The lipid nanoparticle of claim 1, wherein:
(i) the cationic lipid is DOTAP;
(ii) the dilinoleic cationic lipid is MC3;
(iii) the phospholipid is DSPC, DPPC, DOPE, POPC, POPE, POPG, DPPE, DMPE, DSPE, MMPE, DMPE, DEPE, SOPE, EPC, or HSPC;
(iv) the sterol is cholesterol, cholestanol, cholestanone, cholestenone, coprostanol, cholesteryl-2'-hydroxyethyl ether, or cholesteryl-4'-hydroxybutyl ether;
(v) the polyethylene glycol-lipid conjugate is C16 PEG ceramide, DMG-PEG, DPPE-PEG, DPG-PEG, DSG-PEG, or DSPE-PEG, wherein the polyethylene glycol has an average molecular weight from about 1,000 Daltons to about 6,000 Daltons.

5. The lipid nanoparticle of claim 4, wherein the polyethylene glycol-lipid conjugate is C16 PEG ceramide.

6. The lipid nanoparticle of claim 1, wherein
(i) the cationic lipid is DOTAP;
(ii) the dilinoleic cationic lipid is MC3;
(iii) the phospholipid is DSPC;
(iv) the sterol is cholesterol; and
(v) the polyethylene glycol-conjugated lipid is C16 PEG2000 ceramide.

7. The lipid nanoparticle of claim 1, further comprising a nucleic acid encapsulated within the lipid nanoparticle.

8. The lipid nanoparticle of claim 7, wherein the nucleic acid is RNA or DNA.

9. The lipid nanoparticle of claim 8, wherein the RNA is siRNA or mRNA, and wherein the DNA is a plasmid or a minigene.

10. The lipid nanoparticle of claim 7, wherein the nucleic acid comprises 15 nucleotides to 30 nucleotides and is capable of hybridizing to SEQ ID NO:57, SEQ ID NO: 51, SEQ ID NO:63, SEQ ID NO:55, SEQ ID NO:45, SEQ ID NO:50, or SEQ ID NO:62.

11. The lipid nanoparticle of claim 7, wherein the nucleic acid comprises SEQ ID NO: 1 hybridized to SEQ ID NO:3; SEQ ID NO:2 hybridized to SEQ ID NO: 4; SEQ ID NO:9 hybridized to SEQ ID NO: 10; SEQ ID NO:11 hybridized to SEQ ID NO: 12; SEQ ID NO:5 hybridized to SEQ ID NO:7; SEQ ID NO:6 hybridized to SEQ ID NO:8; SEQ ID NO:13 hybridized to SEQ ID NO:14; SEQ ID NO:15 hybridized to SEQ ID NO:16; SEQ ID NO:17 hybridized to SEQ ID NO:18; SEQ ID NO: 19 hybridized to SEQ ID NO:20; SEQ ID NO:21 hybridized to SEQ ID NO:22; SEQ ID NO:23 hybridized to SEQ ID NO:24; SEQ ID NO:25 hybridized to SEQ ID NO:26; SEQ ID NO:27 hybridized to SEQ ID NO:28; SEQ ID NO:29 hybridized to SEQ ID NO:30; SEQ ID NO:31 hybridized to SEQ ID NO:32; SEQ ID NO:33 hybridized to SEQ ID NO:34; SEQ ID NO:35 hybridized to SEQ ID NO:36; SEQ ID NO:37 hybridized to SEQ ID NO:38; SEQ ID NO:39 hybridized to SEQ ID NO:40; SEQ ID NO:41 hybridized to SEQ ID NO:42; SEQ ID NO:43 hybridized to SEQ ID NO:44; or a combination of two or more of the foregoing.

12. A plurality of the lipid nanoparticles of claim 1.

13. The lipid nanoparticle of claim 12, wherein a plurality of the lipid nanoparticles have an average size from about 50 nm to about 110 nm.

14. The lipid nanoparticle of claim 12, wherein a plurality of the lipid nanoparticles have a zeta potential from about 10 mV to about 30 mV.

15. The lipid nanoparticle of claim 12, wherein a plurality of the lipid nanoparticles have a polydispersity from about 0.12 to 0.2.

16. A pharmaceutical composition comprising the lipid nanoparticle of claim 1 and a pharmaceutically acceptable excipient.

17. A method for administering a lipid nanoparticle to a lung of a patient in need thereof, the method comprising administering to the patient the lipid nanoparticle of claim 1.

18. A method for treating a SARS coronavirus infection in a patient in need thereof, the method comprising administering to the patient the lipid nanoparticle of claim 1.

19. A lipid nanoparticle comprising:
(i) about 38 mole % to about 42 mole % of 1,2-dioleoyloxy-3-(trimethylammonium)propane (DOTAP);
(ii) about 23 mole % to about 27 mole % of dilinoleyl-methyl-4-dimethylaminobutyrate (MC3);
(iii) about 6 mole % to about 14 mole % of distearoylphosphatidylcholine (DSPC);
(iv) about 18 mole % to about 26 mole % of cholesterol; and (v) about 1 mole % to about 4 mole % of N-palmitoyl-sphingosine-1-{succinyl[methoxy(polyethylene glycol)]}, wherein the polyethylene glycol has an average molecular weight of about 2,000 Daltons.

20. A plurality of the lipid nanoparticle of claim 19; wherein the plurality of the lipid nanoparticles have an average size from about 50 nm to about 110 nm, a zeta potential from about 10 mV to about 30 mV, and a polydispersity from about 0.12 to 0.2.

\* \* \* \* \*

SEQUENCE LISTING

<160> NUMBER OF SEQ ID NOS: 82

<210> SEQ ID NO 1
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 1
auaccuuccc agguaacaaa ccaac                                           25

-continued

```
<210> SEQ ID NO 2
<211> LENGTH: 35
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(35)
<223> OTHER INFORMATION: "m" is 2'O-methyl and "n" is phosphorothioate
      linkage

<400> SEQUENCE: 2
amumacmcmu uccmcmaggu amamcanana ccaac                                 35

<210> SEQ ID NO 3
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 3
guugguuugu uaccugggaa gguauaa                                          27

<210> SEQ ID NO 4
<211> LENGTH: 34
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(34)
<223> OTHER INFORMATION: "m" is 2'O-methyl and "n" is phosphorothioate
      linkage

<400> SEQUENCE: 4
gnuugguuug umumamccug ggaaggmuam umaa                                  34

<210> SEQ ID NO 5
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 5
gucccugguu ucaacgagaa aacac                                            25

<210> SEQ ID NO 6
<211> LENGTH: 36
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(36)
<223> OTHER INFORMATION: "m" is 2'O-methyl and "n" is phosphorothioate
      linkage

<400> SEQUENCE: 6
gmumccmcmu gguumumcam amcgagnana aamcac                                36

<210> SEQ ID NO 7
<211> LENGTH: 27
<212> TYPE: RNA
```

-continued

```
<213> ORGANISM: Artificial Sequence
<220> FEATURE:
<223> OTHER INFORMATION: Synthetic Polynucleotide

<400> SEQUENCE: 7
guguuuucuc guugaaacca gggacaa                                          27

<210> SEQ ID NO 8
<211> LENGTH: 35
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(35)
<223> OTHER INFORMATION: "m" is 2'O-methyl and "n" is phosphorothioate
      linkage

<400> SEQUENCE: 8
amamcmaggg mamccaaagu ugmcmucuuu ugung                                 35

<210> SEQ ID NO 9
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 9
uggacugaga cugaccuuac u                                                21

<210> SEQ ID NO 10
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 10
uaaggucagu cucaguccaa c                                                21

<210> SEQ ID NO 11
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 11
accuuauaau ucacagaaug cugua                                            25

<210> SEQ ID NO 12
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 12
uacagcauuc ugugaauuau aagguga                                          27

<210> SEQ ID NO 13
<211> LENGTH: 21
<212> TYPE: RNA
<213> ORGANISM: Artificial Sequence
<220> FEATURE:
```

<223> OTHER INFORMATION: Synthetic Polynucleotide

<400> SEQUENCE: 13
aacuuaugua cucauucguu u                                                    21

<210> SEQ ID NO 14
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 14
acgaaugagu acauaaguuc g                                                    21

<210> SEQ ID NO 15
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 15
aaccaccuug uagguuuguu a                                                    21

<210> SEQ ID NO 16
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 16
acaaaccuac aaggugguuc c                                                    21

<210> SEQ ID NO 17
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 17
uguugauuca ucacagggcu cagaa                                                25

<210> SEQ ID NO 18
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 18
uucugagccc ugugaugaau caacagu                                              27

<210> SEQ ID NO 19
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 19
acuuauguac ucauucguuu c                                                    21

-continued

```
<210> SEQ ID NO 20
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 20
aacgaaugag uacauaaguu c                                             21

<210> SEQ ID NO 21
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 21
uuugaaugug gcuaaaucug a                                             21

<210> SEQ ID NO 22
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 22
agauuuagcc acauucaaag a                                             21

<210> SEQ ID NO 23
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 23
accaccuugu agguuuguua c                                             21

<210> SEQ ID NO 24
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 24
aacaaaccua caaggugguu c                                             21

<210> SEQ ID NO 25
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 25
uggaaccacc uuguagguuu g                                             21

<210> SEQ ID NO 26
<211> LENGTH: 21
<212> TYPE: RNA
<213> ORGANISM: Artificial Sequence
<220> FEATURE:
<223> OTHER INFORMATION: Synthetic Polynucleotide
```

-continued

```
<400> SEQUENCE: 26
aaccuacaag gugguuccag u                                          21

<210> SEQ ID NO 27
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 27
acuggaacca ccuuguaggu u                                          21

<210> SEQ ID NO 28
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 28
ccuacaaggu gguuccaguu c                                          21

<210> SEQ ID NO 29
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 29
augaugauua uuucaauaaa a                                          21

<210> SEQ ID NO 30
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 30
uuauugaaau aaucaucauc a                                          21

<210> SEQ ID NO 31
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 31
acuauauguu aaaccaggug g                                          21

<210> SEQ ID NO 32
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 32
accugguuua acauauagug a                                          21

<210> SEQ ID NO 33
<211> LENGTH: 25
```

```
<212> TYPE: DNA
<213> ORGANISM: Artificial Sequence
<220> FEATURE:
<223> OTHER INFORMATION: Synthetic Polynucleotide

<400> SEQUENCE: 33
gcuuaguaga aguugaaaaa ggcgt                                              25

<210> SEQ ID NO 34
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 34
acgccuuuuu caacuucuac uaagcca                                            27

<210> SEQ ID NO 35
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 35
aagauggcac uuguggcuua guaga                                             25

<210> SEQ ID NO 36
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 36
ucuacuaagc cacaagugcc aucuuua                                            27

<210> SEQ ID NO 37
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 37
cccugguuuc aacgagaaaa cacac                                             25

<210> SEQ ID NO 38
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 38
guguguuuuc ucguugaaac cagggac                                            27

<210> SEQ ID NO 39
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 39
```

-continued

```
uauggguugg gauuauccua aaugt                                      25

<210> SEQ ID NO 40
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 40
acauuuagga uaaucccaac ccauaag                                    27

<210> SEQ ID NO 41
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 41
caaagaauag agcucgcacc guagc                                      25

<210> SEQ ID NO 42
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 42
gcuacggugc gagcucuauu cuuugca                                    27

<210> SEQ ID NO 43
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 43
uauggguugg gauuacccua aaugt                                      25

<210> SEQ ID NO 44
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 44
acauuuaggg uaaucccaac ccauaag                                    27

<210> SEQ ID NO 45
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 45
cgaacuuaug uacucauucg u                                          21

<210> SEQ ID NO 46
<211> LENGTH: 21
<212> TYPE: RNA
<213> ORGANISM: Artificial Sequence
```

-continued

```
<220> FEATURE:
<223> OTHER INFORMATION: Synthetic Polynucleotide

<400> SEQUENCE: 46
gaacuuaugu acucauucgu u                                          21

<210> SEQ ID NO 47
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 47
ucuuugaaug uggcuaaauc u                                          21

<210> SEQ ID NO 48
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 48
gaaccaccuu guagguuugu u                                          21

<210> SEQ ID NO 49
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 49
acuggaacca ccuuguaggu u                                          21

<210> SEQ ID NO 50
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 50
ggaaccaccu uguagguuug u                                          21

<210> SEQ ID NO 51
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 51
guuggacuga gacugaccuu a                                          21

<210> SEQ ID NO 52
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 52
gaacuggaac caccuuguag g                                          21
```

-continued

```
<210> SEQ ID NO 53
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 53
ugaugaugau uauuucaaua a                                                  21

<210> SEQ ID NO 54
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 54
ucacuauaug uuaaaccagg u                                                  21

<210> SEQ ID NO 55
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 55
uugucccugg uuucaacgag a                                                  21

<210> SEQ ID NO 56
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 56
uggcuuagua gaaguugaaa a                                                  21

<210> SEQ ID NO 57
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 57
uuauaccuuc ccagguaaca a                                                  21

<210> SEQ ID NO 58
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 58
uaaagauggc acuuguggcu u                                                  21

<210> SEQ ID NO 59
<211> LENGTH: 21
<212> TYPE: RNA
<213> ORGANISM: Artificial Sequence
<220> FEATURE:
<223> OTHER INFORMATION: Synthetic Polynucleotide
```

<400> SEQUENCE: 59
gucccugguu ucaacgagaa a                                              21

<210> SEQ ID NO 60
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 60
cuuauggguu gggauuaucc u                                              21

<210> SEQ ID NO 61
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 61
ugcaaagaau agagcucgca c                                              21

<210> SEQ ID NO 62
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 62
acuguugauu caucacaggg c                                              21

<210> SEQ ID NO 63
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 63
ucaccuuaua auucacagaa u                                              21

<210> SEQ ID NO 64
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 64
cuuauggguu gggauuaucc a                                              21

<210> SEQ ID NO 65
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 65
ugcuaagaau agagcucgca c                                              21

<210> SEQ ID NO 66

```
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 66
acuguugauu caucacaggg u                                          21

<210> SEQ ID NO 67
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 67
acuguugauu ccucacaggg u                                          21

<210> SEQ ID NO 68
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 68
ucaccuuaua auucacagaa c                                          21

<210> SEQ ID NO 69
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 69
ucgccuuaua auucacagaa u                                          21

<210> SEQ ID NO 70
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 70
cauauugcgc guauagucgc guuag                                      25

<210> SEQ ID NO 71
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 71
cuaacgcgac uauacgcgca auauggu                                    27

<210> SEQ ID NO 72
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 72
```
gacuuuccgc uggggacuuu c                                                    21

<210> SEQ ID NO 73
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 73
uggaaagucc ccagcggaaa g                                                    21

<210> SEQ ID NO 74
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 74
cugaccuuug gauggugcuu c                                                    21

<210> SEQ ID NO 75
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 75
uggaaagucc ccagcggaaa g                                                    21

<210> SEQ ID NO 76
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 76
gacuuggugu ggaaggcgca gaaca                                                25

<210> SEQ ID NO 77
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 77
uguucugcgc cuuccacacc aagucag                                              27

<210> SEQ ID NO 78
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 78
cuuauggguu gggauuaccc u                                                    21

<210> SEQ ID NO 79
<211> LENGTH: 18
<212> TYPE: DNA

```
<213> ORGANISM: Artificial Sequence
<220> FEATURE:
<223> OTHER INFORMATION: Synthetic Polynucleotide

<400> SEQUENCE: 79
gagaggctaa gaagcagc                                                            18

<210> SEQ ID NO 80
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 80
acgcagttcc tcgctgtaa                                                           19

<210> SEQ ID NO 81
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 81
gctacagctt caccaccaca                                                          20

<210> SEQ ID NO 82
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 82
tctccaggga ggaagaggat                                                          20
```